(12) United States Patent
Baichwal et al.

(10) Patent No.: US 7,887,841 B2
(45) Date of Patent: Feb. 15, 2011

(54) CHRONOTHERAPEUTIC DOSAGE FORMS AND METHODS OF TREATMENT USING CHRONOTHERAPY

(76) Inventors: Anand R. Baichwal, 5 Kendall Dr., Wappingers Falls, NY (US) 12590; Paul Woodcook, 31 Mist Hill Dr., Brookfield, CT (US) 06804; Raymond Higgins, 5 Morey Rd., New Milford, CT (US) 06776; Jaclyn Cobb, 47 1/2 Brocket St., Niantic, CT (US) 06357

( * ) Notice: Subject to any disclaimer, the term of this patent is extended or adjusted under 35 U.S.C. 154(b) by 120 days.

(21) Appl. No.: 11/001,675

(22) Filed: Dec. 1, 2004

(65) Prior Publication Data

US 2005/0276853 A1 Dec. 15, 2005

Related U.S. Application Data

(63) Continuation of application No. 10/099,461, filed on Mar. 13, 2002, now abandoned.

(60) Provisional application No. 60/275,382, filed on Mar. 13, 2001.

(51) Int. Cl.
*A61K 9/22* (2006.01)
*A61K 9/20* (2006.01)
*A61K 9/28* (2006.01)

(52) U.S. Cl. .................. 424/468; 424/464; 424/465; 424/474

(58) Field of Classification Search .................. 424/464, 424/465
See application file for complete search history.

(56) References Cited

U.S. PATENT DOCUMENTS

| | | | |
|---|---|---|---|
| 3,131,123 A | 4/1964 | Masquelier | 167/57 |
| 4,248,858 A | 2/1981 | Guley et al. | 424/21 |
| 4,432,966 A | 2/1984 | Zeitoun et al. | 424/21 |
| 4,713,248 A | 12/1987 | Kjornaes et al. | 424/468 |
| 4,780,318 A | 10/1988 | Appelgren et al. | 424/469 |
| 4,786,505 A | 11/1988 | Lovgren et al. | 424/479 |
| 4,786,506 A | 11/1988 | Fontanelli | 424/470 |
| 4,841,231 A | 6/1989 | Angelucci | 324/73 |
| 4,842,867 A | 6/1989 | Ayer et al. | 424/473 |
| 4,844,905 A | 7/1989 | Ichikawa et al. | 424/451 |
| 4,851,231 A | 7/1989 | Urquhart et al. | 424/469 |
| 4,853,230 A | 8/1989 | Lovgren et al. | 424/466 |
| 4,853,249 A | 8/1989 | Takashima et al. | 427/3 |
| 4,857,337 A | 8/1989 | Miller et al. | 424/480 |
| 4,863,742 A | 9/1989 | Panoz et al. | 424/473 |
| 4,871,549 A | 10/1989 | Ueda et al. | 424/494 |
| 4,882,169 A | 11/1989 | Ventouras | 424/493 |
| 4,886,669 A | 12/1989 | Ventouras | 424/469 |
| 4,888,179 A | 12/1989 | Appelgren et al. | 424/480 |
| 4,894,240 A | 1/1990 | Geoghegan et al. | 424/497 |
| 4,904,476 A | 2/1990 | Mehta et al. | 424/456 |
| 4,910,021 A | 3/1990 | Davis et al. | 424/456 |
| 4,933,186 A | 6/1990 | Ohm et al. | 424/476 |
| 4,971,805 A | 11/1990 | Kitanishi et al. | 424/494 |
| 4,975,284 A | 12/1990 | Stead et al. | 424/497 |
| 4,994,276 A | 2/1991 | Baichwal et al. | 424/440 |
| 5,007,790 A | 4/1991 | Shell | 424/451 |
| 5,032,406 A | 7/1991 | Dansereau et al. | 424/472 |
| 5,035,899 A | 7/1991 | Saeki et al. | 424/480 |
| 5,096,717 A | 3/1992 | Wirth et al. | 424/490 |
| 5,128,143 A | 7/1992 | Baichwal et al. | 424/464 |
| 5,135,757 A | 8/1992 | Baichwal et al. | 424/468 |
| 5,158,777 A | 10/1992 | Abramowitz et al. | 424/458 |
| 5,169,639 A | 12/1992 | Baichwal et al. | 424/468 |
| 5,175,003 A | 12/1992 | Goldman | 424/484 |
| 5,190,765 A | 3/1993 | Jao et al. | 424/473 |
| 5,202,338 A | 4/1993 | Bar et al. | 514/314 |
| 5,217,720 A | 6/1993 | Sekigawa et al. | 424/480 |
| 5,217,997 A | 6/1993 | Levere et al. | 514/565 |
| 5,229,131 A | 7/1993 | Amidon et al. | 424/451 |
| 5,232,706 A | 8/1993 | Palomo Coll | 424/475 |
| 5,234,947 A | 8/1993 | Cherksey | 514/449 |
| 5,238,686 A | 8/1993 | Eichel et al. | 424/461 |
| 5,252,338 A | 10/1993 | Jao et al. | 424/473 |
| 5,260,069 A | 11/1993 | Chen | 424/451 |
| 5,262,172 A | 11/1993 | Sipos | 424/490 |
| 5,275,824 A | 1/1994 | Carli et al. | 424/490 |
| 5,294,448 A | 3/1994 | Ring et al. | 424/497 |
| 5,296,233 A | 3/1994 | Batista et al. | 424/463 |

(Continued)

FOREIGN PATENT DOCUMENTS

DE 3943242 6/1990

(Continued)

OTHER PUBLICATIONS

Maggi, L., Massolini, G., De Lorenzi, E., Caccialanza G., Conte, U.; "Stereoselective Release From Press-Coated Tablets"; Dept. Of Pharmaceutical Chemistry, University of Pavia, I-27100 Pavia, Italy 1996.

(Continued)

*Primary Examiner*—Humera N Sheikh
(74) *Attorney, Agent, or Firm*—Davidson, Davidson & Kappel, LLC

(57) ABSTRACT

A chronotherapeutic pharmaceutical formulation comprising a core containing an active agent (e.g., a drug) and a delayed release compression coating comprising a natural or synthetic gum applied onto the surface of the core.

22 Claims, No Drawings

U.S. PATENT DOCUMENTS

| | | | |
|---|---|---|---|
| 5,302,400 A | 4/1994 | Sipos | 424/494 |
| 5,310,558 A | 5/1994 | Pozzi et al. | 424/476 |
| 5,316,772 A | 5/1994 | Jurgens, Jr. et al. | 424/472 |
| 5,330,761 A | 7/1994 | Baichwal | 424/469 |
| 5,334,372 A | 8/1994 | Kawamata et al. | 424/78.03 |
| 5,374,759 A | 12/1994 | Imperante et al. | 556/437 |
| 5,378,474 A | 1/1995 | Morella et al. | 424/469 |
| 5,395,626 A | 3/1995 | Kotwal et al. | 424/472 |
| 5,399,358 A | 3/1995 | Baichwal et al. | 424/464 |
| 5,399,359 A | 3/1995 | Baichwal | 424/464 |
| 5,399,362 A | 3/1995 | Baichwal et al. | 424/488 |
| 5,407,687 A | 4/1995 | Coffin et al. | 424/472 |
| 5,439,689 A | 8/1995 | Hendrickson et al. | 424/490 |
| 5,445,829 A | 8/1995 | Paradissis et al. | 424/480 |
| 5,455,046 A | 10/1995 | Baichwal | 424/457 |
| 5,464,633 A | 11/1995 | Conte et al. | 424/480 |
| 5,468,746 A | 11/1995 | Casagrande et al. | 514/235.5 |
| 5,472,708 A | 12/1995 | Chen | 424/451 |
| 5,472,711 A | 12/1995 | Baichwal | 424/468 |
| 5,478,574 A | 12/1995 | Baichwal et al. | 424/485 |
| 5,482,718 A | 1/1996 | Shah et al. | 424/480 |
| 5,500,227 A | 3/1996 | Oshlack et al. | 424/476 |
| 5,512,297 A | 4/1996 | Baichwal | 424/451 |
| 5,536,507 A | 7/1996 | Abramowitz et al. | 424/479 |
| 5,554,387 A | 9/1996 | Baichwal | 424/488 |
| 5,576,022 A | 11/1996 | Yang et al. | 424/472 |
| 5,585,114 A | 12/1996 | Besemer et al. | 424/488 |
| 5,612,053 A | 3/1997 | Baichwal et al. | 424/440 |
| 5,650,156 A | 7/1997 | Grinstaff et al. | 424/400 |
| 5,662,933 A | 9/1997 | Baichwal et al. | 424/457 |
| 5,667,801 A | 9/1997 | Baichwal | 424/457 |
| 5,670,168 A | 9/1997 | Baichwal et al. | 424/464 |
| 5,713,852 A | 2/1998 | Anthony et al. | 604/49 |
| 5,738,865 A | 4/1998 | Baichwal et al. | 424/440 |
| 5,773,025 A | 6/1998 | Baichwal | 424/458 |
| 5,788,987 A | 8/1998 | Busetti et al. | 424/480 |
| 5,792,476 A | 8/1998 | Hällgren | 424/465 |
| 5,811,388 A * | 9/1998 | Friend et al. | 514/2 |
| 5,837,284 A | 11/1998 | Mehta et al. | 424/459 |
| 5,840,329 A | 11/1998 | Bai | 424/458 |
| 5,846,563 A | 12/1998 | Baichwal | 424/457 |
| 5,858,412 A | 1/1999 | Staniforth et al. | 424/489 |
| 5,891,474 A | 4/1999 | Busetti et al. | 424/490 |
| 5,922,352 A | 7/1999 | Chen et al. | 424/465 |
| 5,958,456 A | 9/1999 | Baichwal et al. | 424/489 |
| 5,958,458 A | 9/1999 | Norling et al. | 424/490 |
| 5,958,873 A | 9/1999 | Sakr et al. | 514/2 |
| 6,024,982 A | 2/2000 | Oshlack et al. | 424/476 |
| 6,039,980 A | 3/2000 | Baichwal | 424/500 |
| 6,046,277 A * | 4/2000 | Kolter et al. | |
| 6,048,548 A | 4/2000 | Baichwal | 424/468 |
| 6,056,977 A | 5/2000 | Bhagwat et al. | 424/488 |
| 6,093,420 A | 7/2000 | Baichwal | 424/468 |
| 6,103,263 A | 8/2000 | Lee et al. | 424/468 |
| 6,136,343 A | 10/2000 | Baichwal | 424/468 |
| 6,146,662 A | 11/2000 | Jao et al. | 424/473 |
| 6,156,340 A | 12/2000 | Adeyeye et al. | 424/463 |
| 6,190,692 B1 * | 2/2001 | Busetti et al. | |
| 6,228,398 B1 * | 5/2001 | Devane et al. | |
| 6,245,355 B1 | 6/2001 | Baichwal | 424/468 |
| 6,245,356 B1 | 6/2001 | Baichwal | 424/468 |
| 6,261,601 B1 | 7/2001 | Talwar et al. | 424/469 |
| 6,299,903 B1 | 10/2001 | Rivett et al. | 424/464 |
| 6,322,819 B1 | 11/2001 | Burnside et al. | 424/494 |
| 6,358,525 B1 | 3/2002 | Guo et al. | 424/464 |
| 6,372,254 B1 | 4/2002 | Ting et al. | 424/473 |
| 6,387,394 B1 | 5/2002 | Baichwal et al. | 424/440 |
| 6,500,459 B1 | 12/2002 | Chhabra et al. | 424/474 |

FOREIGN PATENT DOCUMENTS

| | | |
|---|---|---|
| EP | 0305918 A1 | 3/1989 |
| EP | 0305918 B1 | 3/1989 |
| EP | 0366621 A1 | 5/1990 |
| EP | 0453001 A1 | 10/1991 |
| EP | 0519099 | 12/1992 |
| EP | 0572942 A2 | 12/1993 |
| EP | 0572942 B2 | 12/1993 |
| EP | 0629398 | 12/1994 |
| EP | 0526862 | 2/1996 |
| EP | 0572942 | 4/1997 |
| EP | 1064938 A1 | 1/2001 |
| WO | 9116042 | 10/1991 |
| WO | 9826767 | 6/1998 |
| WO | 9832425 | 7/1998 |
| WO | 9832426 | 7/1998 |
| WO | 0054780 | 9/2000 |
| WO | 0143749 | 6/2001 |
| WO | 0174334 | 10/2001 |

OTHER PUBLICATIONS

Fukui, Eiji,; Uemura, Katsuji, ;Kobayashi, Masao; "Studies on Applicability of Press-Coated Tablets Using Hydroxypropylcellulose (HPC) in the Outer Shell For Timed Release Preparations", Journal of Controlled Release 68 (2000) 215-223.

Ross, Alistair C.; Chambers, Alan R.; Stevens, Howard N. E.; Johnson, James R., "A Novel Oral Probe Formulation: The Hydrophilic Sandwich (HS) Capsule", Dept. Of Pharmaceutical Sciences, University of Strathclyde, Glasgow G4 ONR, 2000.

McConville, Jason T., Florence, Alastair J., Stevens, Howard N.E., Ross, Alistair C., "Processing Induced Variability of Time-Delayed Delivery From a Pulsatile Capsule Device", Dept. Of Pharmaceutical Sciences, University of Strathclyde, Glasgow, G4 ONR, 2000.

Ross, Alistair C.; Stevens, Howard N.E.; MacRae, Ross J.; Walthier, Mathias, "The Influence of Tablet Erosion in Controlling Drug Rlease From a Time-Delayed Capsule Formulation", Dept. Of Pharmaceutical Sciences, University of Strathclyde, Glasgow G4 ONR; Pfizer Central Research, Sandwich, CT 13 9NJ, Kent, U.K., 1999.

Ross, Alistair C.; Stevens, Howard N.E.; MacRae, Ross J.; Walter, Mathias, "Time-Delayed Capsule Drug Delivery Sysytem Based on Programmable Erosion", Dept. Of Pharmaceutical Sciences, University of Strathclyde, Scotland. Pfizer Central Research, Sandwich, U.K., 2000.

Mitsuyuki, Matsuo; Nakamura, Chizuko; Arimori, Kazuhiko; Nakano, Masahiro, " Evaluation of Hydroxyethylcellulose as a Hydrophilic Swellable Material for Delayed Release Tablets", Dept. Of Pharmaceutical Services, Kumamoto University Hospital, Chem. Pharm. Bull. 43(2) 311-314 (1995).

Conte, Ubaldo; Maggi, Lauretta, "A Flexible Technology For The Linear, Pulsatile and Delayed Release of Drugs, Allowing for Easy Accomodation of Difficult in Vitro Targets", Dept. Of Pharmaceutical Chemistry, University of Pavia,*Journal of Controlled Release 64* (2000) 263-268.

Mitsuyuki, Matsuo; Arimori, Kazuhiko; Nakamura, Chizuko, Nakano, Masahiro,"Delayed-Release Tablets Using Hydroxyethylcellulose As a Gel-Forming Matrix", Dept. Of Pharmaceutical Services, Kumanoto University Hospital, *International Journal of Pharmaceutics 138* (1996) 225-235.

Ross, Alistair, C.; Macrae, Ross J.; Walther, Mathias; Stevens, Howard N.E., "Chronopharmaceutical Drug Delivery From a Pulsatile Capsule Device Based on Programmable Erosion", Dept. Of Pharmaceutical Sciences, University of Strathclyde, Glasgow and Pfizer Central Research, Sandwich, UK, *J. Pharm. Pharmacol.* (2000) 52: 903-909.

Sangalli, M.E..; Maroni, A.; Busetti, C.; Zema, L.; Giordano, F.; Gazzaniga, "In Vitro and in Vivo Evaluation of Oral Sysytems For Time and Site Specific Delivery of Drugs (Chronotopic® technology)", Instituto Chimico Farmaceutico, Universita di Milano,*Boll. Chim. Farmaceutico-Anno 138—No. 3 Matzo* 1999, pp. 68-73.

Pillay, Viness; Fassihi, Reza, "In Situ Electrolyte Interactions in a Disk-Compressed Configuration System For Up-Curving and Constant Drug Delivery", Dept. Of Pharmaceutical Sciences, School of Pharmacy, Temple University, *Jouranl of Controlled release 67* (2000) 55-65.

Kenyon, C.J.; Nardi, R.V.; Wong, D., Hooper, G.; Wilding, I.R.; Friend D.R., "Colonic Delivery of Dexamethasone: A Pharmacoscintigraphic Evaluation", *Aliment Pharmacol Ther 1997*: 11:205-213.

ABSTRACT: El-Glbaly, Ibrahim, "Oral Delayed System based On Z-Pectinate Gel (ZPG) Microparticles As An Alternatecarrier to Calcium Pectinate Beads For Colonic Drug Delivery", *International Journal of Pharmaceutics* (*Kidlington*) vol. 232 No. 1-2, Jan. 31, 2002, pp. 199-211.

Nishimura, Kenji et al. "Dosage Form Design for Improvement of Bioavailablity of Levodopa VI: Formulation of Effervescent Enteric-Coated Tablets", Journal of American Pharmaceutical Sciences, vol. 73, No. 7, Jul. 1984, pp. 942-946.

Gazzaniga, A., et al. "Time-Dependent oral delivery systems for colon targeting", S.T.P. Pharma Sciences 5 (1), 1995, pp. 83-88.

Khan, M.Z.; "Recent Trends and Progress in Sustained or Controlled Oral Delivery of Some Water Soluble Drugs: Morphine Salts, Dilitiazem and Captopril" Drug Development and Industrial Pharmacy, 21(9), pp. 1037-1070 (1995).

EP Supplementary Search Report for European Application No. 02721430.3, (2004).

Supplemental European Search Report for European Application No. 02709836.7, (2004).

* cited by examiner

CHRONOTHERAPEUTIC DOSAGE FORMS AND METHODS OF TREATMENT USING CHRONOTHERAPY

This application is a continuation of U.S. patent application Ser. No. 10/099,461, filed Mar. 13, 2002 now abandoned, which claims priority from U.S. Provisional Application Ser. No. 60/275,382, filed Mar. 13, 2001, the disclosure of which is hereby incorporated by reference.

FIELD OF THE INVENTION

The present invention relates to a chronotherapeutic dosage form containing a therapeutically effective amount of a drug. The present invention is further related to methods of preparing such formulations, and to methods of treatment utilizing such formulations.

BACKGROUND OF THE INVENTION

Coordinating biological rhythms (chronobiology) with medical treatment is called chronotherapy. Chronotherapy takes into consideration a person's biological rhythms in determining the timing—and sometimes the amount—of medication to optimize desired effects of a drug(s) and minimize the undesired effects. The synchronization of medication levels to the biological rhythms of disease activity is playing an increasing role in the management of common cardiovascular conditions such as hypertension, elevated cholesterol, angina, stroke and ischemic heart disease, according to experts in this new and ever-expanding field. For example, in humans, at 1 am post-surgical death is most likely; at 2 am peptic ulcers flare up; at 3 am blood pressure bottoms out; at 4 am asthma is at its worst. When one wakes up, hay fever is at its most tormenting, and in the morning hours, as ones blood pressure rises to meet the day, one is most likely to suffer a heart attack or stroke. Rheumatoid arthritis improves through the day, but osteoarthritis grows worse. Alcohol is least toxic to the body at around 5 pm: cocktail hour.

The first application of chronotherapy, in the 1960s, was a synthetic corticosteroid tablet (Medrol, Upjohn). Clinicians found that when used in the morning, the drug was more effective and caused fewer adverse reactions. Another example of a commercial product employing chronotherapy is the bronchodilator, Uniphyl®, a long-acting theophylline preparation manufactured by Purdue Frederick (approved by the FDA in 1989). Taken once a day at dinner to control night-time asthma symptoms. Uniphyl® causes theophylline blood levels to reach their peak and improve lung function during the difficult morning hours.

Oral controlled release delivery systems may also be capable of passing over the entire tract of the small intestine, including the duodenum, jejunum, and ileum, so that the active ingredients can be released directly in the colon, if such site specific delivery is desired. One means of accomplishing this is by providing a coating surrounding the active pharmaceutical formulation core so as to preserve the integrity of the formulation while it is passing through the gastric tract. The high acidity of the gastric tract and presence of proteolytic and other enzymes therein generates a highly digestive environment that readily disintegrates pharmaceutical formulations that do not possess some type of gastro-resistance protection. This disintegration would typically have a detrimental effect upon the sustained release of the active agent. Such coated pharmaceutical formulations, in addition to slowing the release rate of the active agent contained within the core of the tablet, can also effectuate a delay in the release of the active ingredient for a desired period of time such that the dissolution of the active drug core can be delayed. Examples of coated pharmaceutical delivery systems for delayed release can be found in U.S. Pat. No. 4,863,742 (Panoz et al.) and U.S. Pat. No. 5,891,474 (Busetti et al.), as well as in European Patent Applications Nos. 366 621, 572 942 and 629 398. In the delayed release tablets described in each of these references, the therapeutically active drug core is coated with at least one and potentially several layers of coating, wherein the layers of coating have a direct effect upon the timed release of the active drug within the tablet core into the system of the patient.

It is considered desirable by those skilled in the art to provide an oral controlled release delivery system that is adaptable to deliver a drug(s) such that release rates and drug plasma profiles can be matched to physiological and chronotherapeutic requirements.

OBJECTS AND SUMMARY OF THE INVENTION

It is an object of the present invention to provide an oral pharmaceutical dosage form that releases a drug(s) into the body of a patient at a predetermined time after oral ingestion of the dosage form by the patient.

It is a further object of the present invention to provide an oral pharmaceutical dosage form that provides a delayed release of a drug(s) into the gastrointestinal tract of a patient at a predetermined time after oral ingestion of the dosage form.

It is a further object of certain embodiments of the present invention to provide an oral pharmaceutical dosage form having a core containing drug, the core being compression coated with a coating that provides a delayed release of the drug from the dosage form after the dosage form is orally administered to a patient.

It is a further object of certain embodiments of the present invention to provide an oral pharmaceutical dosage form having a drug-containing core that is compression coated with a coating which provides a delayed release of the drug when the dosage form is orally administered to a patient.

It is a further object of certain embodiments of the present invention to provide a dosage form which allows time-specific dosing for a wide variety of diseases.

It is a further object of certain embodiments of the present invention to provide a dosage form which allows time-specific dosing for diseases such as arthritis, high blood pressure, or asthma which are typically more symptomatic in the early morning corresponding to circadian rhythms.

It is a further object of certain embodiments of the present invention to provide a dosage form which provides a delayed release of drug from the dosage form, followed by a sustained release of the drug thereafter as the dosage form travels through the gastrointestinal tract.

It is a further object of certain embodiments of the present invention to provide a compression coated dosage form having an immediate release layer of a drug(s) overcoating a compression coated core which provides a delayed release of the same or different drug(s) from the dosage form; the core optionally providing a sustained release of the drug thereafter as the dosage form travels through the gastrointestinal tract.

It is a further object of certain embodiments of the present invention to provide an oral dosage form which provides site-specific delivery of drug (e.g., to the colon).

It is a further object of certain embodiments of the present invention to develop an oral dosage form which provides programmed release of drug.

It is a further object of certain embodiments of the present invention to develop an oral dosage form which provides pulsatile release of drug.

In accordance with the above-mentioned objects of the invention, the present invention is directed in part to an oral dosage form which comprises a core comprising a therapeutically effective amount of a drug, and a compression coating material applied to the core, the compression coating material including a delayed release material comprising one or more natural or synthetic gums which are compression coated onto the surface of the core such that the release of drug from the dosage form is delayed for a desired time period after oral administration of the dosage form to a mammal (e.g., human patient).

In certain preferred embodiments, the compression coating comprises a mixture (e.g., matrix) of xanthan gum, locust bean gum, and a pharmaceutically acceptable saccharide, e.g., a monosaccharide, a disaccharide, a polyhydric alcohol, or a combination of any of the foregoing. In certain preferred embodiments, the core is an immediate release core comprising the drug together with one or more pharmaceutically acceptable excipients.

The invention is further directed in part to a delayed release oral solid dosage form comprising a core comprising a therapeutically effective amount of a drug(s), and a delayed release material compression coated onto said core, the delayed release material comprising one or more natural or synthetic gums, the compression coating delaying the release of said drug from said dosage form for a period of time from about 2 to about 18 hours after exposure of the dosage form to an aqueous solution.

The invention is further directed in part to a delayed release oral solid dosage form comprising a core comprising a therapeutically effective amount of a drug(s), and an agglomerated delayed release material compression coated onto the core, the agglomerated delayed release material comprising a gum selected from, e.g., a homopolysaccharide, a heteropolysaccharide, and a mixture of a homopolysaccharide and a heteropolysaccharide, together with a pharmaceutically acceptable excipient, the compression coating delaying the release of the drug from the dosage form for a predetermined period of time after exposure of the dosage form to an aqueous solution.

The invention is further directed in part to a delayed release oral solid dosage form comprising a core comprising a therapeutically effective amount of a drug(s) and a disintegrant, and a delayed release material compression coated onto the core, said delayed release material comprising one or more natural or synthetic gums, said compression coating delaying the release of the drug from the dosage form for a predetermined period of time after exposure of the dosage form to an aqueous solution, the disintegrant being included in the core in an amount effective to cause the release of at least about 50 percent of the drug into said aqueous solution within one hour after said predetermined period of time.

The invention is further directed in part to a delayed release oral solid tablet, comprising a tablet core comprising a therapeutically effective amount of a drug, and a delayed release material compression coated onto the core, the delayed release material comprising one or more natural or synthetic gums, the gums comprising from about 6.5 percent to about 83 percent of the tablet by weight, the compression coating delaying the release of the drug from the dosage form for a period of time from about 2 to about 18 hours after exposure of the dosage form to an aqueous solution.

The invention is further directed to a chronotherapeutic, delayed release oral solid dosage form for low dose drugs, comprising a core comprising from about 0.01 mg to about 40 mg of a drug(s), and a delayed release material compression coated onto the core, the delayed release material comprising one or more natural or synthetic gums, the compression coating comprising from about 75 to about 94 percent by weight of the oral solid dosage form, and the ratio of the core to gum in the compression coating being from about 1:0.37 to about 1:5, by weight, the compression coating delaying the release of the drug from the dosage form for a period of time from about 2 to about 18 hours after exposure of the dosage form to an aqueous solution.

The invention is further directed in part to a chronotherapeutic, delayed release oral solid dosage form for a relatively high dose drug, comprising a core comprising from about 41 mg to about 300 mg of a drug, and a delayed release material compression coated onto the core, the delayed release material comprising one or more natural or synthetic gums, the ratio of the core to gum in the compression coating being from about 1:0.3 to about 1:3, by weight, the total weight of the oral solid dosage form being from about 500 mg to about 1500 mg, the compression coating delaying the release of the drug from the dosage form for a period of time from about 2 to about 18 hours after exposure of the dosage form to an aqueous solution.

The invention is further directed in part to a method of preparing a chronotherapeutic oral solid dosage form of a drug, comprising preparing a core comprising a therapeutically effective amount of a drug(s) and from about 5 to about 20% disintegrant, by weight of the core, preparing a granulate of a delayed release material comprising one or more natural or synthetic gums, compression coating the granulate onto said core, the compression coating delaying the release of the drug from the dosage form until after a period of time from about 2 to about 18 hours after exposure of the dosage form to an aqueous solution. In certain preferred embodiments, the method further comprises preparing the granulate of delayed release material by wet granulating one or more natural or synthetic gums together with at least one pharmaceutically acceptable excipient, and drying the resultant granulate to obtain agglomerated particles of the delayed release material. In certain embodiments the method further comprises granulating the glucocorticosteroid, the disintegrant, and a pharmaceutically acceptable inert diluent prior to the compression coating step.

In certain preferred embodiments, the disintegrant is a superdisintegrant incorporated in the core in an amount effective to cause the release of at least about 50 percent of the drug(s) into the aqueous solution within one hour upon completion of the time period for delayed release.

The invention is further directed to methods of treatment utilizing the formulations disclosed herein.

In certain embodiments, the oral dosage form provides a lag time (delayed release of drug) from about 2 to about 18 hours, after oral administration to, e.g., a human subject or patient.

In certain preferred embodiments, the oral dosage form releases at least about 50 percent of the drug(s) contained in the core within about one hour, and preferably at least about 80 percent of the drug(s) contained in the core within about one or two hours, after the end of the lag time provided by the compression coating.

In certain embodiments, the oral dosage form of the invention provides a lag time from about 5 to about 8 hours with a full release by about 8 to about 12 hours, after oral administration, e.g., to a human patient.

In certain preferred embodiments, the oral dosage form provides a lag time of about 6 to about 7 hours with full release by about 8 to about 9 hours, after oral administration of the dosage form.

In certain other preferred embodiments, the oral dosage form provides a lag time of about 6 to about 7 hours, followed by full release of the drug by about 7 to about 8 hours after oral administration.

In yet other embodiments, the formulation provides a lag time from about 9 to about 12 hours, with full release by about 11 to about 13 hours after oral administration, preferably a lag time of about 10 to about 11 hours followed by full release at about 11 to about 12 hours after oral administration of the dosage form.

In yet other embodiments, the formulation provides a lag time of, e.g., about 3-12 hours, with full release of the drug from the dosage form within about 24 hours, or (alternatively) after 24 hours.

By "delayed release" it is meant for purposes of the present invention that the release of the drug is delayed and the drug contained in the dosage form is not substantially released from the formulation until after a certain period of time, e.g., such that the drug is not released into the bloodstream of the patient immediately upon ingestion by the patient of the tablet but rather only after a specific period of time, e.g., a 4 hour to a 9 hour delay. For purposes of the present invention, delayed release is synonymous with "timed delay" or a release of drug after a lag time, or a programmed release.

By "sustained release" it is meant for purposes of the present invention that, once the drug is released from the formulation, it is released at a controlled rate such that therapeutically beneficial blood levels (but below toxic levels) of the medicament are maintained over an extended period of time from the start of drug release, e.g., providing a release over a time period, e.g., from about 4 to about 24 hours from the point of drug release after the lag time, onward.

The term "environmental fluid" is meant for purposes of the present invention to encompass, e.g., an aqueous solution (e.g., an in-vitro dissolution bath) or gastrointestinal fluid.

The term USP apparatus type III used herein is described e.g., in the United States Pharmacopeia XXV (2002).

DETAILED DESCRIPTION OF THE INVENTION

The present invention may be employed to achieve the time-delayed release of a pharmaceutically active agent and in certain embodiments to provide a controlled-release pharmaceutical formulation for pharmaceutically active agents that are desirously delivered over a predetermined period of time. The formulations of the present invention provide the time-delayed release of a pharmaceutically active agent and may be useful for the treatment of conditions that are desirously treated through time-delayed pharmaceutical agent delivery mechanisms. For example, the formulations of the present invention are useful for the treatment of morning pathologies, i.e., conditions, diseases or other illnesses, such as arthritis, hypertension and asthma, the symptoms of which are generally more acute in the morning as the patient awakens from sleep. These conditions may be treated by administering the time-delayed release formulation according to the present invention to the patient prior to sleeping, such that the delivery of the pharmaceutically active agent is achieved at about the time the patient awakens, or preferably the pharmaceutically active agent has been delivered from the dosage form (and absorbed from the gastrointestinal tract) to an extent that it has achieved a therapeutic effect, thereby alleviating the symptoms of the morning pathology.

The formulations of the present invention comprise a core comprising an active agent and a compression coating over the core that comprises one or more natural or synthetic pharmaceutically acceptable gums. In certain especially preferred embodiments, the compression coating comprises a combination of a heteropolysaccharide gum (e.g., xanthan gum) and a homopolysaccharide gum (e.g., locust bean gum), together with a pharmaceutically acceptable saccharide (e.g., lactose, dextrose, mannitol, etc.). In certain preferred embodiments, the gum(s) are wet granulated together with the optional saccharide(s) to form agglomerated particles comprising a mixture of, e.g., xanthan gum, locust bean gum and dextrose.

The goal of the compression coating of the present invention is to delay the release of the active agent, for a predetermined period of time, referred to in the art as a "lag time." In certain embodiments, the release of the active agent is delayed for, or has a lag time of, about 2 to about 18 hours after administration of the dosage form.

The core comprising the active agent can be formulated for either immediate release or sustained release of the active agent. Formulations for both immediate release and sustained release of active agents are well known to those skilled in the art.

In the present invention, when the core comprising the active agent is formulated for immediate release, the core can be prepared by any suitable tableting technique known to those skilled in the art. For example, the pharmaceutically active agent may be admixed with excipient(s) and formed into a tablet core using a conventional tableting press or using conventional wet granulation techniques. According certain preferred embodiments of the present invention, ingredients for the core are dry blended in a V-blender and compressed on a rotary tablet press into tablet cores. Alternatively, in certain embodiments, the ingredients for the core can be wet granulated, dried and thereafter compressed into tablet cores. Preferably, the core should be compressed to a degree of hardness such that they do not chip or come apart during further processing, such as during the coating process. In certain embodiments, the cores can be compressed to 50 mg weight and 2 to 8, preferably 4 to 8, most preferably 4-5 kP hardness. In addition, tablet core size should range from 1/8 inch to 5/8 inch, preferably from 1/8 inch to 1/2 inch, more preferably from 3/16 inch to 1/4 inch.

In certain embodiments, wherein the core is manufactured without a wet granulation step, and the final mixture is to be compressed into a tablet core, all or part of the excipient in the core may comprise a pre-manufactured direct compression diluent. Examples of such pre-manufactured direct compression diluents include Emcocel® (microcrystalline cellulose, N.F.), Emdex® (dextrates, N.F.), and Tab-Fine® (a number of direct-compression sugars including sucrose, fructose and dextrose), all of which are commercially available from Penwest Pharmaceuticals Co., Patterson, N.Y.). Other direct compression diluents include anhydrous lactose (Lactose N.F., anhydrous direct tableting) from Sheffield Chemical, Union, N.J. 07083; Elcems® G-250 (powdered cellulose), N.F.) from Degussa, D-600 Frankfurt (Main) Germany; Fast-Flo Lactose® (Lactose, N.F., spray dried) from Foremost Whey Products, Banaboo, Wis. 53913; Maltrin® (Agglomerated maltodextrin) from Grain Processing Corp., Muscatine, Iowa 52761; Neosorb 60® (Sorbitol, N.F., direct-compression from Roquet Corp., 645 5th Ave., New York, N.Y. 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel®

(Sodium starch glycolate, N.F., carboxymethyl starch) from Generichem Corp., Little Falls, N.J. 07424; Solka Floc® (Cellulose floc) from Penwest Pharmaceuticals Co., Patterson, N.Y. 10512; Spray-Dried Lactose® (Lactose N.F., spray dried) from Foremost Whey Products, Baraboo, Wis. 53913 and DMV Corp., Vehgel, Holland; and Sta-Rx 1500® (Starch 1500) (Pregelatinized starch, N.F., compressible) from Colorcon, Inc., West Point, Pa. 19486. In certain embodiments of the present invention, the directly compressible inert diluent which is used in the core of the present invention is an augmented microcrystalline cellulose as disclosed in U.S. Pat. No. 5,585,115, issued Dec. 17, 1996, and entitled "PHARMACEUTICAL EXCIPIENT HAVING IMPROVED COMPRESSIBILITY", hereby incorporated by reference in its entirety. The augmented microcrystalline cellulose described therein is commercially available under the tradename Prosolv® from Penwest Pharmaceuticals Co. PROSOLV SMCC 50 is a silicified microcrystalline cellulose. This particular grade has a median particle size (by sieve analysis) in the region of 50 µm. PROSOLV SMCC 90 is a silicified microcrystalline cellulose. This grade has a median particle size (by sieve analysis) in the region of 90 µm.

Alternatively, in certain embodiments, the core comprising the active agent can be formulated as a sustained release core for the sustained release of the active agent. When the core comprising the active agent is formulated for sustained release, the core can be prepared in a number of ways known in the art. For example, the active agent can be incorporated in a sustained release matrix and thereafter compressed into a core, or a sustained release material can be coated onto the immediate release core to provide for the sustained release of the active agent, or a combination of the compressed sustained release matrix and sustained release coating on the core can be used. Additionally, spheroids comprising the active agent, or multiparticulates with sustained release coatings and comprising the active agent, may be compressed with optional binders and other excipients into a sustained release core.

When the core of the present invention comprises a sustained release matrix, the matrix formulations are generally prepared using standard techniques well known in the art. Typically, they are prepared by dry blending a sustained release material, diluent, active agent, and optional other excipients followed by granulating the mixture until proper granulation is obtained. The granulation is done by methods known in the art. Typically with a wet granulation, the wet granules are dried in a fluid bed dryer, sifted and ground to appropriate size. Lubricating agents are mixed with the dried granulation to obtain the final core formulation.

In our U.S. Pat. Nos. 4,994,276; 5,128,143; 5,135,757; 5,455,046; 5,512,297; 5,554,387; 5,667,801; 5,846,563; 5,773,025; 6,048,548; 5,662,933; 5,958,456; 5,472,711; 5,670,168; and 6,039,980, all of which are hereby incorporated by reference, we reported that a controlled release excipient that is comprised of a gelling agent such as synergistic heterodisperse polysaccharides (e.g., a heteropolysaccharide such as xanthan gum) preferably in combination with a polysaccharide gum capable of cross-linking with the heteropolysaccharide (e.g., locust bean gum) is capable of processing into oral solid dosage forms using either direct compression, following addition of drug and lubricant powder, conventional wet granulation, or a combination of the two. These systems (controlled release excipients) are commercially available under the trade name TIMERx® from Penwest Pharmaceuticals Co., Patterson, N.Y., which is the assignee of the present invention.

In certain embodiments of the present invention, wherein the core provides for the sustained release of the active agent, the core comprises a sustained release matrix such as those disclosed in our foregoing patents. For example, in certain embodiments of the present invention, in addition to the active agent, the core comprises a sustained release excipient comprising a gelling agent comprising a heteropolysaccharide gum and a homopolysaccharide gum capable of cross-linking said heteropolysaccharide gum when exposed to an environmental fluid, and an inert pharmaceutical diluent. Preferably, the ratio of the heteropolysaccharide gum to the homopolysaccharide gum is from about 1:3 to about 3:1, and the ratio of active agent to gelling agent is preferably from about 1:3 to about 1:8. The resulting core preferably provides a therapeutically effective blood level of the active agent for at least about 4 hours, and in certain preferred embodiments, for about 24 hours. In certain preferred embodiments, the sustained release excipient further comprises an effective amount of a pharmaceutically acceptable ionizable gel strength enhancing agent, such as those described hereinafter, to provide a sustained release of the active when the core is exposed to an environmental fluid. The sustained release excipient (with or without the optional ionizable gel strength enhancing agent) may be further modified by incorporation of a hydrophobic material which slows the hydration of the gums without disrupting the hydrophilic matrix. In addition, in certain embodiments, the sustained release excipient can be modified to provide for bi- or multi-phasic release profiles of the active agent by the inclusion of a pharmaceutically acceptable surfactant or wetting agent in the core. Alternatively, the sustained release excipient comprises only one of the aforementioned gums. In yet other embodiments, the sustained release excipient comprises a different pharmaceutically acceptable gum.

In addition to the above, other sustained release materials may be used for the sustained release matrix cores of the inventive formulations. A non-limiting list of suitable sustained-release materials which may be included in a sustained-release matrix according to the present invention include hydrophilic and/or hydrophobic materials, such as sustained release polymers gums, acrylic resins, protein derived materials, waxes, shellac, and oils such as hydrogenated castor oil, hydrogenated vegetable oil. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred waxes include for example natural and synthetic waxes, fatty acids, fatty alcohols, and mixtures of the same (e.g., beeswax, carnauba wax, stearic acid and stearyl alcohol). Certain embodiments utilize mixtures of any of the foregoing sustained release materials in the matrix of the core. However, any pharmaceutically acceptable hydrophobic or hydrophilic sustained-release material which is capable of imparting sustained-release of the active agent may be used in accordance with the present invention.

Alternatively, in certain embodiments of the present invention, the core may be formulated to provide for the sustained release of the active agent through the use of an immediate release core (as previously described) with a sufficient amount of a hydrophobic coating to provide for the sustained release of the active agent from the immediate release core. The hydrophobic coating may be applied to the core using methods and techniques known to those skilled in the art. Examples of suitable coating devices include fluid bed coaters, pan coaters, etc. Examples of hydrophobic materials which may be used in such hydrophobic coatings include for example, alkylcelluloses (e.g., ethylcellulose), copolymers of acrylic and methacrylic acid esters, waxes, shellac, zein, hydrogenated vegetable oil, mixtures thereof, and the like.

Additionally, the cores may be formulated for sustained release of the active agent by using a combination of the sustained release matrix and sustained release coating. The sustained release cores (e.g, sustained release matrix, sustained release coated, or combination thereof), and the immediate release cores, may also contain suitable quantities of additional excipients, e.g., lubricants, binders, granulating aids, diluents, colorants, flavorants and glidants which are conventional in the pharmaceutical art.

Specific examples of pharmaceutically acceptable diluents and excipients that may be used in formulating the cores are described in the *Handbook of Pharmaceutical Excipients*, American Pharmaceutical Association (1986), incorporated by reference herein.

In certain preferred embodiments, the oral dosage form includes one or more disintegrants preferably incorporated in the core. When such an agent is included in the core, the rate of release of drug (after the initial delay caused by the compression coating) is an immediate pulse effect. In certain embodiments, when no disintegrant is present, a controlled profile may be produced. Suitable disintegrants are known to those skilled in the art, and include for example sodium starch glycolate (commercially available as Explotab® from Penwest Pharmaceuticals Co.).

The mechanism of disintegration is based on swelling, wicking, and deformation of the disintegrants. When a compressed tablet is placed in aqueous solution, water can be quickly absorbed, and the swelling of the disintegrant breaks apart tablets quickly. In one embodiment in which the therapeutic active drug is formulated for immediate release, when a disintegrant is present in the core of the tablet, the rate of release of the active agent is an immediate pulse effect. In certain embodiments in which the therapeutic active drug is formulated for immediate release, when no disintegrant is present, a controlled profile may be produced.

Examples of such disintegrants for use in the present invention include, for example, starch, veegum, crospovidone, cellulose, kaolin, microcrystalline cellulose (e.g., Avicel PH101 & PH102), crosslinked polyvinyl pyrrolidone (e.g., Kollidon CL), and mixtures thereof. In certain preferred embodiments, the disintegrant is a superdisintegrant, such as, for example, croscarmellose sodium, crospovidone, crosslinked carboxy methyl cellulose, sodium starch glycolate, and mixtures thereof. Superdisintegrants can be incorporated at lower levels than regular disintegrants to increase the water content. Some brand named superdisintegrants for use in the present invention include, Ac-Di-Sol®, Primojel®, Explotab®, and Crospovidone®.

In certain embodiments, the core of the present invention includes a wicking agent in addition to or as an alternative to a disintegrant. Wicking agents such as those materials already mentioned as disintegrants (e.g. microcrystalline cellulose) may be included if necessary to enhance the speed of water uptake. Other materials suitable for acting as wicking agents include, but are not limited to, colloidal silicon dioxide, kaolin, titanium dioxide, fumed silicon dioxide, alumina, niacinamide, sodium lauryl sulfate, low molecular weight polyvinyl pyrrolidone, m-pyrol, bentonite, magnesium aluminum silicate, polyester, polyethylene, mixtures thereof, and the like.

In certain embodiments, the one or more disintegrant(s) in the core is included in an amount from about 5 to about 20 percent, preferably from about 6 to about 10 percent, most preferably about 8 percent by weight of the core. In terms of whole tablet weight (e.g., core plus compression coating), the one or more disintegrant(s) in the core are included in an amount from about 0.1 to about 5 percent, preferably from about 0.3 to about 2 percent, by weight of the tablet (entire formulation).

According to the present invention, the core containing active drug is completely surrounded or substantially surrounded by a compression coating. The compression coating preferably delays the release of the pharmaceutically active agent for a predetermined period of time, which time is dependent upon the formulation of the coating and the thickness of the coating layer. The appropriate time period for the release of the active ingredient can be determined prior to the preparation of the formulation, and the formulation can be designed by applying the appropriate thickness and composition of the coating to achieve the desired time delay prior to release of the active ingredient and the desired release rate of the active ingredient following the time delay.

Preferably, the compression coating comprises a natural or synthetic gum which can function as a gelling agent, causing the core to be surrounded by the gel when the compression coated tablet is exposed to an environmental fluid (e.g., water or gastrointestinal fluid) and thereby causing the drug to be released after diffusion of the environmental fluid through the compression coating, the dissolution of the drug into the environmental fluid, and the egress of the dissolved drug into the fluid surrounding the compression coated tablet.

In certain embodiments, gums for use in the compression coating include, for example and without limitation, heteropolysaccharides such as xanthan gum(s), homopolysaccharides such as locust bean gum, galactans, mannans, vegetable gums such as alginates, gum karaya, pectin, agar, tragacanth, accacia, carrageenan, tragacanth, chitosan, agar, alginic acid, other polysaccharide gums (e.g. hydrocolloids), and mixtures of any of the foregoing. Further examples of specific gums which may be useful in the compression coatings of the invention include but are not limited to acacia catechu, salai guggal, indian bodellum, copaiba gum, asafetida, cambi gum, *Enterolobium cyclocarpum*, mastic gum, benzoin gum, sandarac, gambier gum, butea frondosa (Flame of Forest Gum), myrrh, konjak mannan, guar gum, welan gum, gellan gum, tara gum, locust bean gum, carageenan gum, glucomannan, galactan gum, sodium alginate, tragacanth, chitosan, xanthan gum, deacetylated xanthan gum, pectin, sodium polypectate, gluten, karaya gum, tamarind gum, ghatti gum, Accaroid/Yacca/Red gum, dammar gum, juniper gum, ester gum, ipil-ipil seed gum, gum talha (acacia seyal), and cultured plant cell gums including those of the plants of the genera: acacia, actinidia, aptenia, carbobrotus, chickorium, cucumis, glycine, hibiscus, hordeum, letuca, lycopersicon, malus, medicago, mesembryanthemum, oryza, panicum, phalaris, phleum, poliathus, polycarbophil, sida, solanum, trifolium, trigonella, Afzelia africana seed gum, *Treculia africana* gum, detarium gum, cassia gum, carob gum, *Prosopis africana* gum, *Colocassia esulenta* gum, *Hakea gibbosa* gum, khaya gum, scleroglucan, zea, mixtures of any of the foregoing, and the like.

In certain especially preferred embodiments, the compression coating comprises a heteropolysaccharide such as xanthan gum, a homopolysaccharide such as locust bean gum, or a mixture of one or more hetero- and one or more homopolysaccharide(s). Heterodisperse excipients, previously disclosed as a sustained release tablet matrix in our U.S. Pat. Nos. 4,994,276, 5,128,143, and 5,135,757, may be utilized in the compression coatings of the present invention. For example, in certain embodiments of the present invention, a gelling agent of both hetero- and homo-polysaccharides which exhibit synergism, e.g., the combination of two or more polysaccharide gums producing a higher viscosity and faster hydration than that which would be expected by either of the gums alone, the resultant gel being faster-forming and more rigid, may be used in the compression coatings of the present invention.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharide materials used in the present invention that are capable of cross-linking with the heteropolysaccharide include the galactomannans, i.e., polysaccharides that are composed solely of mannose and galactose. A possible mechanism for the interaction between the galactomannan and the heteropolysaccharide involves the interaction between the helical regions of the heteropolysaccharide and the unsubstituted mannose regions of the galactomannan. Galactomannans that have higher proportions of unsubstituted mannose regions have been found to achieve more interaction with the heteropolysaccharide. Hence, locust bean gum, which has a higher ratio of mannose to galactose, is especially preferred as compared to other galactomannans, such as guar and hydroxypropyl guar.

In certain preferred embodiments, the heteropolysaccharide comprises from about 1 to about 50 percent and the homopolysaccharide material comprises from about 50 to about 1 percent by weight of the compression coating. In certain preferred embodiments, the ratio of heteropolysaccharide to homopolysaccharide material is from about 1:3 to 3:1, preferably from about 2:3 to 3:2, or 1:1.

In a certain preferred embodiment, the compression coating comprises from about 5 to about 70 percent or more by weight of a hydrophilic material (e.g., gums). In certain preferred embodiments of the present invention, the higher the percentage of gums in the compression coating, the longer the delay of the release or "lag time" of the active agent.

In certain embodiments, the percent of gums in the compression coating corresponds to a delayed release of the active agent which is independent of pH. For example, in certain preferred embodiments, when the compression coating is less than about 25% gums, preferably comprising about 5 to about 15% gums, the delayed release is more independent of pH than a compression coating comprising greater than about 25% gums (e.g., 30, 40, or 50% gums).

In certain preferred embodiments, the compression coating also includes pharmaceutically acceptable excipients, for example, a saccharide such as a monosaccharide, a disaccharide or a polyhydric alcohol, and/or mixtures of any of the foregoing, or microcrystalline cellulose or a starch. Examples of suitable such excipients include sucrose, dextrose, lactose, fructose, xylitol, sorbitol, mannitol, starches, mixtures thereof and the like. In certain embodiments, it is preferred that a soluble pharmaceutical excipient such as lactose, dextrose, sucrose, mannitol, or mixtures thereof is included in the materials to be used in the compression coating. In certain preferred embodiments, the gum(s) is wet granulated with the pharmaceutically acceptable excipient prior to its use as a compression coating on the surface of the inner cores of the invention. The compression coating may comprise, e.g., up to about 95% pharmaceutically acceptable excipient(s), by weight.

In certain embodiments, the amount of gum(s) contained in the compression coating is from about 1 percent to about 90 percent by weight, preferably from about 6.5 percent to about 83 percent of the total tablet, by weight.

In certain embodiments, it is possible to dry mix the ingredients of the compression (delayed release) coating without utilizing a wet granulation step. If the mixture is to be manufactured without a wet granulation step, and the final mixture is to be compression coated onto a pre-formed tablet core, it is preferred that all or part of the pharmaceutically acceptable excipient(s) should impart sufficient compressibility to provide a pharmaceutically acceptable product. The properties and characteristics of a specific excipient system prepared according to the present invention may be dependent in part on the individual characteristics, e.g., of the homo- and heteropolysaccharide constituents, in terms of polymer solubility, glass transition temperatures etc., as well as on the synergism both between different homo- and heteropolysaccharides and between the homo- and heteropolysaccharides and the inert saccharide constituent(s) in modifying dissolution fluid-excipient interactions.

In certain embodiments of the invention where the compression coating comprises a heteropolysaccharide, a homopolysaccharide, or both, a release-modifying agent as described in our previous patents directed to the use of these materials in sustained release matrices can also be utilized in the compression coating. Such release-modifying agents and pre-manufactured excipients disclosed in our U.S. Pat. Nos. 5,455,046; 5,512,297; 5,554,387; 5,667,801; 5,846,563; 5,773,025; 6,048,548; 5,662,933; 5,958,456; 5,472,711; 5,670,168; and 6,039,980 may be utilized in the compression coatings of the present invention.

Thus, for example, the release-modifying agent may comprise an ionizable gel-strength enhancing agent. The ionizable gel strength-enhancing agent that is optionally used in conjunction with the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable ionizable gel strength enhancing agent include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred ionizable gel strength-enhancing agents are bivalent. Particularly preferred salts are calcium sulfate and sodium chloride. The ionizable gel strength enhancing agents of the present invention are added in an amount effective to obtain a desirable increased gel strength due to the cross-linking of the gelling agent (e.g., the heteropolysaccharide and homopolysaccharide gums). In alternate embodiments, the ionizable gel strength-enhancing agent is included in the delayed release excipient of the present invention in an amount from about 1 to about 20% by weight of the delayed release excipient, and in an amount 0.5% to about 16% by weight of the final dosage form. In certain embodiments, the inclusion of an ionizable gel strength-enhancing agent not only delays the release of the active, but also provides for a sustained release of the active agent.

In certain embodiments of the present invention, the (delayed release) compression coating coated onto the core comprises from about 1 to about 90 percent by weight of a gelling agent comprising a heteropolysaccharide gum and a homopolysaccharide gum, from about 0 to about 20 percent by weight of an ionizable gel strength enhancing agent, and from about 10 to about 95 percent by weight of an pharmaceutically acceptable excipient. In other embodiments, the compression coating material comprises from about 5 to about 75 percent gelling agent (gum), from about 0 to about 15 percent ionizable gel strength enhancing agent, and from about 30 to about 95 percent pharmaceutically acceptable excipient (e.g., an inert diluent). In yet other embodiments, the compression coating material comprises from about 7.5 to about 50 percent gelling agent, from about 0 to about 10 percent ionizable gel strength enhancing agent, and from about 30 to about 95 percent pharmaceutically acceptable excipient.

Surfactants that may be used in the present invention generally include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoprionates.

Other suitable surfactants for use in conjunction with the present invention include polyethyleneglycols as esters or ethers. Examples include polyethoxylated castor oil, polyethoxylated hydrogenated castor oil, or polyethoxylated fatty acid from castor oil or polyethoxylated fatty acid from hydrogenated castor oil. Commercially available surfactants that can be used are known under trade names Cremophor, Myrj, Polyoxyl 40 stearate, Emerest 2675, Lipal 395 and PEG 3350.

Other release-modifying pharmaceutically acceptable agents that may be added in appropriate quantities for their particular ability to modify dissolution rates include, for example: stearic acid, metallic stearates, stearyl alcohol, hydrogenated cotton seed oil, sodium chloride and certain disintegrants that are described below.

The quantity of such release-modifying agent employed depends on the release characteristics required and the nature of the agent. For a delayed release formulation according to the invention, the level of release-modifying agents used may be from about 0.1 to about 25%, preferably from about 0.5 to about 10% by weight of the total composition.

In certain other embodiments of the invention, the compression coating includes a pH-modifying agent. The pH-modifying agent may be present in the compression coating from about 1% to about 10% by weight of the final dosage form. In preferred embodiments, the pH-modifying agent is an organic acid such as citric acid, succinic acid, fumaric acid, malic acid, maleic acid, glutaric acid or lactic acid.

In certain preferred embodiments, the release of drug occurs when aqueous environmental fluid (e.g., water or gastrointestinal fluid, etc. surrounding the dosage form) diffuses through the compression coating of the dosage form, resulting in hydration of the core and dissolving the drug, which then can pass into the fluid surrounding the core.

In certain preferred embodiments, the delayed release of the drug (lag time) is varied by increasing the thickness of the compression coating (increased lag time) or by decreasing the thickness of the compressing coating (decreased lag time). The delayed release may also be varied, e.g., by changing the gum(s) included in the delayed release compression coating, selecting a particular combination of gums, by including or not including a pharmaceutically acceptable excipient, such as a saccharide (including polysaccharides) or a combination of saccharide(s) (or polysaccharides) in the compression coating, by changing or by adding additional agents to the compression coating which cause the compression coating to further delay the diffusion of water (or gastrointestinal fluid) through the compression coating (e.g., matrix) into the inner core (thereby allowing hydration of the inner core). In addition, the compression force used to apply the compression coating may be used to alter the release rate of the active ingredient. Also, release can be modified via the use of an extragranular excipient addition to the compression coating. Such ingredients may comprise, for example, microcrystalline cellulose, polyvinylpyrrolidone, polyethylene glycol, and the like.

The delayed release of the drug may further be varied by utilizing a further coating (i) between the core and the compression coating; (ii) over the compression coating; or (iii) both between the core and the compression coating and over the compression coating. Such coatings may comprise, for example a hydrophilic polymer (such as hydroxypropylmethylcellulose) and/or a hydrophobic polymer (such as an acrylic polymer, a copolymer of acrylic and methacrylic acid esters, an alkylcellulose such as ethylcellulose, etc.). In such circumstances, the release of drug from the dosage form may not only be occurring as fluid diffuses through the compression coating; erosion of the further coatings described in this paragraph may also delay the release of drug.

The dissolution rates of the present invention (with or without the optional release modifying agents mentioned above) may be further modified by incorporation of a hydrophobic material in the compression coating, which slows the hydration of the gums without disrupting the hydrophilic matrix. This is accomplished in alternate embodiments of the present invention by granulating the delayed release excipient with a solution or dispersion of a hydrophobic material prior to the compression coating of the core. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The solvent for the hydrophobic material may be an aqueous or organic solvent, or mixtures thereof. The amount of hydrophobic material incorporated into the delayed release excipient is that which is effective to slow the hydration of the gums without disrupting the hydrophilic matrix formed upon exposure to an environmental fluid. In certain preferred embodiments of the present invention, the hydrophobic material is included in the compression coating in an amount from about 1 to about 20 percent by weight.

The compression coating may also contain suitable quantities of, e.g., lubricants, binders, granulating aids, diluents, colorants, flavorants and glidants which are described hereinafter and are which are conventional in the pharmaceutical art.

In preferred embodiments where the materials to be included in the compression coating are pre-manufactured, the combination of the gum gelling agent (e.g., a mixture of xanthan gum and locust bean gum) with the pharmaceutical excipient(s), with or without a release modifying agent, provides a ready-to-use compression coating product in which a formulator need only apply the material onto the core by compression coating to provide the desired chronotherapeutic dosage forms. The compression coating may comprise a physical admix of the gums along with a soluble excipient such as compressible sucrose, lactose, dextrose, etc., although it is preferred to granulate or agglomerate the gums with a plain pharmaceutically acceptable excipient (i.e., crystalline) sucrose, lactose, dextrose, mannitol, etc., to form a delayed release excipient for use in the compression coating. The granulate form has certain advantages including the fact that it can be optimized for flow and compressibility.

The gums and optional pharmaceutical excipients used in the compression coating are preferably prepared according to any agglomeration technique to yield an acceptable excipient product. In wet granulation techniques, the desired amounts of the hydrophilic material (e.g., heteropolysaccharide gum and/or the homopolysaccharide gum) and the inert diluent are mixed together and thereafter a moistening agent such as water, propylene glycol, glycerol, alcohol or the like is added to prepare a moistened mass. Next, the moistened mass is dried. The dried mass is then milled with conventional equipment into granules. Thereafter, the excipient product is ready to use.

The (preferably) pre-manufactured delayed release excipient is preferably free-flowing and directly compressible. Accordingly, the excipient may be directly compressed onto a pre-formed inner core of a therapeutically active medicament to form coated tablets. The delayed release coating mixture, in an amount sufficient to make a uniform coating onto a pre-formed tablet core, is subjected to tableting in a conventional production scale tableting machine at normal compression pressure, i.e., about 2000-1600 lbs/sq in. However, the mixture should not be compressed to such a degree that there is subsequent difficulty in its hydration when exposed to gastric fluid.

The average particle size of the granulated delayed release excipient of the present invention ranges from about 50 microns to about 400 microns and preferably from about 185 microns to about 265 microns. The particle size of the granulation is not narrowly critical, the important parameter being that the average particle size of the granules must permit the formation of a directly compressible excipient which forms a coating over pharmaceutically active tablet cores. The desired tap and bulk densities of the granulation of the present invention are normally between from about 0.3 to about 0.8 g/ml, with an average density of from about 0.5 to about 0.7 g/ml.

The compression coatings of the present invention preferably have uniform packing characteristics over a range of different particle size distributions and are capable of processing onto the pre-formed tablet core using direct compression, following the addition of a lubricant.

In addition to being (optionally) used in the tablet core, in certain embodiments it is preferred that one or more pharmaceutically acceptable lubricants be added to the compression coating materials (preferably pre-agglomerated) prior to the mixture being compression coated onto the surface of the core. Examples of suitable lubricants for use in the core and compression coating of the invention include, for example and without limitation, talc, stearic acid, vegetable oil, calcium stearate, zinc stearate, magnesium stearate, etc. Preferably, an effective amount of any generally accepted pharmaceutical lubricant, including calcium or magnesium soaps is preferably added to the mixture of ingredients prior to compression of the mixture onto the solid pre-formed tablet core. An especially preferred lubricant is sodium stearyl fumarate, NF, commercially available under the trade name Pruv® from Penwest Pharmaceuticals Co.

In certain embodiments, the present invention is further directed towards a method of manufacturing the delayed release solid oral dosage forms (e.g., tablets) of the present invention. In certain preferred embodiments, the steps for preparation of a delayed release oral solid dosage form of the present invention may include the following:

Preparation of Inner Core Formulation:
1. (A) Wet granulate active ingredient (e.g., drug) together with optional excipients, followed by drying and milling as necessary to obtain a granulate; or
   (B) Dry blend the active together with optional excipients using geometric dilution as necessary to obtain a granulate;
2. Optionally, extragranularly add excipients to the material prepared in Step 1 with appropriate blending;
3. Preferably, lubricate powder blend prepared in Step 1 or 2:
4. Compress core using powder blend prepared in Step 3 with an appropriate press.
5. Optionally, applying a functional film coating onto the tablet cores prepared in Step 4;

Preparation of Delayed Release (Compression) Coating May be Accomplished, e.g., as Follows:
6. (A) Wet granulate a gum(s) (e.g., a heteropolysaccharide gum and a homopolysaccharide gum) together with optional excipients to form a delayed release material (agglomerated particles), and then dry the delayed release material; or
   (B) Dry blend a gum(s) together with optional excipients to form a delayed release material (granulate);
7. Preferably, mill the delayed release material prepared in Step 6;
8. Preferably, lubricate the delayed release material prepared in Step 6 or 7;

Coating of Inner Core:
9. Compression coat the delayed release material prepared in Steps 6-8 over the tablet cores prepared in Step 1-5;
10. Optionally, film coat the final dosage form (if desired).

In certain embodiments, steps 4 & 10 are combined in a single unit operation when using e.g., a Dry-Cota Press as described hereinafter. A functional coating of the tablet cores may be possible using the Dry-Cota Press if a modification is made to the press to add a core tablet feeder system.

A Manesty Dry-Cota press press consists of two side by side interconnected tablet presses where the core is made on one press then mechanically transferred to the next press for compression coating. Each "press" has an independent powder feed mechanism so that core blend is loaded on one machine and coating blend on the other. Mechanical transfer arms rotate between the machines to remove cores from one press and transfer them to the coating press. Other and more modern types of presses which may be used (e.g. Elizabeth Hata HT-AP44-MSU-C, Killian RUD, Fette PT 4090) have a dual feed system for coating blend and pre-made cores. This configuration is more flexible, in that cores can be pan coated with a functional or cosmetic coating before compression coating. In addition, this allows multiple compression coating layers to be achieved by recycling tablets that have already been compression coated. Both types of presses have mechanisms to center the tablet within the coating both vertically and radially. One of ordinary skill would understand that other tablet presses may be used to provide for the final dosage forms of the present invention.

Although typically the compression coating surrounds the entire core, in certain embodiments of the present invention, the compression coating substantially surrounds, but does not entirely surround the tablet core. In such instances, the release of drug from the tablet core will occur first from that portion of the inner core to which the compression is not applied. In other embodiments of the invention, compression coating is not applied to the same thickness around the entire inner core, thereby creating areas of the compressed dosage form that release drug earlier (and later) than other areas. This may be accomplished, e.g, by having the core to which the compression coating is applied not being centered in the press.

For best results, the tablets formed from the compression coating of the core are from about 4 to about 25 kP, preferably about 5 to about 15 kP, most preferably about 8 to about 9 kP hardness. In certain preferred embodiments, for round compression coated tablets the diameter may be up to ⅝ inch or greater, and for caplet shaped compression coated tablets the diameter may be up to ¾ inch or greater. The average flow of the (non-compression) coatings prepared in accordance with the present invention is from about 25 to about 40 g/sec.

In certain embodiments of the present invention, the compression coated tablet may then be further overcoated with an enteric coating material or a hydrophobic material. Examples of suitable enteric polymers include cellulose acetate phthalate, hydroxypropyl-methylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit® L30D55.

In further embodiments, the dosage form may be coating with a hydrophilic coating in addition to or instead of the above-mentioned enteric coating or hydrophobic coating. An example of a suitable material that may be used for such a hydrophilic coating is hydroxypropylmethylcellulose (e.g., Opadry®, commercially available from Colorcon, West Point, Pa.).

In still further embodiments, the optional enteric and/or hydrophobic and/or hydrophilic coatings may be alternatively or additionally applied as an intermediate layer(s) between the core and the compression coating.

The optional enteric and/or hydrophobic and/or hydrophilic coatings may be applied in any pharmaceutically acceptable manner known to those skilled in the art. For example, in one embodiment, the coating is applied via a fluidized bed or in a coating pan. For example, the coated tablets may be dried, e.g., at about 60-70° C. for about 3-4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10μ if applied via spray-coating or immersion-coating. Generally, in embodiments of the invention wherein a hydrophobic polymer or enteric coating is applied to the tablets over the delayed release coating, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

As mentioned above, the cores and/or compression coatings may also contain suitable quantities of, e.g., lubricants, binders, granulating aids, diluents, colorants, flavorants and glidants which are conventional in the pharmaceutical art.

Examples of suitable binders for use in the present invention include for example and without limitation, povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Examples of suitable glidants for use in the present invention include talc, silicon dioxide, and cornstarch.

In certain embodiments of the present invention, the tablet core includes an additional dose of the drug (or a therapeutically effective dose of a different drug) included in either the (optional) hydrophobic or enteric coating, or in an additional (optional) overcoating coated on the outer surface of the tablet core (without the hydrophobic or enteric coating) or as an additional coating layer coated on the surface of the base coating(s) comprising the compression coating and, if applicable, hydrophobic and/or enteric coating material. This may be desired when, for example, a loading dose of the drug is needed to provide therapeutically effective blood levels of the active agent when the formulation is first exposed to gastric fluid. The loading dose of drug included in the coating layer may be, e.g., from about 10% to about 40% of the total amount of drug included in the formulation.

Examples of drugs that are suitable for incorporation in the present invention include:

antihistamines (e.g., azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride and triprolidine hydrochloride);

antibiotics (e.g., penicillin V potassium, cloxacillin sodium, dicloxacillin sodium, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate HCL, lincomycin HCL, novobiocin sodium, nitrofurantoin sodium, metronidazole hydrochloride); antituberculosis agents (e.g., isoniazid);

cholinergic agents (e.g., ambenonium chloride, bethanecol chloride, neostigmine bromide, pyridostigmine bromide);
antimuscarinics (e.g., anisotropine methylbromide, clidinium bromide, dicyclomine hydrochloride, glycopyrrolate, hexocyclium methylsulfate, homatropine methylbromide, hyoscyamine sulfate, methantheline bromide, hyoscine hydrobromide, oxyphenonium bromide, propantheline bromide, tridihexethyl chloride);
sympathomimetics (e.g., bitolterol mesylate, ephedrine, ephedrine hydrochloride, ephedrine sulphate, orciprenaline sulphate, phenylpropanolamine hydrochloride, pseudoephedrine hydrochloride, ritodrine hydrochloride, salbutamol sulphate, terbutaline sulphate);
sympatholytic agents (e.g., phenoxybenzamine hydrochloride); miscellaneous autonomic drugs (e.g., nicotine);
iron preparations (e.g., ferrous gluconate, ferrous sulphate);
haemostatics (e.g., aminocaproic acid);
cardiac drugs (e.g., acebutolol hydrochloride, disopyramide phosphate, flecainide acetate, procainamide hydrochloride, propranolol hydrochloride, quinidine gluconate, timolol maleate, tocainide hydrochloride, verapamil hydrochloride);
antihypertensive agents (e.g., captopril, clonidine hydrochloride, hydralazine hydrochloride, mecamylamine hydrochloride, metoprolol tartrate); vasodilators (e.g., papaverine hydrochloride);
non-steroidal anti-inflammatory agents (e.g., choline salicylate, ibuprofen, ketoprofen, magnesium salicylate, meclofenamate sodium, naproxen sodium, tolmetin sodium);
opiate agonists (e.g., codeine hydrochloride, codeine phosphate, codeine sulphate, dextromoramide tartrate, hydrocodone bitartrate, hydromorphone hydrochloride, pethidine hydrochloride, methadone hydrochloride, morphine sulphate, morphine acetate, morphine lactate, morphine meconate, morphine nitrate, morphine monobasic phosphate, morphine tartrate, morphine valerate, morphine hydrobromide, morphine hydrochloride, propoxyphene hydrochloride);
anticonvulsants (e.g., phenobarbital sodium, phenytoin sodium, troxidone, ethosuximide, valproate sodium);
tranquilizers (e.g., acetophenazine maleate, chlorpromazine hydrochloride, fluphenazine hydrochloride, prochlorperazine edisylate, promethazine hydrochloride, thioridazine hydrochloride, trifluoperazine hydrochloride, lithium citrate, molindone hydrochloride, thiothixine hydrochloride);
chemotherapeutic agents (e.g., doxorubicin, cisplatin, floxuridine, methotrexate, combinations thereof, etc.);
lipid lowering agents (e.g., gemfibrozil, clofibrate, HMG-CoA reductase inhibitors, such as for example, atorvastatin, cerivastatin, fluvastatin, lovastatin, pravastatin, simvastatin, etc.);
$H_2$-antagonists (e.g., cimetidine, famotidine, nizatidine, ranitidine HCl, etc.);
anti-coagulant and anti-platelet agents (e.g., warfarin, cipyridamole, ticlopidine, etc.);
bronchodilators (e.g., albuterol, isoproterenol, metaproterenol, terbutaline, etc.);
stimulants (e.g., benzamphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate);
barbiturates (e.g., amylobarbital sodium, butabarbital sodium, secobarbital sodium);
sedatives (e.g., hydroxyzine hydrochloride, methprylon); expectorants (e.g., potassium iodide);
antiemetics (e.g., benzaquinamide hydrochloride, metoclopropamide hydrochloride, trimethobenzamide hydrochloride);
gastro-intestinal drugs (e.g., ranitidine hydrochloride); heavy metal antagonists (e.g., penicillamine, penicillamine hydrochloride);
antithyroid agents (e.g., methimazole);
genitourinary smooth muscle relaxants (e.g., flavoxate hydrochloride, oxybutynin hydrochloride);
vitamins (e.g., thiamine hydrochloride, ascorbic acid);
unclassified agents (e.g., amantadine hydrochloride, colchicine, etidronate disodium, leucovorin calcium, methylene blue, potassium chloride, pralidoxime chloride.
steroids, particularly glucocorticoids (e.g., prednisolone, prednisone, cortisone, hydrocortisone, methylprednisolone, betamethasone, dexamethasone, triamcinolone).

The drugs may be in their base for, or a pharmaceutically acceptable salt or complex may be used. The list of possible therapeutic classes and particular drugs listed above are representative only, and are not meant to limit the scope of the invention in any way.

The chronotherapeutic formulations of the present invention may be utilized to treat any condition known (or which become known) to those skilled in the art which would benefit from such therapy. These therapies include, but are not limited to allergic rhinitis, attention deficit disorder, asthma, arthritis, cancer therapy, cardiovascular disease, high cholesterol, hypertension, and ulcers.

With respect to allergic rhinitis, major symptoms of sneezing, runny nose and stuffy nose are typically worse upon rising than during the middle of the activity span of a given day. The chronotherapeutic approach of the present invention could also help offset the sneezing, nasal congestion and runny nose and eyes that come with allergies. For instance, hay fever symptoms peak in the morning. Some studies show taking an antihistamine in the evening, rather than during the day, helps block symptoms before a patient gets out of bed, rather than waiting for symptoms to begin. Thus, it would be greatly desirable to provide a chronotherapeutic oral formulation of, for e.g., an antihistamine, which would be taken at a convenient time and which would have release the dose at a time point such that the maximal effect of the dosage form is reached in the morning.

With respect to asthma, normal lung function undergoes circadian changes and reaches a low point in the early morning hours. This dip particularly pronounced in people with asthma. Chronotherapy for asthma is aimed at getting maximal effect from bronchodilator medications during the early morning hours. It has been preferred that the key to managing asthma cases is chronotherapy, and that treatment to improve nighttime asthma will allow for improvement of daytime manifestations of asthma. Certainly dosage and timing are related for asthma patients, whose number has doubled since 1975 in America alone. The majority of asthma patients suffer most at night, possibly because that is when cortisol, the body's natural anti-inflammatory, is at its lowest level. The most common time for an attack is 4 am, so the agony of the asthma itself is often compounded by the further strain of sleeplessness. Thus, it would be greatly desirable to provide a chronotherapeutic oral formulation of, e.g., an antihistamine, which would be taken at a convenient time and which would release the dose at, e.g., just before 4 a.m., such that the maximal effect of the dosage form is reached at that time.

The chronotherapeutic formulations of the invention may also be used to treat arthritis. Glucocorticosteroids have a very favourable effect on the symptoms of rheumatoid arthritis, e.g. morning stiffness, joint pain and joint swelling. With respect to arthritis, chronobiological patterns have been observed with arthritis pain. People with osteoarthritis (the most common form of arthritis) tend to have less pain in the morning and more at night. But for people with rheumatoid arthritis, the pain usually peaks in the morning and decreases as the day wears on. Recent animal studies showing that joint inflammation in rats fluctuates over a 24-hour period support these observations by both patients and physicians. Potential drug candidates in this therapeutic area include (for all forms of arthritis) standard treatment, NSAIDs and corticosteroids, etc. Preferably, the dosages should be timed to ensure that the highest blood levels of the drug coincide with peak pain. For osteoarthritis—the optimal time for an NSAID (ibuprofen, etc.) would be around noon or mid-afternoon. For rheumatoid arthritis—the optimal time for an NSAID to be taken is after the evening meal.

With respect to attention deficit disorder, it has been observed that peak plasma concentrations of the drug are lower when sustained release formulations are used, and in some instances, sustained release formulations of methylphenidate have been shown to have lower efficacy than conventional dosage forms. A dosage form which provides for a delay in release of maximally effective amount of an agent to treat attention deficit disorder could be useful, particularly if the dosage form provides in one administration, and initial release of the active agent, followed by a predictable delay and then a second release of the active agent. Potential drug candidates include stimulants such as for example methylphenidate and pharmaceutically acceptable salts thereof.

With respect to cancer therapy, animal studies suggest that chemotherapy may be more effective and less toxic if cancer drugs are administered at carefully selected times. The studies currently suggest that there may be different chronobiological cycles for normal cells and tumor cells. If this is true, the goal would be to time the administration of cancer drugs to the chronobiological cycles of tumor cells, making them more effective against the cancer and less toxic to normal tissues. Potential drug candidates include, e.g., injectables such as doxorubicin and cisplatin (combination) and floxuridine.

Chronotherapeutics are not entirely new in the treatment of cardiovascular disease. Since 1986, people with angina have been treated with nitroglycerin patches that are attached to their chest or shoulder in the morning and are removed in the evening. This is considered to be "side door" chronotherapy because it is not based on the recognition that a disease gets worse at a certain time of the day, and therefore should be treated at that time of the day. Rather, it arose out of the recognition that nitroglycerin is not effective when it is continuously administered. Based on the fact that cardiologic diseases have a 24-hour pattern, the use of the chronotherapeutic formulations of the present invention would be greatly desirable. It has been thought by those skilled in the art that heart attacks, sudden death, angina and stroke all seem to peak in the morning hours. Thus, it would be greatly desirable to provide a chronotherapeutic oral formulation which would be taken at a convenient time and which would release the dose such that the maximal effect of the dosage form is reached at that time. Potential drug candidates include antihypertensive agents, antiischemic agents, and agents that control clotting.

With respect to hypertension, blood pressure fluctuates over the 24-hour (circadian) period. In most normotensive patients and in most patients with essential hypertension (systemic vasoconstriction is associated with increased peripheral vascular resistance in arterioles), circadian mechanisms plus differences in activity and stress during the sleep/activity cycle cause blood pressure to rise rapidly upon awakening. After it peaks during daytime activity, blood pressure declines during sleep by 10% to 20% of the mean daytime level. Both blood pressure and heart rate typically rise early in the morning and significantly increase myocardial oxygen demand to cause myocardial ischemia in patients with known or nondiagnosed coronary artery disease. The rapid surge in blood pressure on awakening is associated with an increased incidence of morning cerebrovascular accidents and myocardial infarction. Moreover, the incidence of cerebrovascular accidents and other cardiovascular events (sudden death, acute myocardial infarction, and total ischemic burden) also follows a circadian pattern, being greatest during the first 6 hours of the activity span (6 a.m. to 12 noon) and least during sleep, as observed from the Framingham Study results. Morning surges of blood pressure can theoretically rupture atherosclerotic plaques in coronary arteries, injure underlying tissue, and promote clot formation in the early morning when coagulation processes are most active. Thus, it would be greatly desirable to provide a chronotherapeutic oral formulation which would be taken at a convenient time and which would have release the dose such that the maximal effect of the dosage form is reached at that time.

In addition to a rapid rise in blood pressure on awakening, a "dip" in blood pressure occurs in most people during nighttime sleep. The dip may vary or be absent in patients with more severe forms of hypertension and among patients with secondary hypertension, in whom blood pressure either fails to decline as expected or else rises during sleep, relative to daytime levels. Blood pressure patterns have been grouped into four categories: (i) "dippers" show a 10% to 20% decline in blood pressure during nighttime sleep compared with their average daytime blood pressure level; (ii) "nondippers" have nighttime blood pressures that vary little from the daytime levels; (iii) "superdippers" show a decline in blood pressure greater than 20% at night from the daytime mean level; and (iv) "risers" experience a high blood pressure at night compared with daytime levels. Deviations in blood pressure from normal circadian patterns are associated with an increased risk of end-organ damage and adverse cardiovascular events. Hypertensive patients with nocturnal patterns of superdipping or nondipping blood pressure are more likely to develop eye, renal, and cardiac pathologies and show a higher rate of cardiovascular events, such as cerebrovascular accidents and myocardial infarction, than normal dippers.

Chronotherapy is a treatment approach that allows for better control of blood pressure during the day and night by delivering medication in amounts proportional to patients' needs and, therefore, in synchrony with the circadian blood pressure rhythm. More chronotherapeutic antihypertension medication is delivered in the morning and daytime when blood pressure is greatest, and less at night when blood pressure typically declines to the lowest level. The incidence of early morning cardiovascular events could theoretically be decreased if early morning surges in blood pressure and heart rate are blunted by the chronotherapeutic administration of indicated drugs using appropriate delivery systems.

The calcium channel blocker verapamil reduces heart rate as well as blood pressure, which is especially beneficial for patients with both ischemic heart disease and hypertension. These characteristics of verapamil and its appropriate half-life made it a good choice for the formulation of an antihypertensive drug with a chronotherapeutic oral drug absorption system (CODAS). This system was designed to be taken at bedtime, to cause a 4- to 5-hour initial lag in drug delivery and, thereafter, to achieve a controlled release of drug. CODAS-verapamil capsules (Verelan® PM) were made using the CODAS multiparticulate technology along with verapamil-coated beads. When taken as directed, this formulation results in a maximum verapamil plasma concentration around the time of awakening in the morning. Studies showed that nighttime dosing of verapamil chronotherapy allows for better control of the sharp morning blood pressure rise than do conventional antihypertensive medications. Bedtime dosing with verapamil chronotherapy also controls daytime blood pressure without inducing hypotension or superdipping of blood pressure at night, reducing the risk of target organ damage due to poor perfusion pressure. Furthermore, verapamil chronotherapy is designed to deliver more medication in the daytime than conventional verapamil and other antihypertension medications. Potential drug candidates include antihypertensive medications such as calcium channel blockers.

Medications to control high cholesterol, such as HMG-CoA reductase inhibitors, are also considered to work better when given in the evening, a time when enzyme activity levels peak. Therefore, it would be greatly desirable to provide a chronotherapeutic oral formulation which would be taken at a convenient time and which would have release the dose such that the maximal effect of the dosage form is reached at that time.

Treating ulcers is another example where timing is important. Since it is known that the acidity produced by the stomach peaks at 6 p.m., medication to reduce the secretion of acid in the stomach can therefore be delivered accordingly.

The benefits of chronotherapeutics include safety and more efficient treatment than conventional therapies. This is achieved by delivering more medication when risk of disease is greater, and delivering less medication when potential for disease symptoms are less likely. Other benefits to the patient include an increased quality of life and a once-a-day drug delivery system to increase patient compliance.

In certain preferred embodiments of the invention where the manifestations of the disease state to be treated (e.g., asthmatic attack, pain from arthritis) are greatest upon awakening, the chronotherapeutic formulations are preferably orally administered to the patient at bedtime (e.g., at about 9 or 10 p.m.) and have a lag time of about 5 or 6 hours, so that, e.g., a substantial portion of the drug in the compression coated delayed release oral dosage form is released, e.g., between 2-3 a.m., or between 3-4 a.m., and the drug is absorbed from the gastrointestinal tract and provides therapeutic efficacy at a time which correlates with the peak of the manifestations of the disease state.

In situations where the active agent is a low dose active agent (e.g., a drug administered in a (unit) dose amount from about 0.01 mg to about 40 mg), in certain preferred embodiments, the total tablet weight is from about 220 mg to about 900 mg; and the core weight is preferably from about 50 mg to about 170 mg. Preferably, the core is from about 5 to about 23 percent, most preferably about 18 to about 20 percent by weight of the total tablet weight. In embodiments wherein the active agent is a low dose active agent, the coating is preferably from about 150 mg to about 850 mg. Preferably, the coating is from about 75 to about 94 percent by weight, most preferably from about 78 to 80 percent by weight of the total tablet. Preferably, where the active dose is a low dose active agent, the ratio of the core to gum (in the compression coating) is from about 1:0.37 to about 1:5, preferably from about 1:0.37 to about 1:1.12, most preferably from about 1:0.75. Where the active dose is a low dose active agent, the ratio of the core to compression coating material (all ingredients) is preferably from about 1:2 to about 1:9, and in certain embodiments more preferably about 1:4.

In situations where the active agent is a relatively high dose active agent (e.g., a drug administered in a (unit) dose amount from about 41 mg to about 300 mg), the ratio of core to gum (in the compression coating) is from about 1:0.3 to about 1:3, preferably from about 1:0.6 to about 1:1.5. In certain embodiments, preferably where the active agent is a high dose active agent, the ratio of the core to compression coating material (all ingredients) is from about 1:1 to about 1:5, preferably from about 1:2 to about 1:3. In situations where the active agent is a relatively high dose active agent, the total tablet weight is preferably from about 500 mg to about 1500 mg, more preferably from about 750 mg to about 1000 mg.

In the appended examples, the cores comprising the active agent are typically compression coated with the coating formulation by hand on a rotary tablet press. In such a process, roughly half the outer core material is first added to the die. An inner core tablet is typically centered on the powder bed and is covered with the other half of the outer coating powder. However, one skilled in the art will appreciate that compression coating may be accomplished via automated tablet presses for commercialization. Prior to compression coating with any tablet press, preferably 0.75% Pruv® (sodium stearyl fumarate, NF) or another suitable lubricant is added to the compression coating material(s). In certain examples wherein the coatings are indicate by the gums, for example, 50% xanthan gum (XG), the coating comprises 50% xanthan gum diluted with dextrose; and for example 50% locust bean gum (LBG), the coating comprises 50% locust bean gum diluted with dextrose, etc.

DETAILED DESCRIPTION OF THE PREFERRED EMBODIMENTS

The following examples illustrate various aspects of the present invention. They are not to be construed to limit the claims in any manner whatsoever.

Example 1

A delayed release material to be used in the compression coatings of the invention is prepared having the following formulation listed in Table 1:

TABLE 1

| Component | Percentage |
|---|---|
| 1. Xanthan Gum | 12 |
| 2. Locust Bean Gum | 18 |
| 3. Dextrose | 70 |
| 4. Water* | q.s. |

*Removed during processing

Process:

1. The requisite amounts of xanthan gum, locust bean gum, and dextrose are dry blended in a high speed mixer/granulator for 3 minutes.

2. Water (125-150 ml) is added to the dry blended mixture, and granulated for another 3 minutes.

3. The granulation is then dried in a fluid bed dryer to a LOD (loss on drying) of less than about 10% by weight (e.g., 4-7% LOD).

Example 2

A delayed release material to be used in the compression coatings of the invention is prepared having the following formulation listed in Table 2:

TABLE 2

| Component | Percentage |
|---|---|
| 1. Xanthan Gum | 25 |
| 2. Locust Bean Gum | 25 |
| 3. Dextrose | 35 |
| 4. Calcium Sulfate Dihydrate | 10 |
| 5. Ethylcellulose | 5 |
| 5. Alcohol, SD3A, anhydrous* | 20 |
| 6. Water* | q.s. |

*Removed during processing

Process:

1. The requisite amounts of xanthan gum, locust bean gum, calcium sulfate, and dextrose are dry blended in a high speed mixer/granulator for 3 minutes.

2. A slurry of hydrophobic polymer (ethylcellulose) is prepared by dissolving ethyl cellulose in ethyl alcohol.

3. The slurry is added to the dry blended mixture, and granulated for another 3 minutes.

4. The granulation was then dried in a fluid bed dryer to a LOD (loss on drying) of less than about 10% by weight (e.g., 4-7% LOD).

Example 3

A delayed release material to be used in the compression coatings of the invention is prepared having the following formulation listed in Table 3:

TABLE 3

| Component | Percentage |
|---|---|
| 1. Xanthan Gum | 15 |
| 2. Locust Bean Gum | 15 |
| 3. Dextrose | 60 |
| 4. Calcium Sulfate Dihydrate | 10 |
| 5. Water* | q.s. |

*Removed during processing

Process:

1. The requisite amounts of xanthan gum, locust bean gum, calcium sulfate, and dextrose are dry blended in a high speed mixer/granulator for 3 minutes.

2. Water (125-150 ml) is added to the dry blended mixture, and granulated for another 3 minutes.

3. The granulation is then dried in a fluid bed dryer to a LOD (loss on drying) of less than about 10% by weight (e.g., 4-7% LOD).

Example 4

A delayed release material to be used in the compression coatings of the invention is prepared having the following formulation listed in Table 4:

TABLE 4

| Component | Percentage |
|---|---|
| 1. Xanthan Gum | 16 |
| 2. Locust Bean Gum | 24 |
| 3. Dextrose | 60 |
| 4. Water* | q.s. |

*Removed during processing

Process:

The same process for Example 1 is used to prepare the delayed release coating of Example 4.

Example 5

A delayed release material to be used in the compression coatings of the invention is prepared having the following formulation listed in Table 5:

TABLE 5

| Component | Percentage |
|---|---|
| 1. Xanthan Gum | 20 |
| 2. Locust Bean Gum | 30 |
| 3. Dextrose | 45 |
| 4. Calcium Sulfate Dihydrate | 5 |
| 5. Water* | q.s. |

*Removed during processing

Process:

The same process for Example 3 is used to prepare the delayed release material to be used in the compression coatings of the invention in Example 5.

Example 6

A delayed release material to be used in the compression coatings of the invention is prepared having the following formulation listed in Table 6:

TABLE 6

| Component | Percentage |
|---|---|
| 1. Xanthan Gum | 12 |
| 2. Locust Bean Gum | 18 |
| 3. Dextrose | 65 |
| 4. Calcium Sulfate Dihydrate | 5 |
| 5. Water* | q.s. |

*Removed during processing

Process:

The same process for Example 3 is used to prepare the delayed release material to be used in the compression coatings of the invention in Example 6.

Example 7

A delayed release material to be used in the compression coatings of the invention is prepared having the following formulation listed in Table 7:

TABLE 7

| Component | Percentage |
| --- | --- |
| 1. Xanthan Gum | 10 |
| 2. Locust Bean Gum | 15 |
| 3. Dextrose | 75 |
| 4. Water* | q.s. |

*Removed during processing

Process:

The same process for Example 1 is used to prepare the delayed release material to be used in the compression coatings of the invention in Example 7.

Example 8

A delayed release material to be used in the compression coatings of the invention is prepared having the following formulation listed in Table 8:

TABLE 8

| Component | Percentage |
| --- | --- |
| 1. Xanthan Gum | 8 |
| 2. Locust Bean Gum | 12 |
| 3. Dextrose | 80 |
| 4. Water* | q.s. |

*Removed during processing

Process:

The same process for Example 1 is used to prepare the delayed release material to be used in the compression coatings of the invention in Example 8.

Example 9

A delayed release material to be used in the compression coatings of the invention is prepared having the formulation listed in Table 9:

TABLE 9

| Component | Percentage |
| --- | --- |
| 1. Xanthan Gum | 20 |
| 2. Locust Bean Gum | 30 |
| 3. Lactose | 50 |
| 4. Water* | q.s. |

*Removed during processing

Process:

The same process for Example 1 is used to prepare the delayed release material to be used in the compression coatings of the invention in Example 5, substituting lactose for dextrose.

Example 10

A delayed release material to be used in the compression coatings of the invention is prepared having the formulation listed in Table 10:

TABLE 10

| Component | Percentage |
| --- | --- |
| 1. Xanthan Gum | 20 |
| 2. Locust Bean Gum | 30 |
| 3. Mannitol | 45 |
| 4. Hydroxypropylmethylcellulose | 5 |
| 5. Water* | q.s. |

*Removed during processing

Process:

1. The requisite amounts of xanthan gum, locust bean gum, mannitol, and hydroxypropylmethylcellulose are dry blended in a high speed mixer/granulator for 3 minutes.
2. Water (125-150 ml) is added to the dry blended mixture, and granulated for another 3 minutes.
3. The granulation is then dried in a fluid bed dryer to a LOD (loss on drying) of less than about 10% by weight (e.g., 4-7% LOD).

Example 11

A delayed release material to be used in the compression coatings of the invention is prepared having the formulation listed in Table 11:

TABLE 11

| Component | Percentage |
| --- | --- |
| 1. Xanthan Gum | 12 |
| 2. Locust Bean Gum | 18 |
| 3. Mannitol | 70 |
| 4. Water* | q.s. |

*Removed during processing

Process:

The same process for Example 1 is used to prepare the delayed release material to be used in the compression coatings of the invention in Example 11, substituting mannitol for dextrose.

Example 12

A delayed release material to be used in the compression coatings of the invention is prepared having the formulation listed in Table 12:

TABLE 12

| Component | Percentage |
| --- | --- |
| 1. Xanthan Gum | 9 |
| 2. Locust Bean Gum | 13.5 |
| 3. Mannitol | 77.5 |
| 4. Water* | q.s. |

*Removed during processing

Process:

The same process for Example 10 is used to prepare the delayed release material to be used in the compression coatings of the invention in Example 12.

Example 13

A delayed release material to be used in the compression coatings of the invention is prepared having the formulation listed in Table 13:

TABLE 13

| Component | Percentage |
| --- | --- |
| 1. Xanthan Gum | 8 |
| 2. Locust Bean Gum | 12 |
| 3. Mannitol | 80 |
| 4. Water* | q.s. |

*Removed during processing

Process:

The same process for Example 12 is used to prepare the delayed release material to be used in the compression coatings of the invention in Example 13.

Example 14

A delayed release material to be used in the compression coatings of the invention is prepared having the formulation listed in Table 14:

TABLE 14

| Component | Percentage |
| --- | --- |
| 1. Xanthan Gum | 6 |
| 2. Locust Bean Gum | 9 |
| 3. Mannitol | 85 |
| 4. Water* | q.s. |

*Removed during processing

Process:

The same process for Example 12 is used to prepare the delayed release material to be used in the compression coatings of the invention in Example 14.

Example 15

A delayed release material to be used in the compression coatings of the invention is prepared having the formulation listed in Table 15:

TABLE 15

| Component | Percentage |
| --- | --- |
| 1. Xanthan Gum | 4 |
| 2. Locust Bean Gum | 6 |
| 3. Mannitol | 90 |
| 4. Alcohol, SD3A, anhydrous* | — |
| 5. Water* | q.s. |

*Removed during processing

Process:

The same process for Example 12 is used to prepare the delayed release material to be used in the compression coatings of the invention in Example 15.

Example 16

A delayed release coating is prepared having the following formulation listed in Table 16:

TABLE 16

| Component | Percentage |
| --- | --- |
| 1. Xanthan Gum | 3 |
| 2. Locust Bean Gum | 4.5 |
| 3. Mannitol | 92.5 |
| 4. Water* | q.s. |

*Removed during processing

Process:

The same process for Example 12 is used to prepare the delayed release material to be used in the compression coatings of the invention in Example 16.

Example 17

A delayed release material to be used in the compression coatings of the invention is prepared having the formulation listed in Table 17:

TABLE 17

| Component | Percentage |
| --- | --- |
| 1. Xanthan Gum | 8 |
| 2. Locust Bean Gum | 12 |
| 3. Dextrose | 40 |
| 4. Microcrystalline Cellulose | 40 |
| 5. Water* | q.s. |

*Removed during processing

Process:

1. The requisite amounts of xanthan gum, locust bean gum, dextrose, and microcrystalline cellulose are dry blended in a high speed mixer/granulator for 3 minutes.
2. Water (125-150 ml) is added to the dry blended mixture, and granulated for another 3 minutes.
3. The granulation is then dried in a fluid bed dryer to a LOD (loss on drying) of less than about 10% by weight (e.g., 4-7% LOD).

Example 18

A delayed release material to be used in the compression coatings of the invention is prepared having the formulation listed in Table 18:

TABLE 18

| Component | Percentage |
| --- | --- |
| 1. Xanthan Gum | 8 |
| 2. Locust Bean Gum | 12 |
| 3. Dextrose | — |
| 4. Microcrystalline Cellulose | 80 |
| 5. Water* | q.s. |

*Removed during processing

Process:

The same process for Example 1 is used to prepare the delayed release material to be used in the compression coatings of the invention in Example 18, substituting microcrystalline cellulose for dextrose.

Example 19

A prednisolone core composition was prepared having the ingredients set forth in Table 19:

TABLE 19

| Component | Percent | amt. (mg) |
|---|---|---|
| 1. Prednisolone | 2.0 | 1.0 |
| 2. Prosolv SMCC ™ 50 | 32.75 | 16.4 |
| 3. Prosolv SMCC ™ 90 | 50 | 25.0 |
| 4. Explotab ® | 10 | 5.0 |
| 5. Sodium carboxymethylcellulose | 5 | 2.5 |
| 6. Pruv | 0.25 | 0.1 |
| Total | 100 | 50 |
| Core size and shape | 3/16" Round SC* | |

*SC means standard concave

Process:
1. Blend the requisite amounts of prednisolone and Prosolv™ SMCC 50 in a V-blender for 5 to 10 minutes.
2. Add the requisite amounts of Prosolv™ SMCC 90, Explotab® and sodium carboxymethylcellulose to the blend and continue blending for another 5 minutes.
3. Add the requisite amount of Pruv to the mixture and blend for an additional 5 minutes.
4. Compress the tablet cores using tablet press.

Example 20

A prednisolone core composition was prepared having the formulation ingredients set forth in Table 20:

TABLE 20

| Component | Percent | amt. (mg) |
|---|---|---|
| 1. Prednisolone | 10 | 5 |
| 2. Prosolv SMCC ™ 50 | NA | NA |
| 3. Prosolv SMCC ™ 90 | 81.75 | 40.875 |
| 4. Explotab ® | 6 | 3 |
| 5. Sodium carboxymethylcellulose | NA | NA |
| 6. Pruv | 0.25 | 0.125 |
| 7. PVP | 2 | 1 |
| Total | 100 | 50 |
| Core size and shape | 3/16" Round FF* | |

*FF = flat face

Process:
1. Blend the requisite amounts of prednisolone, Prosolv™ SMCC 90, Explotab® for 5 to 10 minutes.
2. Add the requisite amount of Pruv and PVP to the mixture and blend for an addition 5 minutes.
3. Compress the tablet cores using tablet press.

Example 21

A prednisolone core composition was prepared having the formulation ingredients set forth in Table 21:

TABLE 21

| Component | Percent | amt. (mg) |
|---|---|---|
| 1. Prednisolone | 10 | 5 |
| 2. Prosolv SMCC ™ 50 | NA | NA |
| 3. Prosolv SMCC ™ 90 | 75.75 | 37.375 |
| 4. Explotab ® | 10 | 5 |
| 5. Sodium carboxymethylcellulose | 5 | 2.5 |
| 6. Pruv | 0.25 | 0.1 |
| Total | 100 | 50 |
| Core size and shape | 3/16" Round FF | |

Process:
1. Blend the requisite amounts of prednisolone, Prosolv™ SMCC 90, Explotab®, and sodium carboxymethylcellulose for 5 to 10 minutes.
2. Add the requisite amount of Pruv and PVP to the mixture and blend for an additional 5 minutes.
3. Compress the tablet cores using tablet press.

Example 22

A prednisolone core composition was prepared having the formulation ingredients set forth in Table 22:

TABLE 22

| Component | Percent | amt. (mg) |
|---|---|---|
| 1. Prednisolone | 2 | 1.0 |
| 2. Prosolv SMCC ™ 50 | 40 | 20.0 |
| 3. Prosolv SMCC ™ 90 | 47.75 | 23.9 |
| 4. Explotab ® | 6 | 3.0 |
| 5. PVP | 2 | 1.0 |
| 6. Talc | 2 | 1.0 |
| 7. Pruv | 0.25 | 0.1 |
| Total | 100 | 50 |
| Core size and shape | 3/16" Round SC | |

Process:
1. Blend the requisite amounts of prednisolone and Prosolv™ SMCC 50 in a V-blender for 5 to 10 minutes.
5. Add the requisite amounts of Prosolv™ SMCC 90, Explotab®, PVP, and talc to the blend and continue blending for another 5 minutes.
6. Add the requisite amount of Pruv to the mixture and blend for an additional 5 minutes.
7. Compress the tablet cores using tablet press.

Example 23

A prednisolone core composition was prepared having the formulation ingredients set forth in Table 23:

TABLE 23

| Component | Percent | amt. (mg) |
|---|---|---|
| 1. Prednisolone | 2 | 3.4 |
| 2. Prosolv SMCC ™ 50 | 40 | 68 |
| 3. Prosolv SMCC ™ 90 | 47.75 | 81.75 |
| 4. Explotab ® | 6 | 10.2 |

TABLE 23-continued

| Component | Percent | amt. (mg) |
|---|---|---|
| 5. Sodium carboxymethylcellulose | 2 | 3.4 |
| 6. Talc | 2 | 3.4 |
| 7. Pruv | 0.25 | 0.425 |
| Total | 100 | 170 |
| Core size and shape | ¼" Round FF | |

Process:

1. Blend the requisite amounts of prednisolone and Prosolv™ SMCC 50 in a V-blender for 5 to 10 minutes.
2. Add the requisite amounts of Prosolv™ SMCC 90, Explotab®, sodium carboxymethylcellulose, and talc to the blend and continue blending for another 5 minutes.
3. Add the requisite amount of Pruv to the mixture and blend for an additional 5 minutes.
4. Compress the tablet cores using tablet press.

Example 24

A prednisolone core composition was prepared having the formulation ingredients set forth in Table 24:

TABLE 24

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 47.75 | 23.875 |
| 4. Explotab ® | 6 | 3 |
| 5. Sodium carboxymethylcellulose | 2 | 1 |
| 6. Talc | 2 | 1 |
| 6. Pruv | 0.25 | 0.125 |
| Total | 100 | 50 |
| Core size and shape | 3⁄16" Round SC | |

Process:

The same process for Example 23 is used to prepare the core of Example 24.

Example 25

A prednisolone core composition was prepared having the formulation ingredients set forth in Table 25:

TABLE 25

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 55.75 | 27.85 |
| 4. Explotab ® | NA | NA |
| 5. Sodium carboxymethylcellulose | NA | NA |
| 6. Talc | 2 | 1 |
| 7. Pruv | 0.25 | 0.125 |
| Total | 100 | 50 |
| Core size and shape | 3⁄16" Round SC | |

Process:

The same process for Example 23 is used to prepare the core of Example 25, without the inclusion of Explotab® and sodium carboxymethylcellulose.

Example 26

A prednisolone core composition was prepared having the formulation ingredients set forth in Table 26:

TABLE 26

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 52.75 | 26.375 |
| 4. Explotab ® | 3 | 1.5 |
| 5. Sodium carboxymethylcellulose | NA | NA |
| 6. Talc | 2 | 1 |
| 7. Pruv | 0.25 | 0.125 |
| Total | 100 | 50 |
| Core size and shape | 3⁄16" Round SC | |

Process:

The same process for Example 23 is used to prepare the core of Example 26, without the inclusion of sodium carboxymethylcellulose.

Example 27

A prednisolone core composition was prepared having the formulation ingredients set forth in Table 27:

TABLE 27

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 51.75 | 25.875 |
| 4. Explotab ® | 3 | 1.5 |
| 5. Sodium carboxymethylcellulose | 1 | 0.5 |
| 6. Talc | 2 | 1 |
| 6. Pruv | 0.25 | 0.125 |
| Total | 100 | 50 |
| Core size and shape | 3⁄16" Round SC | |

Process:

The same process for Example 23 is used to prepare the core of Example 27.

Example 28

A prednisolone core composition was prepared having the formulation ingredients set forth in Table 28:

TABLE 28

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 53.75 | 26.875 |
| 4. Explotab ® | NA | NA |

TABLE 28-continued

| Component | Percent | amt. (mg) |
|---|---|---|
| 5. Sodium carboxymethylcellulose | 2 | 1 |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 28, without the inclusion of Explotab®.

Example 29

A prednisolone core composition was prepared having the formulation ingredients set forth in Table 29:

TABLE 29

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 47.75 | 23.875 |
| 4. Explotab ® | 2 | 1 |
| 5. Sodium carboxymethylcellulose | 6 | 3 |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 29.

Example 30

A prednisolone core composition was prepared having the formulation ingredients set forth in Table 30:

TABLE 30

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 49.75 | 24.875 |
| 4. Explotab ® | NA | NA |
| 5. Sodium carboxymethylcellulose | 6 | 3 |

TABLE 30-continued

| Component | Percent | amt. (mg) |
|---|---|---|
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 30, without the inclusion of Explotab®.

Example 31

A prednisolone core composition was prepared having the formulation ingredients set forth in Table 31:

TABLE 31

| Component | Percent | amt. (mg) |
|---|---|---|
| 1. Prednisolone | 2 | 1 |
| 2. Prosolv SMCC ™ 50 | 26 | 13 |
| 3. Prosolv SMCC ™ 90 | 49.75 | 24.875 |
| 4. Explotab ® | 20 | 10 |
| 5. Sodium carboxymethylcellulose | NA | NA |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 31, without the inclusion of sodium carboxymethylcellulose.

Example 32

A prednisolone core composition was prepared having the formulation ingredients set forth in Table 32:

TABLE 32

| Component | Percent | amt. (mg) |
|---|---|---|
| 1. Prednisolone | 2 | 1 |
| 2. Prosolv SMCC ™ 50 | 26 | 13 |
| 3. Prosolv SMCC ™ 90 | 49.75 | 24.875 |
| 4. Explotab ® | 20 | 10 |

TABLE 32-continued

| Component | Percent | amt. (mg) |
|---|---|---|
| 5. Sodium carboxymethylcellulose | NA | NA |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 32, without the inclusion of sodium carboxymethylcellulose.

Example 33

A prednisolone core composition was prepared having the formulation ingredients set forth in Table 33:

TABLE 33

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 52.75 | 26.375 |
| 4. Explotab ® | 3 | 1.5 |
| 5. Sodium carboxymethylcellulose | NA | NA |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 33, without the inclusion sodium carboxymethylcellulose.

Example 34

A prednisolone core composition was prepared having the formulation set forth in Table 34:

TABLE 34

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 51.75 | 25.875 |
| 4. Explotab ® | 3 | 1.5 |
| 5. Sodium carboxymethylcellulose | 1 | 0.5 |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 34.

Example 35

A prednisolone core composition was prepared having the formulation ingredients set forth in Table 35:

TABLE 35

| Component | Percent | amt. (mg) |
|---|---|---|
| 1. Prednisolone | 2 | 1 |
| 2. Prosolv SMCC ™ 50 | 40 | 20 |
| 3. Prosolv SMCC ™ 90 | 53.75 | 26.875 |
| 4. Explotab ® | NA | NA |
| 5. Sodium carboxymethylcellulose | 2 | 1 |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 35, without the inclusion of Explotab®.

Example 36

A prednisolone core composition was prepared having the formulation ingredients set forth in Table 36:

TABLE 36

| Component | Percent | amt. (mg) |
|---|---|---|
| 1. Prednisolone | 4 | 2 |
| 2. Prosolv SMCC ™ 50 | 40 | 20 |
| 3. Prosolv SMCC ™ 90 | 45.75 | 22.875 |
| 4. Explotab ® | 6 | 3 |
| 5. Sodium carboxymethylcellulose | 2 | 1 |
| 6. Talc | 2 | 1 |
| 7. Pruv | 0.25 | 0.125 |
| Total | 100 | 50 |
| Core size and shape | 3/16" Round SC | |

Process:

The same process for Example 23 is used to prepare the core of Example 36.

Examples 37-39

In Examples 37-39, prednisolone tablets were prepared having a core formulation as described in Example 21 and coating formulation as described in Example 3. The tablet formulations of Examples 37-39 are listed in Table 37 below:

TABLE 37

| Component | Ex. 37 Amt. (mg) | Ex. 38 amt. (mg) | Ex. 39 amt. (mg) |
|---|---|---|---|
| 1. Example 21 core | 50 | 50 | 50 |
| 2. Example 3 coating | 150 | 250 | 350 |
| Total tablet weight | 200 | 300 | 400 |
| Size and shape of tablet | 9/32" round | 3/8" round | 3/8" round |
| Compression force | standard concave 8-9 kP | standard concave 8-9 kP | standard concave 8-9 kP |

Process:

1. Weigh out the requisite amount of immediate release cores and set aside.
2. Blend 0.75% by weight of Pruv® sodium stearyl fumarate, NF, (commercially available from the Edward Mendell Co., Inc.) with the requisite amount of coating for 5 minutes.
3. Weigh out approximately half of the compression coating.
4. Pour the lower layer of the compression coating into the lower punch of the die.
5. Place the immediate release core in the center of the compression coating.
6. Pour the top layer of into the die.
7. Rotate the punch station for compression.
8. Weigh out finished tablets to ensure proper weight.

The tablets of Examples 37-39 were tested using USP apparatus type III with 250 mL DI water at 15 dips per minute (dpm) giving the following results listed in Table 38:

TABLE 38

|  | Time (hours) | | | | | | | |
| --- | --- | --- | --- | --- | --- | --- | --- | --- |
|  | 0 | 2 | 4 | 6 | 8 | 10 | 12 | 16 |
| Example 37 % dissolved | 0 | 0 | 0 | 0 | 18.6 | — | — | — |
| Example 38 % dissolved | 0 | 0 | 0 | 0 | 0 | 35.6 | 100 | 100 |
| Example 39 % dissolved | 0 | 0 | 0 | 0 | 0 | 0 | 6.8 | 100 |

The tablets of Examples 37-39 resulted the following lag times (time when prednisolone is release from the tablet) and full release times (time when all of prednisolone is released from the tablet) listed in Table 39:

TABLE 39

|  | Example 37 | Example 38 | Example 39 |
| --- | --- | --- | --- |
| Lag time (hours) | 6-7 | 8-9 | 10-12 |
| Full release (hours) | 8-9 | 10-12 | 14-16 |

Examples 40-42

In Examples 40-42, prednisolone tablets were prepared having a core formulation as described in Example 21 and coating formulation as described Example 2. The tablet formulations of Examples 40-42 are listed in Table 40 below:

TABLE 40

| Component | Ex. 40 Amt. (mg) | Ex. 41 amt. (mg) | Ex. 42 amt. (mg) |
| --- | --- | --- | --- |
| 1. Example 21 core | 50 | 50 | 50 |
| 2. Example 2 coating | 150 | 250 | 350 |
| Total tablet weight | 200 | 300 | 400 |
| Size and shape of tablet | 9/32" round | 3/8" round | 3/8" round |
| Compression force | standard concave 8-9 kP | standard concave 8-9 kP | standard concave 8-9 kP |

Process:

The tablets of Examples 40-42 are prepared using the same process as examples 37-39.

The tablets of Examples 40-42 were tested using USP apparatus type III with 250 mL DI water at 15 dips per minute (dpm) giving the following results listed in Table 41:

TABLE 41

|  | Time (hours) | | | | | | | |
| --- | --- | --- | --- | --- | --- | --- | --- | --- |
|  | 0 | 2 | 4 | 6 | 8 | 10 | 12 | 16 |
| Example 40 % dissolved | 0 | — | 22.7 | 40.6 | 100 | — | — | — |
| Example 41 % dissolved | 0 | 0 | 0 | 0 | 0 | 0 | 100 | 100 |
| Example 42 % dissolved | 0 | 0 | 0 | 0 | 0 | 0 | 19.5 | 19.5 |

The tablets of Examples 40-42 resulted in the following lag times (time when prednisolone is release from the tablet) and full release times (time when all of prednisolone is released from the tablet) listed in Table 42:

TABLE 42

|  | Example 40 | Example 41 | Example 42 |
| --- | --- | --- | --- |
| Lag time (hours) | 6-7 | 10-11 | 10-11 |
| Full release (hours) | 7-8 | 11-12 | 11-12 |

As can be seen, as total tablet weight increases (due to increase in coating weight), lag time and the corresponding release time also tend to increase.

Example 43

In Example 43, various delayed release coating formulations were prepared in order to determine the effect of the gum percentage in the coating formulation on the time of release and the rate of release of the active agent within the tablet core.

The ingredients of the various delayed release coating granulations of this example having varying gum percentages are as follows:

TABLE 43a

|  | Ex. 2 Coating | | Ex. 3 coating | | Ex. 8 coating | | Xanthan | |
| --- | --- | --- | --- | --- | --- | --- | --- | --- |
| Formulation: | % | mg/tab | % | Mg/tab | % | mg/tab | % | mg/tab |
| 1. a. Core (Ex. 24 core) | — | — | — | — | 22.73% | 50 | 22.73% | 50 |
| b. Core (Ex. 22 core) | 22.73% | 50 | 22.73% | 50 | — | — | — | — |

TABLE 43a-continued

|  | Ex. 2 Coating | | Ex. 3 coating | | Ex. 8 coating | | Xanthan | |
| --- | --- | --- | --- | --- | --- | --- | --- | --- |
| Formulation: | % | mg/tab | % | Mg/tab | % | mg/tab | % | mg/tab |
| 2. Ex. 2 coating | 76.69% | 168.725 | — | — | — | — | — | — |
| 3. Ex. 3 coating | — | — | 76.69% | 168.725 | — | — | — | — |
| 4. Ex. 8 coating | — | — | — | — | 76.69% | 168.725 | — | — |
| 5. Xanthan Gum | — | — | — | — | — | — | 76.69% | 168.7 |
| 6. Sodium Stearyl Fumarate | 0.58% | 1.275 | 0.58% | 1.275 | 0.58% | 1.275 | 0.58% | 1.275 |
| Tablet weight (mg) | | 220 | | 220 | | 220 | | 220 |
| Tablet hardness (kP) | | 8-9 | | 8-9 | | 8-9 | | 8-9 |

The effects of the different percentages of gums within the delayed release compression coating are set forth in the table below.

TABLE 43b

| Xanthan Gum coating 220 mg tablet | | Ex. 8 coating 220 mg tablet | | Ex. 2 coating 220 mg tablet | | Ex. 3 coating 220 mg tablet | |
| --- | --- | --- | --- | --- | --- | --- | --- |
| Time (hrs) | Normalized Mean | Time (hrs) | Normalized Mean | Time (hrs) | Normalized Mean | Time (hrs) | Normalized Mean |
| 0 | 0.0 | 0 | 0.0 | 0 | 0.0 | 0 | 0.0 |
| 1 | 0.0 | 1 | 28.4 | 4 | 0.0 | 2 | 0.0 |
| 2 | 0.0 | 2 | 100.0 | 6 | 0.0 | 4 | 0.0 |
| 3 | 0.0 | 3 | 100.0 | 8 | 0.0 | 6 | 33.3 |

TABLE 43b-continued

| Xanthan Gum coating 220 mg tablet | | Ex. 8 coating 220 mg tablet | | Ex. 2 coating 220 mg tablet | | Ex. 3 coating 220 mg tablet | |
| --- | --- | --- | --- | --- | --- | --- | --- |
| Time (hrs) | Normalized Mean | Time (hrs) | Normalized Mean | Time (hrs) | Normalized Mean | Time (hrs) | Normalized Mean |
| 4 | 66.7 | 4 | 100.0 | 10 | 0.0 | 8 | 50.0 |
| 5 | 100.0 | 5 | 100.0 | 12 | 33.3 | 10 | 100.0 |
| 6 | 100.0 | 6 | 100.0 | 16 | 100.0 | 12 | 100.0 |

As shown in the Table 43b, the formulation with 20% gums released the active drug faster than did the formulations with 30% or 50% gums. The results followed the rank order for % gums with granulated delayed release examples. Xanthan gum (ungranulated) did not track (e.g., provide the same delayed release) as with the other delayed release coatings in this example (which had granulated gums).

As can be seen from the results set forth above, as the amount of gum with respect to drug in the formulation is increased, a corresponding increase in lag time before release of the drug is observed.

Example 44

In Example 44, various examples of delayed release compression coating formulations were prepared in order to determine the effect of ratio of the drug within the tablet to the gum within the coating formulation on the time of release and the rate of release of the active agent within the tablet core.

The ingredients of the various delayed release coating granulations are shown in the examples above. The effects of the different drug to gum ratios are set forth in the table below.

TABLE 44

| Ex. 8 coating 220 mg tablet | | Xanthan Gum coating 220 mg tablet | | Xanthan Gum coating 300 mg tablet | | Ex. 2 coating 220 mg tablet | | Ex. 3 coating 220 mg tablet | |
| --- | --- | --- | --- | --- | --- | --- | --- | --- | --- |
| Time (hrs) | Normalized Mean | Time (hrs) | Normalized Mean | Time (hrs) | Normalized Mean | Time (hrs) | Normalized Mean | Time (hrs) | Normalized Mean |
| 0 | 0.0 | 0 | 0.0 | 0 | 0.0 | 0 | 0.0 | 0 | 0.0 |
| 1 | 28.4 | 1 | 0.0 | 3 | 0.0 | 4 | 0.0 | 2 | 0.0 |
| 2 | 100.0 | 2 | 0.0 | 4 | 0.0 | 6 | 0.0 | 4 | 0.0 |
| 3 | 100.0 | 3 | 0.0 | 5 | 38.8 | 8 | 0.0 | 6 | 33.3 |
| 4 | 100.0 | 4 | 66.7 | 6 | 100.0 | 10 | 0.0 | 8 | 50.0 |
| 5 | 100.0 | 5 | 100.0 | 7 | 100.0 | 12 | 33.3 | 10 | 100.0 |
| 6 | 100.0 | 6 | 100.0 | 8 | 100.0 | 16 | 100.0 | 12 | 100.0 |

In this Example, the gums of the Ex. 8 coating (Drug:Gum ratio of 1:33.75) showed faster release time than both Ex. 3 coating (Drug:Gum ratio of 1:50.6) and Ex. 2 coating (Drug:Gum ratio of 1:84.4). Xanthan gum followed rank order with itself (e.g., the larger tablet having more total gum had a longer delay) but not with the granulated materials (Ex. 8, 2, and 3 coatings). It was observed that, as the amount of gum relative to drug is increased, a corresponding increase in lag time is observed. The conclusion reached is that increasing gum to drug ratio increased (longer) release lag time before release of the drug.

Example 45

In Example 45, various lots of delayed release coating formulations were prepared in order to determine the effect of the thickness of the sustained release coating on the time of release and the rate of release of the active agent within the tablet core.

The ingredients of the various inner core formulations are shown in the examples above, and the ingredients of the various delayed release coating granulations are shown in Table 45. The effects of the delayed release coating thickness are set forth in the table below.

TABLE 45

| Ex. 3 coating 300 mg tablet | | Ex. 3 coating 200 mg tablet | | Ex. 2 coating 300 mg tablet | | Xanthan Gum coating 220 mg tablet | |
|---|---|---|---|---|---|---|---|
| Time (hours) | Normalized Mean | Time (hours) | Normalized Mean | Time (hours) | Normalized Mean | Time (hours) | Normalized Mean |
| 0 | 0.0 | 0 | 0.0 | 0 | 0.0 | 0 | 0.0 |
| 4 | 100.0 | 4 | 49.0 | 4 | 0.0 | 1 | 0.0 |
| 6 | 100.0 | 6 | 100.0 | 6 | 0.0 | 2 | 0.0 |
| 8 | 100.0 | 8 | 100.0 | 8 | 17.9 | 3 | 0.0 |
| 10 | 100.0 | 10 | 100.0 | 10 | 51.7 | 4 | 66.7 |
| 12 | 100.0 | 12 | 100.0 | 12 | 100.0 | 5 | 100.0 |
| 16 | 100.0 | 16 | 100.0 | 16 | 100.0 | 6 | 100.0 |

| Xanthan Gum coating 300 mg tablet | | Ex. 8 coating 220 mg tablet | | Ex. 8 coating 300 mg tablet | |
|---|---|---|---|---|---|
| Time (hours) | Normalized Mean | Time (hours) | Normalized Mean | Time (hours) | Normalized Mean |
| 0 | 0.0 | 0 | 0.0 | 0 | 0.0 |
| 3 | 0.0 | 1 | 28.4 | 1 | 0.0 |
| 4 | 0.0 | 2 | 100.0 | 2 | 50.0 |
| 5 | 38.8 | 3 | 100.0 | 3 | 100.0 |
| 6 | 100.0 | 4 | 100.0 | 4 | 100.0 |
| 7 | 100.0 | 5 | 100.0 | 5 | 100.0 |
| 8 | 100.0 | 6 | 100.0 | 6 | 100.0 |

In this example, it was observed that tablets with 170 mg of Example 8 coating were faster releasing than tablets with 250 mg Example 8 coating. It was thus observed that, as the thickness of coating is increased in the tablet, a corresponding increase in lag time is observed. The conclusion reached is that tablets with a thicker coating showed a longer lag time before release of the drug.

Example 46

In Example 46, the effect of the addition of an extragranular excipient(s) to the delayed release coating of Example 2 was measured. In this example, the types of excipient added were Microcrystalline cellulose, Polyvinylpyrrolidone and Polyethylene glycol, and these excipients were added in levels of 0, 5% and 10%.

The ingredients of the inner core formulation of this Example is shown in Example 24 above, and the ingredients of the various delayed release coating granulation of this Example are shown in Example 2 above. The amounts or percentages of extragranular excipients added are set forth in Tables 46a and 46b below:

TABLE 46a

| | Control | | addition of 5% PVP | | addition of 10% PVP | |
|---|---|---|---|---|---|---|
| Formulation: | % | mg/tab | % | mg/tab | % | mg/tab |
| Core (Ex. 24) | 22.72% | 50 | 22.73% | 50 | 22.73% | 50 |
| Delayed release coating (Ex. 2) | 76.69% | 168.725 | 73% | 160.225 | 68.97% | 151.725 |
| Polyvinylpyrrolidone K-30 | Na | na | 3.86% | 8.5 | 7.73% | 17 |
| Polyethylene Glycol, 6000 | Na | na | Na | na | Na | na |
| Microcrystalline Cellulose | Na | na | Na | na | Na | na |
| Sodium Stearyl Fumarate | 0.58% | 1.275 | 0.58% | 1.275 | 0.58% | 1.275 |
| Tablet weight (mg) | | 220 | | 220 | | 220 |
| Tablet hardness (kP) | | 8-9 | | 8-9 | | 8-9 |

TABLE 46b

| Formulation: | addition of 5% PEG | | addition of 10% PEG | | addition of 5% MCC | | Addition of 10% MCC | |
|---|---|---|---|---|---|---|---|---|
| | % | mg/tab | % | mg/tab | % | mg/tab | % | mg/tab |
| Core (Ex. 24) | 22.73% | 50 | 22.73% | 50 | 22.73% | 50 | 22.73% | 50 |
| Delayed release coating (Ex. 2) | 73% | 160.225 | 68.97% | 151.725 | 73% | 160.225 | 68.97% | 151.725 |
| Polyvinylpyrolidone K-30 | na | na | Na | na | na | na | Na | na |
| Polyethylene Glycol, 6000 | 3.86% | 8.5 | 0.077272 | 17 | na | na | Na | na |
| Microcrystalline Cellulose | na | na | Na | na | 3.86% | 8.5 | 7.73% | 17 |
| Sodium Stearyl Fumarate | 0.58% | 1.275 | 0.58% | 1.275 | 0.58% | 1.275 | 0.58% | 1.275 |
| Tablet weight (mg) | | 220 | | 220 | | 220 | | 220 |
| Tablet hardness (kP) | | 8-9 | | 8-9 | | 8-9 | | 8-9 |

The effects of the addition of extragranular excipient to the sustained release coating are set forth in the table below.

TABLE 46c

| Control 220 mg tablet | | Addition of 5% PVP 220 mg tablet | | Addition of 10% PVP 220 mg tablet | | Addition of 5% MCC 220 mg tablet | |
|---|---|---|---|---|---|---|---|
| Time (hrs) | Normalized Mean | Time (hrs) | Normalized Mean | Time (hrs) | Normalized Mean | Time (hrs) | Normalized Mean |
| 0 | 0.0 | 0 | 0.0 | 0 | 0.0 | 0 | 0.0 |
| 4 | 0.0 | 2 | 0.0 | 2 | 0.0 | 8 | 0.0 |
| 6 | 0.0 | 4 | 0.0 | 4 | 0.0 | 9 | 0.0 |
| 8 | 0.0 | 6 | 0.0 | 6 | 0.0 | 10 | 0.0 |
| 10 | 0.0 | 8 | 0.0 | 8 | 0.0 | 11 | 0.0 |
| 12 | 33.3 | 10 | 0.0 | 10 | 16.7 | 12 | 0.0 |
| 16 | 100.0 | 12 | 16.7 | 14 | 100.0 | 14 | 42.4 |

| Addition of 10% MCC 220 mg tablet | | Addition of 5% PEG 220 mg tablet | | Addition of 10% PEG 220 mg tablet | |
|---|---|---|---|---|---|
| Time (hrs) | Normalized Mean | Time (hrs) | Normalized Mean | Time (hrs) | Normalized Mean |
| 0 | 0.0 | 0 | 0.0 | 0 | 0.0 |
| 2 | 0.0 | 8 | 0.0 | 8 | 0.0 |
| 4 | 0.0 | 9 | 1.8 | 9 | 0.0 |
| 6 | 0.0 | 10 | 1.8 | 10 | 22.1 |
| 8 | 0.0 | 11 | 41.8 | 11 | 83.3 |
| 10 | 0.0 | 12 | 61.8 | 12 | 100.0 |
| 14 | 100.0 | | | | |

In this example, it was observed that the addition of 5% and 10% Polyethylene Glycol 6000 served to slightly speed the release of active agent. Tablets with 5% PVP K-30 also show slightly shorter lag time compared to the control. The release speed and lag time of tablets with 10% PVP K-30 were unchanged. Tablets made with 10% MCC showed no change in lag time, although they were slower with 5% MCC. The conclusion reached is that lag time can be varied by the addition of extragranular additives into the sustained release coating.

Example 47

In Example 47, a scaled up production of the sustained release coating was done in order to determine whether tablets produced at production scale exhibit release profiles similar to those of tablets produced in laboratory scale.

In this example, the core-coated tablets were produced on a production press at Elizabeth Hata. A HT-AP44MSU-C 44 station core coating press was used to press the tablets. The inner cores of the tablets were made with a ¼" round flat face with a beveled edge, tableted to 170 mg and 8-10 kP. The final tablets were made 9 mm round concave, and were tableted to 525 and 560 mg, 8-10 kP.

The blends for the production scale were composed as follows:

| Inner Core blend: | Outer Coating blend: |
|---|---|
| 2% Prednisolone<br>40% Prosolv SMCC 50<br>47.75% Prosolv SMCC 90<br>6% Croscarmellose Sodium<br>2% Sodium Starch Glycolate<br>2% Talc<br>0.25% Sodium Stearyl Fumarate | Example 2 w/0.75% sodium stearyl fumarate |

In production of the tablets, the press speed varied from 9 to 12 rpm.

The effects of the scaled up production of the delayed release coating are shown in the data points for which are set forth in Table 47 below.

TABLE 47

| Production scale 525 mg tablet weight | | Production Scale 560 mg tablet weight | |
|---|---|---|---|
| Time (hours) | Normalized Mean | Time (hours) | Normalized Mean |
| | 0.0 | 0 | 0.0 |
| 13.5 | 23.7 | 12 | 10.1 |
| 14 | 38.2 | 13 | 10.7 |
| 14.5 | 65.0 | 14 | 35.4 |
| 15 | 72.9 | 15 | 65.0 |
| 15.5 | 85.7 | 16 | 79.0 |
| 16 | 100.0 | 17 | 100.0 |

In this example, it was observed that tablets produced at production scale exhibit similar release profiles to tablets produced at laboratory scale. Accordingly, the conclusion reached is that formulation and production technology can be successfully scaled up.

Example 48-57

In Examples 48-57, prednisolone tablets were prepared having core formulations with different amounts of disintegrants and coating formulations as described Example 10. Each tablet had the same core weight, same coating weight, and the same total tablet weight. The tablet formulations of Examples 48-57 are listed in Tables 48 and 49 below:

TABLE 48

| Component | Ex. 48 | Ex. 49 | Ex. 50 | Ex. 51 | Ex. 52 |
|---|---|---|---|---|---|
| Core formulation used | Ex. 25 core | Ex. 28 core | Ex. 26 core | Ex. 27 core | Ex. 31 core |
| Disintegrant | none | 2% Ac-Di-Sol | 3% Explotab | 3% Explotab and 2% Ac-Di-Sol | 6% Ac-Di-Sol |
| | amt. (mg) | amt. (mg) | amt. (mg) | amt. (mg) | amt. (mg) |
| 1. Core | 50 | 50 | 50 | 50 | 50 |
| 2. Example 10 coating | 450 | 450 | 450 | 450 | 450 |
| Total tablet weight | 500 | 500 | 500 | 500 | 500 |

TABLE 49

| Component | Ex. 53 | Ex. 54 | Ex. 55 | Ex. 56 | Ex. 57 |
|---|---|---|---|---|---|
| Core formulation used | Ex. 29 core | Ex. 29 core | Ex. 31 core | Ex. 30 core | Ex. 32 core |
| Disintegrant | 2% Explotab V17 and 6% Ac-Di-Sol | 2% Explotab V17 and 6% Ac-Di-Sol | 6% Ac-Di-Sol | 20% Explotab | 20% Explotab |
| | amt. (mg) | amt. (mg) | amt. (mg) | amt. (mg) | amt. (mg) |
| 1. Core | 50 | 50 | 50 | 50 | 50 |
| 2. Example 10 coating | 450 | 450 | 450 | 450 | 450 |
| Total tablet weight | 500 | 500 | 500 | 500 | 500 |

The tablets of Examples 48-57 were tested using USP dissolution apparatus type III with 250 mL DI water at 15 dips per minute (dpm) giving the following results listed in Table 50:

TABLE 50

| | Time (hours) | | | | | | | | |
|---|---|---|---|---|---|---|---|---|---|
| | 0 | 3 | 4 | 4.5 | 5 | 5.5 | 6 | 6.5 | 7 | 8 |
| Example 48 % dissolved | 0 | 0 | 0 | — | 0 | — | 8.3 | — | 12 | 12 |
| Example 49 % dissolved | 0 | 0 | 0 | — | 73.7 | — | 100 | — | 100 | 100 |
| Example 50 % dissolved | 0 | 0 | 0 | — | 78.3 | — | 100 | — | 100 | 100 |
| Example 51 % dissolved | 0 | 0 | 0 | — | 14.9 | — | 100 | — | 100 | 100 |
| Example 52 % dissolved | 0 | 0 | 0 | — | 0 | — | 65.8 | — | 100 | 100 |
| Example 53 % dissolved | 0 | 0 | 0 | — | 2.7 | — | 96.8 | — | 100 | 100 |
| Example 54 % dissolved | 0 | — | 9.2 | 56.9 | 100 | 100 | 100 | 100 | — | — |
| Example 55 % dissolved | 0 | — | 17.3 | 50.6 | 64.6 | 66.7 | 100 | 100 | — | — |
| Example 56 % dissolved | 0 | 0 | 0 | 0 | 14.9 | 40.8 | 60.6 | — | — | — |
| Example 57 % dissolved | 0 | 0 | 0 | — | 0 | — | 66.7 | — | 100 | 100 |

The results indicated that the inclusion of a disintegrant in the core can lead to a more rapid release of the active agent from the formulation.

Examples 58-60

In Examples 58-60, prednisolone tablets were prepared having core formulations of Example 24 and coating formulations as described Examples 2, 4, and a combination Examples 2 and 4 (25% of Example 2 and 75% of Example 4). Each tablet had the same core weight, same coating weight, and the same total tablet weight. The tablet formulations of Examples 58-60 are listed in Table 51 below:

TABLE 51

| Component | Ex. 58 amt. (mg) | Ex. 59 amt. (mg) | Ex. 60 amt. (mg) |
|---|---|---|---|
| 1. Core (Ex. 24) | 50 | 50 | 50 |
| 2. Example 2 coating | 250 | — | — |
| 3. Example 4 coating | — | 250 | — |
| 4. Coating consisting of 25% of Example 2 and 75% of Example 4 coatings | — | — | 250 |
| Total tablet weight | 300 | 300 | 300 |

Tablets having the formulations described in Examples 58-60 were subjected to dissolution testing using the USP apparatus type 3 with 250 ml DI water at 15 dips per minute. The results are set forth in Table 52 below.

TABLE 52

| Ex. 58 | | Ex. 59 | | Ex. 60 | |
|---|---|---|---|---|---|
| Time (hr) | % Dissolved | Time (hr) | % Dissolved | Time (hr) | % Dissolved |
| 0 | 0 | 0 | 0 | 0 | 0 |
| 8 | 3 | 2 | 0 | 4 | 0.3 |
| 10 | 6.9 | 3 | 0 | 6 | 4 |
| 12 | 23.8 | 4 | 59.4 | 8 | 39.6 |
| 14 | 52.3 | 5 | 99.6 | 10 | 99.4 |
| 16 | 99 | 6 | 100 | 12 | 100 |
| 20 | 100 | 7 | 100 | 14 | 100 |

Example 61

In Example 61, prednisolone tablets having the formulations described in Examples 59 were subjected to dissolution variations in pH, ionic strength, and dip rates. The pH evaluated was 1.5, 7.5 and pH change.

The pH change method uses increasing pH from one dissolution vessel to the next to simulate the transport of the dosage form through the gastrointestinal tract. Initially the pH is 1.5 for 1 hour. The pH of the second station is 3.5 for two additional hours and then the third station is 5.5 for an additional 2 hours. Finally the last three stations are at pH 7.5. The time length for the last three stations can vary depending on the expected release for the dosage form.

The results are set forth in Tables 53 and 54 below. The results indicate that the dissolution profiles for a formulation prepared in accordance with Example 59 where the dissolution media pH and ionic strength were varied.

TABLE 53

| Time | pH 1.5 (0.25 M) | pH 7.5 (0.01 M) | pH 7.5 (0.1 M) | pH 7.5 (0.25 M) | pH Change (0.1 M) |
|---|---|---|---|---|---|
| 0 | 0 | 0 | 0 | 0 | 0 |
| 1 | 0 | 0 | 0 | 0 | 0 |
| 3 | 9.3 | 98.1 | 5.9 | 3 | 0 |
| 5 | 20.8 | 100 | 28.9 | 8.8 | 0 |
| 10 | 44.6 | 100 | 88.1 | 42.8 | 11.2 |
| 15 | 87.9 | 100 | 92 | 93.9 | 70 |
| 20 | 100 | 100 | 100 | 95 | 100 |

TABLE 54

| Time | pH Change No Ions |
|---|---|
| 0 | 0 |
| 1 | 0 |
| 3 | 0 |
| 5 | 0 |
| 7 | 7.7 |
| 9 | 17.7 |
| 11 | 100 |

The results set forth in Tables 55 and 56 below provide the normalized mean dissolution profiles for a formulation prepared in accordance with Example 59 using the pH change method (0.1M) at 15 and 30 dpm, respectively.

TABLE 55

Normalized mean values using pH change method (0.1M) at 15 dpm

| Normalized Mean | Normalized SD | Normalized % CV |
|---|---|---|
| 0.0 | 0.0 | #DIV/0! |
| 0.0 | 0.0 | #DIV/0! |
| 0.0 | 0.0 | #DIV/0! |
| 0.0 | 0.0 | #DIV/0! |
| 11.2 | 0.7 | 6.0 |
| 70.0 | 36.7 | 52.4 |
| 100.0 | 0.0 | 0.0 |

TABLE 56

Normalized mean values using pH change method (0.1M) at 30 dpm

| Normalized Mean | Normalized SD | Normalized % CV |
|---|---|---|
| 0.0 | 0.0 | #DIV/0! |
| 0.0 | 0.0 | #DIV/0! |
| 0.0 | 0.0 | #DIV/0! |
| 16.7 | 40.8 | 244.9 |
| 100.0 | 0.0 | 0.0 |
| 100.0 | 0.0 | 0.0 |
| 100.0 | 0.0 | 0.0 |

Example 62

In Example 62, a 2 mg prednisolone core composition was prepared similarly to Example 24, increasing the amount of prednisolone in the core and decreasing the amount of Prosolve SMCC 90, and having the following formulation listed in Table 57:

TABLE 57

| Component | Percent | amt. (mg) |
|---|---|---|
| 1. Prednisolone | 4 | 2.0 |
| 2. Prosolv SMCC ™ 50 | 40 | 20.0 |
| 3. Prosolv SMCC ™ 90 | 45.75 | 22.875 |
| 4. Explotab ® | 6 | 3.0 |
| 5. Sodium carboxymethylcellulose | 2 | 1.0 |
| 6. Talc | 2 | 1.0 |
| 7. Pruv | 0.25 | 0.125 |
| Total | 100 | 50 |
| Core size and shape | 3/16 Round SC | |

Example 63-68

In Examples 63-68, the core formulation of Example 62 was coated with coatings prepared in accordance with Examples 11, 12, 13, 14, 15, and 16. The formulations of Examples are listed in Table 58 below:

TABLE 58

| Component | Ex. 63 amt. (mg) | Ex. 64 amt. (mg) | Ex. 65 amt. (mg) | Ex. 66 amt. (mg) | Ex. 67 amt. (mg) | Ex. 68 amt. (mg) |
|---|---|---|---|---|---|---|
| 1. Core (Ex. 62) | 50 | 50 | 50 | 50 | 50 | 50 |
| 2. Ex. 11 coating | 250 | — | — | — | — | — |
| 3. Ex. 12 coating | — | 250 | — | — | — | — |
| 4. Ex. 13 coating | — | — | 250 | — | — | — |
| 5. Ex. 14 coating | — | — | — | 250 | — | — |
| 6. Ex. 15 coating | — | — | — | — | 250 | — |
| 7. Ex. 16 coating | — | — | — | — | — | 250 |
| Total tablet weight | 300 | 300 | 300 | 300 | 300 | 300 |

Dissolution testing was done on each formulation using USP apparatus 3 with 250 ml of media and 15 dpm. Two dissolution methods using different media (1) DI water and (2) pH change were performed. Table 59 provides the DI water dissolution results, and Table 60 provides the pH change (0.1M) dissolution results.

TABLE 59

| Time (hr.) | Ex. 63 (30% Gums) | Ex. 64 (22.5% Gums) | Ex. 65 (20% Gums) | Ex. 66 (15% Gums) | Ex. 67 (10% Gums) | Ex. 68 (7.5% Gums) |
|---|---|---|---|---|---|---|
| 0 | 0 | 0 | 0 | 0 | 0 | 0 |
| 1 | 0 | 1.2 | 0 | 0 | 0 | 0 |
| 1.5 | 0 | 33.4 | 0 | 30.8 | 64.5 | 98.8 |
| 2 | 30.1 | 98.6 | 64.5 | 99.3 | 98.4 | 100 |
| 2.5 | 98.7 | 100 | 99.5 | 100 | 100 | 100 |
| 3 | 100 | 100 | 100 | 100 | 100 | 100 |
| 3.5 | 100 | 100 | 100 | 100 | 100 | 100 |

TABLE 60

| Time (hr.) | Ex. 63 (30% Gums) | Ex. 64 (22.5% Gums) | Ex. 65 (20% Gums) | Ex. 66 (15% Gums) | Ex. 67 (10% Gums) | Ex. 68 (7.5% Gums) |
|---|---|---|---|---|---|---|
| 0 | 0 | 0 | 0 | 0 | 0 | 0 |
| 1 | 0 | 0.8 | 0 | 0 | 0 | 32 |
| 3 | 5.8 | 1 | 0 | 0.8 | 0.7 | 98.9 |
| 5 | 6.7 | 3.4 | 3.3 | 5.6 | 91.3 | 100 |
| 8 | 10.8 | 19.4 | 11 | 96.8 | 100 | 100 |
| 11 | 15.7 | 37.6 | 69.5 | 100 | 100 | 100 |
| 14 | 67.8 | 93 | 100 | 100 | 100 | 100 |

Analysis of the data allows for the approximation of the lag time based a linear fit of the data obtained. The data demonstrates the lag time can be varied from 0 to 8 hours depending on gum level in the formulation. Table 61 is a summary of the Example and gum ratio (%) used and the approximated lag time before release.

TABLE 61

Approximated Lag Time Before Release

| Example Number | Gum Ratio (%) | Lag Time (Hours) |
|---|---|---|
| 68 | 7.5 | 0.7 |
| 67 | 10.0 | 1.7 |
| 66 | 15.0 | 3.6 |
| 65 | 20.0 | 5.0 |
| 64 | 22.5 | 7.4 |
| 63 | 30.0 | 9.2 |

Example 69

In Example 69, other formulations were prepared and tested using USP apparatus Type 3, with 250 ml of the dissolution media and dips per minute as indicated in the Table 62.

The particular dissolution media are defined as follows:

| | |
|---|---|
| DI water: | USP purified water; |
| pH change or pH change NI ("no ion"): | pH change method as described in Example 61, without the use of ions to change adjust the pH; |
| pH change (0.1M): | pH change method as described in Example 61 with the use of salts to give an ionic strength of 0.1molar; |
| pH 7.5: | dissolution media having a pH of 7.5; |
| pH 7.5 (0.1M): | dissolution media having a pH of 7.5 and ionic strength of 0.1M; |
| SGI: | simulated gastric fluid; |
| Peanut oil pH 7.5: | peanut oil with a pH of 7.5; |

Other dissolution media indicated would be readily understood by those skilled in the art (e.g., pH 1.5:dissolution media having a pH of 1.5, etc.) in view of the above.

With respect to certain excipients indicated in the comments section, these excipients have been added to the compression coating prior to coating the cores.

TABLE 62

| Test | Coating Example | Core Example | Coating Amount (mg) | Tablet Weight (mg) | Coating Size (in.) | Dissolution Media | Dissol dpm | Dissolution Time (hrs) (shaded) vs. % Dissolved | | | | | | |
|---|---|---|---|---|---|---|---|---|---|---|---|---|---|---|
| | | | | | | | | 0 | 1 | 2 | 3 | 4 | 5 | 6 |
| 1 | Ex. 14 | Ex. 22 | 250 | 300 | 5/16 | DI Water | 15 | 0 | 0 | 100 | 100 | 100 | 100 | 100 |
| | | | | | | | | 0 | 1 | 3 | 5 | 7 | 9 | 11 |
| 2 | Ex. 14 | Ex. 22 | 250 | 300 | 5/16 | pH Change NI | 15 | 0 | 0 | 33 | 100 | 100 | 100 | 100 |
| | | | | | | | | 0 | 1 | 3 | 5 | 7 | 9 | 11 |
| 3 | Ex. 14 | Ex. 22 | 250 | 300 | 5/16 | pH Change (0.1 M) | 15 | 0 | 0 | 0.8 | 15 | 90 | 100 | 100 |
| | | | | | | | | 0 | 2 | 4 | 6 | 8 | 10 | 12 |
| 4 | Ex. 14 | Ex. 22 | 250 | 300 | 5/16 | pH 1.5 | 15 | 0 | 0 | 6.3 | 81 | 98 | 100 | 100 |
| | | | | | | | | 0 | 2 | 4 | 6 | 8 | 10 | 12 |
| 5 | Ex. 14 | Ex. 22 | 250 | 300 | 5/16 | pH 7.5 | 15 | 0 | 0 | 0 | 56 | 95 | 100 | 100 |
| | | | | | | | | 0 | 2 | 4 | 6 | 8 | 10 | 12 |
| 6 | Ex. 14 | Ex. 22 | 180 | 230 | 5/16 | pH 1.5 (0.1 M) | 15 | 0 | 0 | 11 | 98 | 100 | 100 | 100 |
| | | | | | | | | 0 | 1 | 3 | 55 | 7 | 9 | 11 |
| 7 | Ex. 14 | Ex. 22 | 180 | 230 | 5/16 | pH Change | 15 | 0 | 0 | 0 | 81 | 100 | 100 | 100 |
| | | | | | | | | 0 | 1 | 2 | 3 | 4 | 5 | 6 |
| 8 | Ex. 14 | Ex. 22 | 180 | 230 | 5/16 | DI Water | 15 | 0 | 0 | 83 | 100 | 100 | 100 | 100 |
| | | | | | | | | 0 | 4 | 5 | 6 | 7 | 8 | 10 |
| 9 | 75% Ex. 2 and 25% Ex. 4 | Ex. 22 | 250 | 300 | 5/16 | DI Water | 15 | 0 | 0 | 0.9 | 17.1 | 65.1 | 85.8 | 100 |
| | | | | | | | | 0 | 1 | 2 | 3 | 4 | 5 | 6 |
| 10 | 75% Ex. 2 and 25% Ex. 4 | Ex. 22 | 250 | 300 | 5/16 | DI Water | 30 | 0 | 0 | 50 | 82 | 100 | 100 | 100 |
| | | | | | | | | 0 | 4 | 6 | 8 | 10 | 12 | 14 |
| 11 | 75% Ex. 2 and 25% Ex. 4 | Ex. 22 | 250 | 300 | 5/16 | DI Water | 5 | 0 | 0 | 0 | 0 | 0 | 2.7 | 7.8 |
| | | | | | | | | 0 | 2 | 4 | 6 | 8 | 10 | 12 |
| 12 | 75% Ex. 2 and 25% Ex. 4 | Ex. 22 | 250 | 300 | 5/16 | pH 7.5 (0.1 M) | 15 | 0 | 0 | 0 | 0 | 0 | 0 | 0 |
| | | | | | | | | 0 | 4 | 8 | 12 | 16 | 20 | 24 |
| 13 | 75% Ex. 2 and 25% Ex. 4 | Ex. 22 | 250 | 230 | 5/16 | pH 7.5 (0.01 M) | 15 | 0 | 0 | 50 | 100 | 100 | 100 | 100 |
| | | | | | | | | 0 | 2 | 3 | 4 | 5 | 6 | 7 |
| 14 | 75% Ex. 2 and 25% Ex. 4 | Ex. 24 | 250 | 230 | 5/16 | DI Water | 15 | 0 | 0 | 0 | 7.5 | 16.7 | 35.4 | 50 |
| | | | | | | | | 0 | 4 | 5 | 6 | 7 | 8 | 10 |
| 15 | 75% Ex. 2 and 25% Ex. 4 | Ex. 22 | 250 | 300 | 5/16 | Peanut Oil | 15 | 0 | 0 | 0.4 | 80 | 86 | 100 | 100 |

TABLE 62-continued

| # | Sample | Other | A | B | C | Medium | T | 0 | | | | | | |
|---|---|---|---|---|---|---|---|---|---|---|---|---|---|---|
| | | | | | | | | 0 | 4 | 5 | 6 | 7 | 8 | 10 |
| 16 | 75% Ex. 2 and 25% Ex. 4 | Ex. 24 | 250 | 300 | 5/16 | DI Water | 15 | 0 | 0 | 0 | 3.7 | 55.8 | 77.8 | 100 |
| | | | | | | | | 0 | 2 | 4 | 6 | 8 | 10 | 12 |
| 17 | Ex. 2 | Ex. 24 | 170 | 220 | 9/32 | DI Water | 15 | 0 | 0 | 0 | 0 | 0 | 0 | 17 |
| | | | | | | | | 0 | 2 | 4 | 6 | 8 | 10 | 12 |
| 18 | Ex. 2 | Ex. 24 | 170 | 220 | 9/32 | DI Water | 15 | 0 | 0 | 0 | 0 | 0 | 17 | 100 |
| | | | | | | | | 0 | 2 | 4 | 6 | 8 | 10 | 14 |
| 19 | Ex. 2 | Ex. 24 | 170 | 220 | 9/32 | DI Water | 15 | 0 | 0 | 0 | 0 | 0 | 0 | 100 |
| | | | | | | | | 0 | 2 | 4 | 6 | 8 | 10 | 14 |
| 20 | Ex. 2 | Ex. 24 | 170 | 220 | 9/32 | DI Water | 15 | 0 | 0 | 0 | 0 | 0 | 0 | 42 |
| | | | | | | | | 0 | 8 | 9 | 10 | 11 | 12 | 14 |
| 21 | Ex. 2 | Ex. 24 | 170 | 220 | 9/32 | DI Water | 15 | 0 | 0 | 0 | 22 | 84 | 100 | 100 |
| | | | | | | | | 0 | 8 | 9 | 10 | 11 | 12 | 14 |
| 22 | Ex. 2 | Ex. 24 | 170 | 220 | 9/32 | DI Water | 15 | 0 | 0 | 1.8 | 1.8 | 42 | 62 | 100 |
| | | | | | | | | 0 | 16 | 18 | 20 | 22 | 24 | 26 |
| 23 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 24 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 25 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 26 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 27 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 28 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 29 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 30 | Ex. 10 | Ex. 24 | 450 | 500 | 3/8 | pH 1.5 | 15 | 0 | 0 | 0 | 0 | 0 | 0 | 0 |
| | | | | | | | | 0 | 6 | 8 | 10 | 12 | 14 | 16 |
| 31 | Ex. 10 | Ex. 24 | 450 | 500 | 3/8 | pH 1.5 | 15 | 0 | 0 | 0 | 0 | 0 | 0 | 0 |

TABLE 62-continued

| # | A | B | 450 | 500 | 3/8 | Medium | 15 | Data |
|---|---|---|---|---|---|---|---|---|
| 32 | Ex. 6 | Ex. 24 | 450 | 500 | 3/8 | DI Water | 15 | 0/0, 8/1.6, 10/6.9, 12/13, 14/46, 16/67, 18/100 |
| 33 | Ex. 6 | Ex. 24 | 450 | 500 | 3/8 | DI Water | 15 | 0/0, 8/0, 10/0, 12/0, 14/3.3, 16/4.9, 18/37 |
| 34 | Ex. 6 | Ex. 24 | 450 | 500 | 3/8 | DI Water | 15 | 0/0, 8/0, 10/0, 12/0, 14/0, 16/2.3, 18/— |
| 35 | Ex. 6 | Ex. 24 | 450 | 500 | 3/8 | DI Water | 15 | 0/0, 8/0, 10/0, 12/0, 14/0, 16/64, 18/67 |
| 36 | Ex. 6 | Ex. 24 | 450 | 500 | 3/8 | DI Water | 15 | 0/0, 8/4.8, 10/10, 12/16, 14/56, 16/99, 18/100 |
| 37 | Ex. 6 | Ex. 24 | 450 | 500 | 3/8 | DI Water | 15 | 0/0, 8/4.8, 10/10, 12/16, 14/56, 16/99, 18/100 |
| 38 | Ex. 6 | Ex. 24 | 450 | 500 | 3/8 | DI Water | 15 | 0/0, 10/7.3, 14/17, 16/47, 18/62, 20/99, 22/100 |
| 39 | Ex. 10 | Ex. 24 | 450 | 500 | 3/8 | DI Water | 15 | 0/0, 12/2.9, 14/5.1, 16/7.6, 18/10, 20/27, 24/73 |
| 40 | Ex. 10 | Ex. 24 | 450 | 500 | 3/8 | DI Water | 15 | 0/0, 1/0, 2/0.5, 3/0.5, 4/0.5, 5/99, 6/100 |
| 41 | Ex. 6 | Ex. 24 | 450 | 500 | 3/8 | DI Water | 15 | 0/0, 10/4.1, 14/13, 16/40, 18/69, 20/83, 22/83 |
| 42 | Ex. 10 | Ex. 25 | 450 | 500 | 3/8 | DI Water | 15 | 0/0, 3/0, 4/0, 5/0, 6/8.3, 7/12, 8/12 |
| 43 | Ex. 10 | Ex. 25 | 450 | 500 | 3/8 | pH 1.5 | 15 | 0/0, 4/0, 8/0, 12/0, 16/0, 20/0, 24/14 |
| 44 | Ex. 10 | Ex. 28 | 450 | 500 | 3/8 | DI Water | 15 | 0/0, 3/0, 4/0, 5/74, 6/100, 7/100, 8/100 |
| 45 | Ex. 10 | Ex. 26 | 450 | 500 | 3/8 | DI Water | 15 | 0/0, 3/0, 4/0, 5/78, 6/100, 7/100, 8/100 |
| 46 | Ex. 10 | Ex. 28 | 450 | 500 | 3/8 | pH 1.5 | 15 | 0/0, 4/0, 8/0, 12/0, 16/0, 20/0, 24/29 |
| 47 | Ex. 10 | Ex. 26 | 450 | 500 | 3/8 | pH 1.5 | 15 | 0/0, 4/0, 8/0, 12/0, 16/0, 20/0, 24/16 |

TABLE 62-continued

| 48 | Ex. 10 | Ex. 27 | 450 | 500 | 3/8 | DI Water | 15 | 0 | 3 | 4 | 5 | 6 | 7 | 8 |
|----|--------|--------|-----|-----|-----|----------|----|---|---|---|---|---|---|---|
|    |        |        |     |     |     |          |    | 0 | 0 | 0 | 15 | 100 | 100 | 100 |

| 49 | Ex. 2 | Ex. 27 | 250 | 300 | 5/16 | DI Water | 15 | 0 | 4 | 6 | 8 | 10 | 12 | 16 |
|----|-------|--------|-----|-----|------|----------|----|---|---|---|---|----|----|----|
|    |       |        |     |     |      |          |    | 0 | 0 | 0 | 0 | 0 | 16 | 100 |

| 50 | Ex. 2 | Ex. 28 | 250 | 300 | 5/16 | DI Water | 15 | 0 | 4 | 6 | 8 | 10 | 12 | 16 |
|----|-------|--------|-----|-----|------|----------|----|---|---|---|---|----|----|----|
|    |       |        |     |     |      |          |    | 0 | 0 | 0.5 | 0.5 | 0.5 | 0.5 | 38 |

| 51 | Ex. 2 | Ex. 27 | 250 | 300 | 5/16 | pH 1.5 | 15 | 0 | 4 | 8 | 12 | 16 | 20 | 24 |
|----|-------|--------|-----|-----|------|--------|----|---|---|---|----|----|----|----|
|    |       |        |     |     |      |        |    | 0 | 0 | 0 | 0 | 0 | 0 | 12 |

| 52 | Ex. 2 | Ex. 28 | 250 | 300 | 5/16 | pH 1.5 | 15 | 0 | 4 | 8 | 12 | 16 | 20 | 24 |
|----|-------|--------|-----|-----|------|--------|----|---|---|---|----|----|----|----|
|    |       |        |     |     |      |        |    | 0 | 0 | 0 | 0 | 0 | 0 | 15 |

| 53 | Ex. 10 | Ex. 27 | 450 | 500 | 3/8 | pH 1.5 | 15 | 0 | 4 | 8 | 12 | 16 | 20 | 24 |
|----|--------|--------|-----|-----|-----|--------|----|---|---|---|----|----|----|----|
|    |        |        |     |     |     |        |    | 0 | 0 | 0 | 0 | 0 | 1.9 | 26 |

| 54 | Ex. 10 | Ex. 31 | 450 | 500 | 3/8 | DI Water | 15 | 0 | 4 | 4.5 | 5 | 5.5 | 6 | 7 |
|----|--------|--------|-----|-----|-----|----------|----|---|---|-----|---|-----|---|---|
|    |        |        |     |     |     |          |    | 0 | 8.6 | 25.3 | 32.3 | 66.7 | 82.9 | 100 |

| 55 | Ex. 10 | Ex. 29 | 450 | 500 | 3/8 | DI Water | 15 | 0 | 3 | 4 | 5 | 6 | 7 | 24 |
|----|--------|--------|-----|-----|-----|----------|----|---|---|---|---|---|---|----|
|    |        |        |     |     |     |          |    | 0 | 0 | 0 | 2.7 | 97 | 100 | 100 |

| 56 | Ex. 10 | Ex. 31 | 450 | 500 | 3/8 | pH Change | 15 | 0 | 2 | 4 | 6 | 8 | 12 | 20 |
|----|--------|--------|-----|-----|-----|-----------|----|---|---|---|---|---|----|----|
|    |        |        |     |     |     |           |    | 0 | 0 | 0 | 0 | 0 | 0 | 16 |

| 57 | Ex. 10 | Ex. 29 | 450 | 500 | 3/8 | pH Change | 15 | 0 | 2 | 4 | 5 | 6 | 12 | 20 |
|----|--------|--------|-----|-----|-----|-----------|----|---|---|---|---|---|----|----|
|    |        |        |     |     |     |           |    | 0 | 0 | 0 | 0 | 0 | 0 | 18 |

| 58 | Ex. 10 | Ex. 29 | 450 | 500 | 3/8 | pH Change | 15 | 0 | 2 | 4 | 6 | 18 | 22 | 26 |
|----|--------|--------|-----|-----|-----|-----------|----|---|---|---|---|----|----|----|
|    |        |        |     |     |     |           |    | 0 | 0 | 0 | 0 | 19 | 19 | 88 |

| 59 | Ex. 10 | Ex. 18 | 450 | 500 | 3/8 | DI Water | 15 | 0 | 4 | 4.5 | 5 | 5.5 | 6 | 6.5 |
|----|--------|--------|-----|-----|-----|----------|----|---|---|-----|---|-----|---|-----|
|    |        |        |     |     |     |          |    | 0 | 9.2 | 57 | 100 | 100 | 100 | 100 |

| 60 | Ex. 10 | Ex. 31 | 450 | 500 | 3/8 | pH Change | 15 | 0 | 2 | 4 | 6 | 18 | 22 | 26 |
|----|--------|--------|-----|-----|-----|-----------|----|---|---|---|---|----|----|----|
|    |        |        |     |     |     |           |    | 0 | 0 | 0 | 0 | 19 | 19 | 23 |

| 61 | Ex. 10 | Ex. 31 | 450 | 500 | 3/8 | DI Water | 15 | 0 | 3 | 4 | 4.5 | 5 | 5.5 | 6 |
|----|--------|--------|-----|-----|-----|----------|----|---|---|---|-----|---|-----|---|
|    |        |        |     |     |     |          |    | 0 | 0 | 0 | 0 | 15 | 41 | 61 |

| 62 | Ex. 10 | Ex. 31 | 450 | 500 | 3/8 | pH Change | 15 | 0 | 2 | 4 | 6 | 16 | 20 | 24 |
|----|--------|--------|-----|-----|-----|-----------|----|---|---|---|---|----|----|----|
|    |        |        |     |     |     |           |    | 0 | 0 | 0 | 0 | 0 | 33 | 33 |

| 63 | Ex. 10 | Ex. 31 | 450 | 500 | 3/8 | pH Change | 15 | 0 | 2 | 4 | 6 | 16 | 20 | 24 |
|----|--------|--------|-----|-----|-----|-----------|----|---|---|---|---|----|----|----|
|    |        |        |     |     |     |           |    | 0 | 0 | 0 | 0 | 0 | 33 | 100 |

TABLE 62-continued

| 64 | Ex. 10 | Ex. 31 | 450 | 500 | 3/8 | pH Change | 15 | 0 | 2 | 4 | 6 | 16 | 20 | 24 |
|----|--------|--------|-----|-----|-----|-----------|----|---|---|---|---|----|----|----|
|    |        |        |     |     |     |           |    | 0 | 0 | 0 | 0 | 11 | 13 | 48 |

| 65 | Ex. 10 | Ex. 29 | 450 | 500 | 3/8 | pH Change | 15 | 0 | 2 | 4 | 6 | 16 | 20 | 24 |
|----|--------|--------|-----|-----|-----|-----------|----|---|---|---|---|----|----|----|
|    |        |        |     |     |     |           |    | 0 | 0 | 0 | 0 | 11 | 11 | 69 |

| 66 | Ex. 10 | Ex. 31 | 450 | 500 | 3/8 | DI Water  | 15 | 0 | 3 | 4 | 5 | 6  | 7   | 8   |
|----|--------|--------|-----|-----|-----|-----------|----|---|---|---|---|----|-----|-----|
|    |        |        |     |     |     |           |    | 0 | 0 | 0 | 0 | 67 | 100 | 100 |

| 67 | Ex. 10 | Ex. 35 | 450 | 500 | 3/8 | pH Change | 15 | 0 | 2 | 4 | 6 | 16  | 20 | 24  |
|----|--------|--------|-----|-----|-----|-----------|----|---|---|---|---|-----|----|-----|
|    |        |        |     |     |     |           |    | 0 | 0 | 0 | 0 | 7.1 | 37 | 100 |

| 68 | Ex. 10 | Ex. 32 | 450 | 500 | 3/8 | pH Change | 15 | 0 | 2 | 4 | 6 | 16  | 20 | 24  |
|----|--------|--------|-----|-----|-----|-----------|----|---|---|---|---|-----|----|-----|
|    |        |        |     |     |     |           |    | 0 | 0 | 0 | 0 | 150 | 28 | 100 |

| 69 | Ex. 10 | Ex. 34 | 450 | 500 | 3/8 | pH Change | 15 | 0 | 2 | 4 | 6 | 16 | 20 | 24 |
|----|--------|--------|-----|-----|-----|-----------|----|---|---|---|---|----|----|----|
|    |        |        |     |     |     |           |    | 0 | 0 | 0 | 0 | 0  | 18 | 70 |

| 70 | Ex. 10 | Ex. 24 | 450 | 500 | 3/8 | pH 1.5    | 15 | 0 | 3 | 4 | 5 | 6 | 7 | 8 |
|----|--------|--------|-----|-----|-----|-----------|----|---|---|---|---|---|---|---|
|    |        |        |     |     |     |           |    | 0 | 0 | 0 | 0 | 0 | 0 | 0 |

| 71 | Ex. 10 | Ex. 24 | 450 | 500 | 3/8 | pH 5.5    | 15 | 0 | 2 | 3 | 4 | 5  | 6   | 7   |
|----|--------|--------|-----|-----|-----|-----------|----|---|---|---|---|----|-----|-----|
|    |        |        |     |     |     |           |    | 0 | 0 | 0 | 0 | 52 | 100 | 100 |

| 72 | Ex. 10 | Ex. 24 | 450 | 500 | 3/8 | pH 7.5        | 15 | 0 | 2 | 3 | 4 | 5  | 6   | 7   |
|----|--------|--------|-----|-----|-----|---------------|----|---|---|---|---|----|-----|-----|
|    |        |        |     |     |     |               |    | 0 | 0 | 0 | 0 | 20 | 100 | 100 |

| 73 | Ex. 10 | Ex. 24 | 450 | 500 | 3/8 | pH 7.5 Buffer | 15 | 0 | 2 | 3 | 4 | 5 | 6 | 7 |
|----|--------|--------|-----|-----|-----|---------------|----|---|---|---|---|---|---|---|
|    |        |        |     |     |     |               |    | 0 | 0 | 0 | 0 | 0 | 0 | 0 |

| 74 | Ex. 10 | Ex. 24 | 450 | 500 | 3/8 | pH 3.5    | 15 | 0 | 3 | 4 | 5 | 6  | 7  | 8   |
|----|--------|--------|-----|-----|-----|-----------|----|---|---|---|---|----|----|-----|
|    |        |        |     |     |     |           |    | 0 | 0 | 0 | 0 | 65 | 95 | 100 |

| 75 | Ex. 10 | Ex. 24 | 450 | 500 | 3/8 | pH 5.5    | 15 | 0 | 3 | 4 | 5 | 6   | 7   | 8   |
|----|--------|--------|-----|-----|-----|-----------|----|---|---|---|---|-----|-----|-----|
|    |        |        |     |     |     |           |    | 0 | 0 | 0 | 0 | 100 | 100 | 100 |

| 76 | Ex. 10 | Ex. 24 | 450 | 500 | 3/8 | pH Change | 15 | 0 | 1 | 3 | 5 | 7 | 9  | 11  |
|----|--------|--------|-----|-----|-----|-----------|----|---|---|---|---|---|----|-----|
|    |        |        |     |     |     |           |    | 0 | 0 | 0 | 0 | 0 | 78 | 100 |

| 77 | Ex. 10 | Ex. 24 | 450 | 500 | 3/8 | SGI       | 15 | 0 | 3 | 4 | 5 | 6 | 7 | 8 |
|----|--------|--------|-----|-----|-----|-----------|----|---|---|---|---|---|---|---|
|    |        |        |     |     |     |           |    | 0 | 0 | 0 | 0 | 0 | 0 | 0 |

| 78 | Ex. 10 | Ex. 24 | 450 | 500 | 3/8 | pH 1.5    | 15 | 0 | 8 | 10 | 12 | 14 | 16 | 18 |
|----|--------|--------|-----|-----|-----|-----------|----|---|---|----|----|----|----|----|
|    |        |        |     |     |     |           |    | 0 | 0 | 0  | 0  | 0  | 0  | 57 |

| 79 | Ex. 10 | Ex. 24 | 450 | 500 | 3/8 | pH 1.5    | 30 | 0 | 8 | 10 | 12 | 14 | 16 | 18  |
|----|--------|--------|-----|-----|-----|-----------|----|---|---|----|----|----|----|-----|
|    |        |        |     |     |     |           |    | 0 | 0 | 0  | 49 | 49 | 49 | 100 |

TABLE 62-continued

| 80 | Ex. 10 | Ex. 24 | 450 | 500 | 3/8 | pH 7.5 | 15 | 0 | 8 | 10 | 12 | 14 | 16 | 18 |
| --- | --- | --- | --- | --- | --- | --- | --- | --- | --- | --- | --- | --- | --- | --- |
| | | | | | | | | 0 | 0 | 0 | 0 | 0 | 0 | 45 |

| 81 | Ex. 10 | Ex. 24 | 450 | 500 | 3/8 | pH 7.5 | 30 | 0 | 8 | 10 | 12 | 14 | 16 | 18 |
| --- | --- | --- | --- | --- | --- | --- | --- | --- | --- | --- | --- | --- | --- | --- |
| | | | | | | | | 0 | 0 | 12 | 41 | 41 | 41 | 100 |

| 82 | Ex. 10 | Ex. 24 | 450 | 500 | 3/8 | Peanut Oil pH 1.5 | 15 | 0 | 2 | 4 | 6 | 8 | 10 | 12 |
| --- | --- | --- | --- | --- | --- | --- | --- | --- | --- | --- | --- | --- | --- | --- |
| | | | | | | | | 0 | 0 | 0 | 0 | 0 | 0 | 0 |

| 83 | Ex. 10 | Ex. 24 | 450 | 500 | 3/8 | Peanut Oil pH 7.5 | 15 | 0 | 2 | 4 | 6 | 8 | 10 | 12 |
| --- | --- | --- | --- | --- | --- | --- | --- | --- | --- | --- | --- | --- | --- | --- |
| | | | | | | | | 0 | 0 | 0 | 100 | 100 | 100 | 100 |

| 84 | Ex. 1 | Ex. 24 | 250 | 300 | 5/16 | DI Water | 15 | 0 | 2 | 4 | 5 | 6 | 7 | 8 |
| --- | --- | --- | --- | --- | --- | --- | --- | --- | --- | --- | --- | --- | --- | --- |
| | | | | | | | | 0 | 0 | 86 | 100 | 100 | 100 | 100 |

| 85 | Ex. 10 | Ex. 24 | 250 | 300 | 5/16 | DI Water | 15 | 0 | 2 | 3 | 4 | 5 | 6 | 7 |
| --- | --- | --- | --- | --- | --- | --- | --- | --- | --- | --- | --- | --- | --- | --- |
| | | | | | | | | 0 | 0 | 0 | 18 | 97 | 100 | 100 |

| 86 | Ex. 10 | Ex. 24 | 400 | 450 | 5/16 | DI Water | 5 | 0 | 8 | 9 | 10 | 11 | 12 | 14 |
| --- | --- | --- | --- | --- | --- | --- | --- | --- | --- | --- | --- | --- | --- | --- |
| | | | | | | | | 0 | 0 | 16 | 37 | 99 | 100 | 100 |

| 87 | Ex. 10 | Ex. 24 | 400 | 450 | 5/16 | DI Water | 15 | 0 | 2 | 3 | 4 | 5 | 6 | 7 |
| --- | --- | --- | --- | --- | --- | --- | --- | --- | --- | --- | --- | --- | --- | --- |
| | | | | | | | | 0 | 0 | 0 | 0 | 98 | 100 | 100 |

| 88 | Ex. 10 | Ex. 24 | 450 | 500 | 3/8 | DI Water | 15 | 0 | 4 | 4.5 | 5 | 5.5 | 6 | 68 |
| --- | --- | --- | --- | --- | --- | --- | --- | --- | --- | --- | --- | --- | --- | --- |
| | | | | | | | | 0 | 0 | 0 | 0 | 51 | 83 | 100 |

| 89 | Ex. 10 | Ex. 24 | 550 | 600 | 7/16 | DI Water | 10 | 0 | 6 | 7 | 8 | 9 | 10 | 11 |
| --- | --- | --- | --- | --- | --- | --- | --- | --- | --- | --- | --- | --- | --- | --- |
| | | | | | | | | 0 | 0 | 0 | 89 | 100 | 100 | 100 |

| 90 | Ex. 10 | Ex. 24 | 550 | 600 | 7/16 | DI Water | 15 | 0 | 5 | 5.5 | 6 | 6.5 | 7 | 7.5 |
| --- | --- | --- | --- | --- | --- | --- | --- | --- | --- | --- | --- | --- | --- | --- |
| | | | | | | | | 0 | 0 | 11.5 | 87.1 | 100 | 100 | 100 |

| 91 | Ex. 10 | Ex. 24 | 450 | 500 | 3/8 | DI Water | 5 | 0 | 10 | 10.5 | 11 | 11.5 | 12 | 12.5 |
| --- | --- | --- | --- | --- | --- | --- | --- | --- | --- | --- | --- | --- | --- | --- |
| | | | | | | | | 0 | 0 | 0 | 4.3 | 49.1 | 97.1 | 100 |

| 92 | Ex. 10 | Ex. 24 | 450 | 500 | 3/8 | DI Water | 10 | 0 | 7 | 8 | 9 | 10 | 11 | 12 |
| --- | --- | --- | --- | --- | --- | --- | --- | --- | --- | --- | --- | --- | --- | --- |
| | | | | | | | | 0 | 0 | 45.4 | 66.7 | 83.3 | 100 | 100 |

| 93 | Ex. 10 | Ex. 24 | 450 | 500 | 3/8 | DI Water | 15 | 0 | 5 | 5.5 | 5.75 | 6 | 6.25 | 6.75 |
| --- | --- | --- | --- | --- | --- | --- | --- | --- | --- | --- | --- | --- | --- | --- |
| | | | | | | | | 0 | 0 | 33.3 | 33.3 | 66.7 | 83.3 | 100 |

| 94 | Ex. 10 | Ex. 24 | 450 | 500 | 3/8 | DI Water | 20 | 0 | 3 | 3.5 | 4 | 4.5 | 5 | 5.5 |
| --- | --- | --- | --- | --- | --- | --- | --- | --- | --- | --- | --- | --- | --- | --- |
| | | | | | | | | 0 | 0 | 0 | 39 | 99.3 | 100 | 100 |

| 95 | Ex. 10 | Ex. 22 | 250 | 300 | 5/16 | DI Water | 15 | 0 | 2 | 3 | 4 | 5 | 6 | 7 |
| --- | --- | --- | --- | --- | --- | --- | --- | --- | --- | --- | --- | --- | --- | --- |
| | | | | | | | | 0 | 0 | 0 | 67 | 100 | 100 | 100 |

TABLE 62-continued

| | | | | | | | | 0 | 2 | 4 | 6 | 8 | 10 | 16 |
|---|---|---|---|---|---|---|---|---|---|---|---|---|---|---|
| 96 | Ex. 2 | Ex. 20 | 850 | 900 | 1/2 | DI Water | 15 | 0 | 37 | 48 | 48 | 48 | 48 | 98 |
| | | | | | | | | 0 | 2 | 4 | 6 | 8 | 10 | 16 |
| 97 | Ex. 3 | Ex. 20 | 250 | 300 | 3/8 | DI Water | 15 | 0 | 0.8 | 42 | 42 | 97 | 100 | 100 |
| | | | | | | | | 0 | 4 | 6 | 8 | 10 | 12 | 16 |
| 98 | Ex. 2 | Ex. 21 | 250 | 400 | 3/8 | DI Water | 15 | 0 | 0 | 0 | 0 | 0 | 100 | 100 |
| | | | | | | | | 0 | 4 | 6 | 8 | 10 | 12 | 16 |
| 99 | Ex. 2 | Ex. 21 | 350 | 400 | 3/8 | DI Water | 15 | 0 | 0 | 0 | 0 | 0 | 20 | 20 |
| | | | | | | | | 0 | 3 | 3 | 4 | 5 | 6 | 8 |
| 100 | Ex. 2 | Ex. 21 | 150 | 200 | 9/32 | DI Water | 15 | 0 | 17 | 17 | 23 | 36 | 41 | 100 |
| | | | | | | | | 0 | 2 | 3 | 4 | 5 | 6 | 8 |
| 101 | Ex. 2 | Ex. 19 | 150 | 200 | 9/32 | DI Water | 15 | 0 | 0 | 0 | 0 | 0 | 0 | 0 |
| | | | | | | | | 0 | 4 | 5 | 6 | 8 | 10 | 12 |
| 102 | Ex. 3 | Ex. 19 | 150 | 200 | 9/32 | DI Water | 15 | 0 | 55.6 | 55.6 | 66.7 | 66.7 | 87.7 | 100 |
| | | | | | | | | 0 | 4 | 6 | 8 | 10 | 12 | 16 |
| 103 | Ex. 3 | Ex. 19 | 250 | 300 | 3/8 | DI Water | 15 | 0 | 0 | 100 | 100 | 100 | 100 | 100 |
| | | | | | | | | 0 | 4 | 6 | 8 | 10 | 12 | 16 |
| 104 | Ex. 3 | Ex. 19 | 250 | 300 | 3/8 | DI Water | 15 | 0 | 0 | 0 | 18 | 52 | 100 | 100 |
| | | | | | | | | 0 | 4 | 6 | 8 | 10 | 12 | 16 |
| 105 | Ex. 2 | Ex. 19 | 150 | 200 | 9/32 | DI Water | 15 | 0 | 0 | 0 | 0 | 0 | 46 | 67 |
| | | | | | | | | 0 | 4 | 6 | 8 | 10 | 12 | 16 |
| 106 | Ex. 2 | Ex. 22 | 175 | 225 | 9/32 | DI Water | 15 | 0 | 0 | 0 | 0 | 0 | 25 | 100 |
| | | | | | | | | 0 | 4 | 6 | 8 | 10 | 12 | 16 |
| 107 | Ex. 2 | Ex. 22 | 170 | 220 | 9/32 | DI Water | 15 | 0 | 0 | 0 | 0 | 0 | 17 | 100 |
| | | | | | | | | 0 | 14 | 15 | 16 | 17 | 18 | 19 |
| 108 | Ex. 2 | Ex. 23 | 355 | 525 | 5/16 | DI Water | 15 | 0 | 7.5 | 55 | 100 | 100 | 100 | 100 |
| | | | | | | | | 0 | 14 | 14 | 15 | 15 | 16 | 16 |
| 109 | Ex. 2 | Ex. 23 | 390 | 560 | 5/16 | DI Water | 15 | 0 | 35 | 56 | 76 | 80 | 93 | 100 |
| | | | | | | | | 0 | 12 | 13 | 14 | 15 | 16 | 17 |
| 110 | Ex. 2 | Ex. 23 | 330 | 500 | 3/8 | DI Water | 15 | 0 | 11 | 33 | 52 | 75 | 90 | 100 |
| | | | | | | | | 0 | 8 | 10 | 12 | 14 | 16 | 18 |
| 111 | Ex. 2 | Ex. 24 | 250 | 300 | 7/16 | DI Water | 15 | 0 | 0 | 0 | 0 | 0 | 0 | 33 |

TABLE 62-continued

| | | | | | | | | | | | | | | |
|---|---|---|---|---|---|---|---|---|---|---|---|---|---|---|
| 112 | Ex. 2 | Ex. 24 | 250 | 300 | 5/16 | DI Water | 15 | 0 | 8 | 10 | 12 | 14 | 16 | 18 |
| | | | | | | | | 0 | 3 | 6.6 | 11 | 16 | 34 | 87 |
| 113 | Ex. 2 | Ex. 31 | 250 | 300 | 5/16 | DI Water | 15 | 0 | 8 | 10 | 12 | 14 | 16 | 20 |
| | | | | | | | | 0 | 1.1 | 5.9 | 44 | 92 | 100 | 100 |
| 114 | Ex. 3 | Ex. 21 | 350 | 400 | 3/8 | DI Water | 15 | 0 | 4 | 6 | 8 | 10 | 12 | 16 |
| | | | | | | | | 0 | 0 | 0 | 0 | 6.8 | 34 | 100 |
| 115 | Ex. 3 | Ex. 21 | 250 | 300 | 3/8 | DI Water | 15 | 0 | 4 | 6 | 8 | 10 | 12 | 16 |
| | | | | | | | | 0 | 0 | 0 | 0 | 36 | 100 | 100 |
| 116 | Ex. 2 | Ex. 19 | 150 | 200 | 9/32 | DI Water | 15 | 0 | 2 | 3 | 4 | 5 | 6 | 8 |
| | | | | | | | | 0 | 0 | 0 | 0 | 0 | 0 | 0 |
| 117 | Ex. 2 | Ex. 19 | 150 | 200 | 9/32 | DI Water | 15 | 0 | 4 | 6 | 8 | 10 | 12 | 16 |
| | | | | | | | | 0 | 0 | 0 | 0 | 20 | 67.7 | 100 |
| 118 | Ex. 3 | Ex. 19 | 250 | 300 | 3/8 | DI Water | 15 | 0 | 4 | 6 | 8 | 10 | 12 | 16 |
| | | | | | | | | 0 | 100 | 100 | 100 | 100 | 100 | 100 |
| 119 | Ex. 2 | Ex. 19 | 250 | 300 | 3/8 | DI Water | 15 | 0 | 4 | 6 | 8 | 10 | 12 | 16 |
| | | | | | | | | 0 | 0 | 0 | 18 | 52 | 100 | 100 |
| 120 | Ex. 3 | Ex. 19 | 170 | 220 | 9/32 | DI Water | 15 | 0 | 4 | 6 | 8 | 10 | 12 | 16 |
| | | | | | | | | 0 | 0 | 30 | 65 | 95 | 95 | 100 |
| 121 | Ex. 3 | Ex. 19 | 170 | 220 | 9/32 | pH Change | 15 | 0 | 2 | 4 | 6 | 8 | 10 | 12 |
| | | | | | | | | 0 | 0 | 0 | 0 | 0 | 0 | 5 |
| 122 | Ex. 3 | Ex. 24 | 450 | 500 | 5/16 | DI Water | 15 | 0 | 6 | 8 | 10 | 12 | 14 | 18 |
| | | | | | | | | 0 | 0 | 33 | 33 | 100 | 100 | 100 |
| 123 | Ex. 3 | Ex. 24 | 250 | 300 | 5/16 | DI Water | 15 | 0 | 2 | 4 | 6 | 8 | 10 | 14 |
| | | | | | | | | 0 | 0 | 0 | 5.6 | 25 | 68 | 91 |
| 124 | Ex. 9 | Ex. 24 | 250 | 300 | 5/16 | DI Water | 15 | 0 | 2 | 3 | 4 | 5 | 6 | 7 |
| | | | | | | | | 0 | 0 | 0 | 32 | 100 | 100 | 100 |
| 125 | Ex. 9 | Ex. 24 | 450 | 500 | 3/8 | DI Water | 15 | 0 | 2 | 3 | 4 | 5 | 6 | 7 |
| | | | | | | | | 0 | 0 | 0 | 0 | 0.7 | 86 | 100 |
| 126 | Ex. 4 | Ex. 24 | 250 | 300 | 5/16 | DI Water | 15 | 0 | 2 | 3 | 4 | 5 | 6 | 7 |
| | | | | | | | | 0 | 0 | 22 | 100 | 100 | 100 | 100 |
| 127 | Ex. 4 | Ex. 24 | 250 | 300 | 5/16 | DI Water | 15 | 0 | 2 | 3 | 4 | 5 | 6 | 7 |
| | | | | | | | | 0 | 11 | 73 | 100 | 100 | 100 | 100 |

TABLE 62-continued

| # | | | | | | | | | | | | | | |
|---|---|---|---|---|---|---|---|---|---|---|---|---|---|---|
| 128 | Ex. 4 | Ex. 22 | 250 | 300 | 5/16 | DI Water | 15 | 0 | 3 | 3.5 | 4 | 4.5 | 5 | 5.5 |
| | | | | | | | | 0 | 0 | 52 | 100 | 100 | 100 | 100 |
| 129 | Ex. 4 | Ex. 22 | 250 | 300 | 5/16 | DI Water | 15 | 0 | 3.5 | 3.7 | 3.8 | 4 | 4.2 | 4.3 |
| | | | | | | | | 0 | 0 | 23 | 36 | 45 | 64 | 97 |
| 130 | Ex. 4 | Ex. 22 | 250 | 300 | 5/16 | DI Water | 15 | 0 | 3 | 3.5 | 4 | 4.5 | 5 | 5.5 |
| | | | | | | | | 0 | 3.8 | 74 | 100 | 100 | 100 | 100 |
| 131 | Ex. 4 | Ex. 22 | 250 | 300 | 5/16 | DI Water | 15 | 0 | 2 | 3 | 4 | 5 | 6 | 7 |
| | | | | | | | | 0 | 0 | 8.1 | 55 | 100 | 100 | 100 |
| 132 | Ex. 4 | Ex. 22 | 250 | 300 | 5/16 | pH Change No Ion | 15 | 0 | 1 | 3 | 5 | 7 | 9 | 11 |
| | | | | | | | | 0 | 0 | 0 | 0 | 7.7 | 18 | 100 |
| 133 | Ex. 4 | Ex. 22 | 250 | 300 | 5/16 | DI Water | 15 | 0 | 1 | 2 | 3 | 4 | 5 | 6 |
| | | | | | | | | 0 | 0 | 0 | 0 | 32 | 100 | 100 |
| 134 | Ex. 4 | Ex. 22 | 250 | 300 | 5/16 | pH Change | 15 | 0 | 1 | 3 | 6 | 8 | 11 | 14 |
| | | | | | | | | 0 | 0 | 0 | 0 | 0 | 0 | 0 |
| 135 | Ex. 4 | Ex. 22 | 250 | 300 | 5/16 | pH Change | 15 | 0 | 1 | 3 | 5 | 8 | 15 | 20 |
| | | | | | | | | 0 | 0 | 0 | 0 | 11 | 70 | 100 |
| 136 | Ex. 4 | Ex. 22 | 250 | 300 | 5/16 | pH Change | 30 | 0 | 1 | 3 | 5 | 10 | 15 | 10 |
| | | | | | | | | 0 | 0 | 0 | 17 | 100 | 100 | 100 |
| 137 | Ex. 8 | Ex. 22 | 170 | 220 | 9/32 | DI Water | 15 | 0 | 2 | 4 | 6 | 8 | 10 | 12 |
| | | | | | | | | 0 | 92 | 100 | 100 | 100 | 100 | 100 |
| 138 | Ex. 8 | Ex. 24 | 170 | 220 | 9/32 | DI Water | 15 | 0 | 1 | 2 | 3 | 4 | 5 | 6 |
| | | | | | | | | 0 | 28 | 100 | 100 | 100 | 100 | 100 |
| 139 | Ex. 8 | Ex. 24 | 250 | 300 | 5/16 | DI Water | 15 | 0 | 1 | 2 | 3 | 4 | 5 | 6 |
| | | | | | | | | 0 | 0 | 50 | 100 | 100 | 100 | 100 |
| 140 | Ex. 7 | Ex. 24 | 250 | 300 | 5/16 | DI Water | 15 | 0 | 1 | 2 | 3 | 4 | 5 | 6 |
| | | | | | | | | 0 | 0 | 13.1 | 71.3 | 94.1 | 96 | 96 |
| 141 | Ex. 7 | Ex. 24 | 350 | 400 | 3/8 | DI Water | 15 | 0 | 1 | 2 | 3 | 4 | 5 | 6 |
| | | | | | | | | 0 | 0 | 0 | 25 | 100 | 100 | 100 |
| 142 | Ex. 6 | Ex. 24 | 250 | 300 | 5/16 | DI Water | 15 | 0 | 2 | 4 | 6 | 8 | 10 | 12 |
| | | | | | | | | 0 | 0 | 100 | 100 | 100 | 100 | 100 |
| 143 | Ex. 5 | Ex. 24 | 250 | 300 | 5/16 | DI Water | 15 | 0 | 1 | 2 | 3 | 4 | 5 | 6 |
| | | | | | | | | 0 | 0 | 0 | 0 | 0 | 100 | 100 |

TABLE 62-continued

| # | Material 1 | Material 2 | Col A | Col B | Col C | Liquid | Col D | Time points → Values |
|---|---|---|---|---|---|---|---|---|
| 144 | Ex. 5 | Ex. 24 | 400 | 450 | 3/8 | DI Water | 15 | 0, 3, 4, 5, 6, 7, 8 → 0, 0, 0, 0, 75, 91, 100 |
| 145 | Ex. 6 | Ex. 24 | 400 | 450 | 3/8 | DI Water | 15 | 0, 1, 2, 3, 4, 5, 6 → 0, 0, 0, 17, 83, 100, 100 |
| 146 | 50% LBG | Ex. 24 | 400 | 450 | 3/8 | DI Water | 15 | 0, 8, 10, 12, 14, 16, 20 → 0, 2.8, 6, 9.5, 57, 87.3, 100 |
| 147 | 30% LBG | Ex. 24 | 400 | 450 | 3/8 | DI Water | 15 | 0, 8, 10, 12, 14, 16, 20 → 0, 5.7, 12, 19, 98, 100, 100 |
| 148 | 30% LBG | Ex. 24 | 450 | 500 |  | DI Water | 15 | 0, 10, 14, 16, 18, 20, 22 → 0, 4.1, 13, 40, 69, 83, 83 |
| 149 | 50% Ex. 4 and 50% Ex. 2 | Ex. 22 | 250 | 300 | 5/16 | DI Water | 15 | 0, 2, 3, 4, 5, 6, 7 → 0, 0, 0, 0, 0, 0, 0 |
| 150 | Xanthan Gum | Ex. 22 | 170 | 220 | 9/32 | DI Water | 15 | 0, 3, 3.5, 4, 4.5, 5, 6 → 0, 0, 0, 55.9, 100, 100, 100 |
| 151 | Xanthan Gum | Ex. 22 | 170 | 220 | 9/32 | DI Water | 15 | 0, 1, 2, 3, 4, 5, 6 → 0, 0, 0, 0, 67, 100, 100 |
| 152 | Xanthan Gum | Ex. 24 | 250 | 300 | 5/16 | DI Water | 15 | 0, 3, 4, 5, 6, 7, 8 → 0, 0, 0, 38, 100, 100, 100 |
| 153 | 30% Xanthan Gum | Ex. 24 | 250 | 300 | 5/16 | DI Water | 15 | 0, 2, 3, 4, 5, 6, 8 → 0, 0, 80, 100, 100, 100, 100 |
| 154 | 50% Xanthan Gum | Ex. 24 | 250 | 300 | 5/16 | DI Water | 15 | 0, 2, 4, 6, 8, 10, 12 → 0, 0, 0, 100, 100, 100, 100 |
| 155 | 50% Xanthan Gum | Ex. 24 | 250 | 300 | 5/16 | DI Water | 15 | 0, 4, 5, 5.5, 6, 6.5, 7 → 0, 2.6, 99, 100, 100, 100, 100 |
| 156 | Xanthan Gum | Ex. 24 | 250 | 300 | 5/16 | pH 1.5 | 15 | 0, 6, 8, 10, 12, 14, 16 → 0, 0, 0, 0, 0, 0, 5.2 |
| 157 | Ex. 11 | Ex. 36 | 250 | 300 | 5/16 | pH Change | 15 | 0, 1, 3, 5, 8, 11, 14 → 0, 0, 5.8, 6.7, 11, 16, 68 |
| 158 | Ex. 12 | Ex. 36 | 250 | 300 | 5/16 | pH Change | 15 | 0, 1, 3, 5, 8, 11, 14 → 0, 0.8, 1, 3.4, 19, 38, 93 |
| 159 | Ex. 14 | Ex. 36 | 250 | 300 | 5/16 | pH Change | 15 | 0, 1, 3, 5, 8, 11, 14 → 0, 0, 0.8, 5.6, 97, 100, 100 |

TABLE 62-continued

| # | A | B | C | D | E | Condition | F | Time/Values |
|---|---|---|---|---|---|---|---|---|
| 160 | Ex. 16 | Ex. 36 | 250 | 300 | 5/16 | pH Change | 15 | 0: 0, 1: 3.2, 3: 99, 5: 100, 8: 100, 11: 100, 14: 100 |
| 161 | Ex. 16 | Ex. 36 | 250 | 300 | 5/16 | DI Water | 15 | 0: 0, 0.5: 0, 1: 98, 1.5: 100, 2: 100, 2.5: 100, 3: 100 |
| 162 | Ex. 14 | Ex. 36 | 250 | 300 | 5/16 | DI Water | 15 | 0: 0, 0.5: 0, 1: 31, 1.5: 99, 2: 100, 2.5: 100, 3: 100 |
| 163 | Ex. 15 | Ex. 36 | 250 | 300 | 5/16 | DI Water | 15 | 0: 0, 1: 1, 1.5: 33, 2: 99, 2.5: 100, 3: 100, 3.5: 100 |
| 164 | Ex. 11 | Ex. 36 | 250 | 300 | 5/16 | DI Water | 15 | 0: 0, 1: 0, 1.5: 0, 2: 30, 2.5: 99, 3: 100, 3.5: 100 |
| 165 | Ex. 16 | Ex. 36 | 250 | 300 | 5/16 | pH 7.5 [0.1 M] | 15 | 0: 0, 1: 0, 3: 98, 5: 100, 8: 100, 11: 100, 14: 100 |
| 166 | Ex. 14 | Ex. 36 | 250 | 300 | 5/16 | pH 7.5 [0.1 M] | 15 | 0: 0, 1: 0, 3: 0, 5: 42, 8: 100, 11: 100, 14: 100 |
| 167 | Ex. 12 | Ex. 36 | 250 | 300 | 5/16 | pH 7.5 [0.1 M] | 15 | 0: 0, 1: 0, 3: 0, 5: 0, 8: 6.4, 11: 100, 14: 100 |
| 168 | Ex. 11 | Ex. 36 | 250 | 300 | 5/16 | pH 7.5 [0.1 M] | 15 | 0: 0, 1: 0, 3: 0, 5: 0, 8: 4.3, 11: 11, 14: 97 |
| 169 | Ex. 16 | Ex. 36 | 250 | 300 | 5/16 | pH 1.5 [0.1 M] | 15 | 0: 0, 1: 0, 3: 98, 5: 100, 8: 100, 11: 100, 14: 100 |
| 170 | Ex. 14 | Ex. 36 | 250 | 300 | 5/16 | pH 1.5 [0.1 M] | 15 | 0: 0, 1: 0, 3: 0, 5: 33, 8: 99, 11: 100, 14: 100 |
| 171 | Ex. 12 | Ex. 36 | 250 | 300 | 5/16 | pH 1.5 [0.1 M] | 15 | 0: 0, 1: 1, 3: 0, 5: 2.2, 8: 9.6, 11: 61, 14: 100 |
| 172 | Ex. 11 | Ex. 36 | 250 | 300 | 5/16 | pH 1.5 [0.1 M] | 15 | 0: 0, 1: 0, 3: 0, 5: 0, 8: 6, 11: 13, 14: 73 |
| 173 | Ex. 15 | Ex. 36 | 250 | 300 | 5/16 | DI Water | 15 | 0: 0, 0.5: 0, 1: 65, 1.5: 99, 2: 100, 2.5: 100, 3: 100 |
| 174 | Ex. 13 | Ex. 36 | 250 | 300 | 5/16 | DI Water | 15 | 0: 0, 0.5: 0, 1: 0, 1.5: 65, 2: 100, 2.5: 100, 3: 10 |
| 175 | Ex. 15 | Ex. 36 | 250 | 300 | 5/16 | pH Change | 15 | 0: 0, 1: 0, 3: 0.7, 5: 91, 8: 100, 11: 100, 14: 100 |

TABLE 62-continued

| | | | | | | | | 0 | 1 | 3 | 5 | 8 | 11 | 14 |
|---|---|---|---|---|---|---|---|---|---|---|---|---|---|---|
| 176 | Ex. 13 | Ex. 36 | 250 | 300 | 5/16 | pH Change | 15 | 0 | 0 | 0 | 3.3 | 11 | 70 | 100 |
| 177 | Ex. 15 | Ex. 36 | 250 | 300 | 5/16 | pH 7.5 [0.1 M] | 15 | 0 | | | | | | |
| 178 | Ex. 13 | Ex. 36 | 250 | 300 | 5/16 | pH 7.5 [0.1 M] | 15 | 0 | | | | | | |
| 179 | Ex. 15 | Ex. 36 | 250 | 300 | 5/16 | pH 1.5 [0.1 M] | 15 | 0 | | | | | | |
| 180 | Ex. 13 | Ex. 36 | 250 | 300 | 5/16 | pH 1.5 [0.1 M] | 15 | 0 | | | | | | |

Comments:
1. Test 9 was average merged data.
2. Test 14 was average merged data.
3. Test 16 was average merged data.
4. Test 17 utilized 5% PVP added to the coating as an additional excipient.
5. Test 18 utilized 10% PVP added to the coating as an additional excipient.
6. Test 19 utilized 5% MCC added to the coating as an additional excipient.
7. Test 20 utilized 5% MCC added to the coating as an additional excipient.
8. Test 21 utilized 10% PEG added to the coating as an additional excipient.
9. Test 22 utilized 5% PEG added to the coating as an additional excipient.
10. Test 23 utilized 10% MCC added to the coating as an additional excipient.
11. Test 24 utilized 20% MCC added to the coating as an additional excipient.
12. Test 25 utilized 5% PEG added to the coating as an additional excipient.
13. Test 26 utilized 5% PEG added to the coating as an additional excipient.
14. Test 27 utilized 10% PVP added to the coating as an additional excipient.
15. Test 28 utilized 10% PVP added to the coating as an additional excipient.
16. Test 29 utilized 10% PEG added to the coating as an additional excipient.
17. Test 30 utilized 5% PVP added to the coating as an additional excipient.
18. Test 31 utilized 15% PEG added to the coating as an additional excipient.
19. Test 32 utilized 5% Calcium Sulfate added to the coating as an additional excipient.
20. Test 33 utilized 10% Calcium Sulfate added to the coating as an additional excipient.
21. Test 34 utilized 10% Calcium Sulfate added to the coating as an additional excipient.
22. Test 35 utilized 30% Calcium Sulfate added to the coating as an additional excipient.
23. Test 36 utilized 5% Calcium Sulfate added to the coating as an additional excipient.
24. Test 37 utilized 10% Calcium Sulfate added to the coating as an additional excipient.
25. Test 38 utilized 30% Calcium Sulfate added to the coating as an additional excipient.
26. Test 39 utilized 30% Calcium Sulfate added to the coating as an additional excipient.
27. Test 40 utilized 15% PEG added to the coating as an additional excipient.
28. Test 41 utilized 305% Calcium Sulfate added to the coating as an additional excipient.
29. Test 54 was average merged data.
30. Test 90 was average merged data.
31. Test 96 was based on two tablets.
32. Test 97 was based on two tablets.
33. Test 98 was based on three tablets.
34. Test 99 was based on three tablets.
35. Test 100 was based on six tablets.
36. Test 101 was based on three tablets.
37. Test 102 was average merged data.
38. Test 103 was based on three tablets.
39. Test 104 was based on three tablets.
40. Test 105 was based on three tablets.
41. Test 106 was based on twelve tablets.
42. Test 107 was average merged data.
43. Test 108 was based on six tablets.
44. Test 109 was based on twelve tablets.
45. Test 110 was based on twelve tablets.
46. Test 111 was based on three tablets.
47. Test 112 was based on six tablets.
48. Test 113 was based on twelve tablets.
49. Test 117 was averaged merged data.
50. Test 120 was average merged data.
51. Test 140 was average merged data.
52. Test 146 was average merged data.
53. Test 150 was average merged data.

Example 70

An albuterol core composition was prepared having the formulation ingredients set forth in Table 63:

TABLE 63

| Component | Percent | amt. (mg) |
|---|---|---|
| 1. Albuterol | 19.2 | 9.6 |
| 2. Prosolv SMCC ™ 50 | 26.8 | 13.4 |
| 3. Prosolve SMCC ™ 90 | 41 | 20.63 |
| 4. Silicone dioxide | 0.5 | 0.25 |
| 5. Explotab | 6 | 3 |
| 6. Sodium carboxymethylcellulose | 2 | 1 |
| 7. Talc | 4 | 2 |
| 8. Pruv | 0.25 | 0.13 |
| Total | 100 | 50 |
| Core size and shape | 5/16 Round SC | |

Process:

The same process for Example 23 is used to prepare the core in Example 70.

Example 71

An albuterol core composition was prepared having the formulation ingredients set forth in Table 64:

TABLE 64

| Component | Percent | amt. (mg) |
|---|---|---|
| 1. Albuterol | 10 | 9.60 |
| 2. Prosolv SMCC ™ 50 | 26.8 | 25.73 |
| 3. Prosolve SMCC ™ 90 | 50 | 48.43 |
| 4. Silicone dioxide | 0.5 | 0.48 |
| 5. Explotab | 6 | 5.76 |
| 6. Sodium carboxymethylcellulose | 2 | 1.92 |
| 7. Talc | 4 | 3.84 |
| 8. Pruv | 0.25 | 0.24 |
| Total | 100 | 96 |
| Core size and shape | 1/4" Round SC | |

Process:

The same process for Example 23 is used to prepare the core in Example 71.

Example 72

An albuterol core composition was prepared having the formulation ingredients set forth in Table 65:

TABLE 65

| Component | Percent | amt. (mg) |
|---|---|---|
| 1. Albuterol | 4.8 | 2.4 |
| 2. Prosolv SMCC ™ 50 | 37.2 | 18.6 |
| 3. Prosolve SMCC ™ 90 | 48 | 23.88 |
| 4. Explotab | 6 | 3.0 |
| 5. Sodium carboxymethylcellulose | 2 | 1.0 |
| 6. Talc | 2 | 1.0 |
| 7. Pruv | 0.25 | 0.13 |
| Total | 100 | 50 |
| Core size and shape | 3/16 Round SC | |

Process:

The same process for Example 23 is used to prepare the core in Example 72.

Example 73

An albuterol core composition was prepared having the formulation ingredients set forth in Table 66:

TABLE 66

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |
| 7. Talc | 4 | 4.40 |
| 8. Pruv | 0.25 | 0.25 |
| Total | 100 | 110 |
| Core size and shape | 1/4 Round SC | |

Process:

The same process for Example 23 is used to prepare the core in Example 73.

Example 74

An albuterol core composition was prepared having the formulation ingredients set forth in Table 67:

TABLE 67

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |
| 7. Talc | 4 | 4.40 |
| 8. Pruv | 0.25 | 0.25 |
| No coating | | |
| Total | 100 | 110 |
| Core size and shape | 1/4 round SC | |

Process:

The same process for Example 23 is used to prepare the core in Example 74.

Example 75

An albuterol core composition was prepared having the formulation ingredients set forth in Table 68:

TABLE 68

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |

TABLE 68-continued

| Component | Percent | Amt. (mg) |
|---|---|---|
| 6. Sodium carboxymethylcellulose | 2 | 2.20 |
| 7. Talc | 4 | 4.40 |
| 8. Pruv | 0.25 | 0.25 |
| Total | 100 | 110 |
| Film coating 3% (3.3 mg) Opadry AMB | | |
| Core size and shape | ¼ round SC | |

Process:

The same process for Example 23 is used to prepare the core, along with a film coating where applicable (see Table 68) in Example 75.

Example 76

An albuterol core composition was prepared having the formulation ingredients set forth in Table 69:

TABLE 69

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |
| 7. Talc | 4 | 4.40 |
| 8. Pruv | 0.25 | 0.25 |
| Total | 100 | 110 |
| Film Coating 6% (6.6 mg) opadry AMB | | |
| Core size and shape | ¼ round SC | |

Process:

The same process for Example 23 is used to prepare the core, along with a film coating where applicable (see Table 69) in Example 76.

Example 77

An albuterol core composition was prepared having the formulation ingredients set forth in Table 70:

TABLE 70

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |
| 7. Talc | 4 | 4.40 |
| 8. Pruv | 0.25 | 0.25 |
| Total | 100 | 110 |
| Film coating 3% (3.3 mg) opadry II | | |
| Core size and shape | ¼ round SC | |

Process:

The same process for Example 23 is used to prepare the core, along with a film coating where applicable (see Table 70) in Example 77.

Example 78

An albuterol core composition was prepared having the formulation ingredients set forth in Table 71:

TABLE 71

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |
| 7. Talc | 4 | 4.40 |
| 8. Pruv | 0.25 | 0.25 |
| Total | 100 | 110 |
| Film coating 6% (6.6 mg) Opadry II | | |
| Core size and shape | ¼ round SC | |

Process:

The same process for Example 23 is used to prepare the core, along with a film coating where applicable (see Table 71) in Example 78.

Example 79

An albuterol core composition was prepared having the formulation ingredients set forth in Table 72:

TABLE 72

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |
| 7. Talc | 4 | 4.40 |
| 8. Pruv | 0.25 | 0.25 |
| Total | 100 | 110 |
| Film coating 3% (3.3 mg) Opadry II | | |
| Core size and shape | ¼ round SC | |

Process:

The same process for Example 23 is used to prepare the core, along with a film coating where applicable (see Table 72) in Example 79.

Example 80

An albuterol core composition was prepared having the formulation ingredients set forth in Table 73:

TABLE 73

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |

TABLE 73-continued

| Component | Percent | Amt. (mg) |
|---|---|---|
| 7. Talc | 4 | 4.40 |
| 8. Pruv | 0.25 | 0.25 |
| Total | 100 | 110 |
| Film coating 6% (6.6 mg) Opadry II | | |
| Core size and shape | | ¼ round SC |

Process:

The same process for Example 23 is used to prepare the core, along with a film coating where applicable (see Table 73) in Example 80.

Example 81

An albuterol core composition was prepared having the formulation ingredients set forth in Table 74:

TABLE 74

| Component | Percent | Amt. (mg) |
|---|---|---|
| 1. Albuterol | 8.7 | 9.6 |
| 2. Prosolv SMCC ™ 50 | 26.8 | 29.48 |
| 3. Prosolve SMCC ™ 90 | 52 | 56.89 |
| 4. Silicon Dioxide | 0.5 | 0.55 |
| 5. Explotab | 6 | 6.60 |
| 6. Sodium carboxymethylcellulose | 2 | 2.20 |

TABLE 74-continued

| Component | Percent | Amt. (mg) |
|---|---|---|
| 7. Talc | 4 | 4.40 |
| 8. Pruv | 0.25 | 0.25 |
| Total | 100 | 110 |
| Film coating 0.5% (0.55 mg) Magnesium stearate | | |
| Core size and shape | | ¼ round SC |

Process:

The same process for Example 23 is used to prepare the core, along with a film coating where applicable (see Table 74) in Example 81.

Example 82

In Example 82, other formulations were prepared and tested using USP apparatus type 3, with 250 ml of the dissolution media and dips per minute as indicated in the Table 75.

The particular dissolution media are defined as follows:

| | |
|---|---|
| DI water: | USP purified water; |
| pH change NI (or no ion): | pH change method as described in Example 63, without the use of ions to change adjust the pH; |
| pH change or change (0.1M): | pH change method as described in Example 63 with the use of salts to give an ionic strength of 0.1 molar. |

TABLE 75

| Test | Coating Example | Core Example | Coating Amount | Tablet Weight (mg) | Coating Size | Dissolution Media | Dissol dpm | Dissolution Time (hrs) (shaded) vs. % Dissolved | | | | | | |
|---|---|---|---|---|---|---|---|---|---|---|---|---|---|---|
| | | | | | | | | 0 | 4 | 5 | 5 | 6 | 6 | 7 |
| 1 | Ex. 10 | Ex. 72 | 450 | 500 | 3/8 | DI Water | 15 | 0 | 0 | 0 | 13 | 72 | 98 | 100 |
| | | | | | | | | 0 | 4 | 5 | 5 | 6 | 6 | 7 |
| 2 | Ex. 10 | Ex. 72 | 450 | 500 | 3/8 | DI Water | 15 | 0 | 0 | 0 | 0 | 77 | 100 | 100 |
| | | | | | | | | 0 | 4 | 5 | 5 | 6 | 6 | 7 |
| 3 | Ex. 10 | Ex. 70 | 450 | 500 | 3/8 | DI Water | 15 | 0 | 0 | 2 | 8 | 48 | 79 | 100 |
| | | | | | | | | 0 | 3 | 4 | 5 | 5 | 6 | 6 |
| 4 | Ex. 10 | Ex. 70 | 250 | 300 | 5/16 | DI Water | 15 | 0 | 1 | 20 | 29 | 40 | 51 | 100 |
| | | | | | | | | 0 | 2 | 3 | 4 | 5 | 6 | 7 |
| 5 | Ex. 10 | Ex. 70 | 400 | 450 | 3/8 | DI Water | 15 | 0 | 0 | 0 | 0 | 40 | 98 | 100 |
| | | | | | | | | 0 | 8 | 10 | 12 | 14 | 16 | 18 |
| 6 | Ex. 2 | Ex. 70 | 250 | 300 | 5/16 | DI Water | 15 | 0 | 40 | 68 | 84 | 96 | 100 | 100 |
| | | | | | | | | 0 | 4 | 6 | 8 | 10 | 12 | 14 |
| 7 | Ex. 3 | Ex. 70 | 250 | 300 | 5/16 | DI Water | 15 | 0 | 11 | 50 | 88 | 98 | 100 | 100 |

TABLE 75-continued

| # | | | | | | | | t=0 | | | | | | |
|---|---|---|---|---|---|---|---|---|---|---|---|---|---|---|
| | | | | | | | | 0 | 4 | 6 | 8 | 10 | 12 | 16 |
| 8 | Ex. 3 | Ex. 71 | 350 | 460 | 3/8 | DI Water | 15 | 0 | 8 | 28 | 57 | 89 | 100 | 100 |
| | | | | | | | | 0 | 1 | 2 | 3 | 4 | 5 | 6 |
| 9 | Ex. 4 | Ex. 73 | 250 | 300 | 5/16 | DI Water | 15 | 0 | 0 | 0 | 0 | 86 | 100 | 100 |
| | | | | | | | | 0 | 1 | 2 | 3 | 4 | 5 | 6 |
| 10 | Ex. 4 | Ex. 70 | 250 | 300 | 5/16 | DI Water | 15 | 0 | 0 | 0 | 13 | 31 | 79 | 100 |
| | | | | | | | | 0 | 2 | 3 | 4 | 5 | 6 | 7 |
| 11 | Ex. 4 | Ex. 70 | 250 | 300 | 5/16 | DI Water | 15 | 0 | 0 | 5 | 71 | 84 | 100 | 100 |
| | | | | | | | | 0 | 2 | 3 | 4 | 4 | 5 | 5 |
| 12 | Ex. 1 | Ex. 70 | 250 | 300 | 5/16 | DI Water | 15 | 0 | 0 | 8 | 30 | 75 | 99 | 100 |
| | | | | | | | | 0 | 2 | 3 | 4 | 5 | 6 | 7 |
| 13 | Ex. 1 | Ex. 71 | 350 | 460 | 3/8 | DI Water | 15 | 0 | 14 | 57 | 99 | 100 | 100 | 100 |
| | | | | | | | | 0 | 2 | 3 | 4 | 5 | 6 | 7 |
| 14 | Ex. 1 | Ex. 71 | 350 | 460 | 3/8 | DI Water | 15 | 0 | 15 | 20 | 83 | 100 | 100 | 100 |
| | | | | | | | | 0 | 1 | 2 | 3 | 4 | 5 | 6 |
| 15 | Ex. 1 | Ex. 74 | 350 | 460 | 3/8 | DI Water | 15 | 0 | 0 | 0 | 27 | 91 | 100 | 100 |
| | | | | | | | | 0 | 1 | 2 | 3 | 4 | 5 | 6 |
| 16 | Ex. 1 | Ex. 75 | 350 | 460 | 3/8 | DI Water | 15 | 0 | 0 | 0 | 26 | 98 | 100 | 100 |
| | | | | | | | | 0 | 1 | 2 | 3 | 4 | 5 | 6 |
| 17 | Ex. 1 | Ex. 76 | 350 | 460 | 3/8 | DI Water | 15 | 0 | 0 | 0 | 3 | 68 | 100 | 100 |
| | | | | | | | | 0 | 1 | 2 | 3 | 4 | 5 | 6 |
| 18 | Ex. 1 | Ex. 77 | 350 | 460 | 3/8 | DI Water | 15 | 0 | 0 | 0 | 29 | 71 | 100 | 100 |
| | | | | | | | | 0 | 1 | 2 | 3 | 4 | 5 | 6 |
| 19 | Ex. 1 | Ex. 78 | 350 | 460 | 3/8 | DI Water | 15 | 0 | 0 | 0 | 26 | 98 | 100 | 100 |
| | | | | | | | | 0 | 1 | 2 | 3 | 4 | 5 | 6 |
| 20 | Ex. 1 | Ex. 79 | 350 | 460 | 3/8 | DI Water | 15 | 0 | 0 | 30 | 88 | 100 | 100 | 100 |
| | | | | | | | | 0 | 1 | 2 | 3 | 4 | 5 | 6 |
| 21 | Ex. 1 | Ex. 81 | 350 | 460 | 3/8 | DI Water | 15 | 0 | 0 | 0 | 62 | 99 | 100 | 100 |
| | | | | | | | | 0 | 1 | 2 | 3 | 4 | 5 | 6 |
| 22 | Ex. 1 | Ex. 71 | 350 | 460 | 3/8 | DI Water | 15 | 0 | 0 | 0 | 4 | 96 | 100 | 100 |
| | | | | | | | | 0 | 1 | 2 | 3 | 4 | 5 | 6 |
| 23 | Ex. 1 | Ex. 81 | 350 | 460 | 3/8 | DI Water | 15 | 0 | 0 | 0 | 32 | 70 | 100 | 100 |

TABLE 75-continued

| | | | | | | | | 0 | 1 | 2 | 3 | 4 | 5 | 6 |
|---|---|---|---|---|---|---|---|---|---|---|---|---|---|---|
| 24 | Ex. 1 | Ex. 74 | 400 | 510 | 3/8 | DI Water | 15 | 0 | 0 | 0 | 0 | 61 | 99 | 100 |
| 25 | Ex. 1 | Ex. 74 | 300 | 410 | 3/8 | DI Water | 15 | 0 | 0 | 0 | 45 | 77 | 100 | 100 |
| 26 | Ex. 1 | Ex. 74 | 350 | 460 | 3/8 | DI Water | 15 | 0 | 0 | 0 | 1 | 67 | 100 | 100 |
| 27 | Ex. 1 | Ex. 77 | 350 | 460 | 3/8 | DI Water | 15 | 0 | 0 | 0 | 18 | 46 | 99 | 100 |
| 28 | Ex. 1 | Ex. 81 | 350 | 460 | 3/8 | DI Water | 15 | 0 | 0 | 14 | 96 | 0 | 0 | 0 |
| 29 | Ex. 1 | Ex. 73 | 300 | 410 | * | DI Water | 15 | 0 | 0 | 37 | 98 | 100 | 100 | 100 |
| 30 | Ex. 1 | Ex. 73 | 300 | 410 | * | DI Water | 15 | 0 | 0 | 27 | 82 | 99 | 100 | 100 |
| 31 | Ex. 1 | Ex. 73 | 300 | 410 | * | DI Water | 15 | 0 | 0 | 24 | 99 | 100 | 100 | 100 |
| 32 | Ex. 1 | Ex. 73 | 350 | 460 | * | DI Water | 15 | 0 | 0 | 17 | 65 | 100 | 100 | 100 |
| 33 | Ex. 1 | Ex. 73 | 350 | 460 | * | DI Water | 15 | 0 | 0 | 35 | 97 | 100 | 100 | 100 |
| 34 | Ex. 1 | Ex. 73 | 350 | 460 | * | DI Water | 15 | 0 | 0 | 14 | 89 | 100 | 100 | 100 |
| 35 | Ex. 1 | Ex. 73 | 400 | 510 | * | DI Water | 15 | 0 | 0 | 0 | 69 | 100 | 100 | 100 |
| 36 | Ex. 1 | Ex. 73 | 400 | 510 | * | DI Water | 15 | 0 | 0 | 11 | 45 | 97 | 100 | 100 |
| 37 | Ex. 1 | Ex. 73 | 400 | 510 | * | DI Water | 15 | 0 | 0 | 12 | 48 | 96 | 100 | 100 |
| 38 | Ex. 1 | Ex. 81 | 350 | 460 | * | DI Water | 15 | 0 | 0 | 14 | 76 | 100 | 100 | 100 |
| 39 | Ex. 1 | Ex. 81 | 350 | 460 | * | DI Water | 15 | 0 | 0 | 59 | 98 | 100 | 100 | 100 |

TABLE 75-continued

| | | | | | | | | 0 | 1 | 2 | 3 | 4 | 5 | 6 |
|---|---|---|---|---|---|---|---|---|---|---|---|---|---|---|
| 40 | Ex. 1 | Ex. 81 | 350 | 460 | * | DI Water | 15 | 0 | 0 | 35 | 77 | 100 | 100 | 100 |
| | | | | | | | | 0 | 1 | 2 | 3 | 4 | 5 | 6 |
| 41 | Ex. 1 | Ex. 81 | 400 | 510 | * | DI Water | 15 | 0 | 2 | 2 | 49 | 100 | 100 | 100 |
| | | | | | | | | 0 | 1 | 2 | 3 | 4 | 5 | 6 |
| 42 | Ex. 1 | Ex. 81 | 400 | 510 | * | DI Water | 15 | 0 | 0 | 0 | 58 | 86 | 100 | 100 |
| | | | | | | | | 0 | 1 | 2 | 3 | 4 | 5 | 6 |
| 43 | Ex. 1 | Ex. 81 | 400 | 510 | * | DI Water | 15 | 0 | 0 | 0 | 58 | 100 | 100 | 100 |
| | | | | | | | | 0 | 1 | 2 | 3 | 4 | 5 | 6 |
| 44 | Ex. 1 | Ex. 81 | 300 | 410 | * | DI Water | 15 | 0 | 0 | 70 | 995 | 100 | 100 | 100 |
| | | | | | | | | 0 | 1 | 2 | 3 | 4 | 5 | 6 |
| 45 | Ex. 1 | Ex. 81 | 300 | 410 | * | DI Water | 15 | 0 | 0 | 0 | 80 | 100 | 100 | 100 |
| | | | | | | | | 0 | 1 | 2 | 3 | 4 | 5 | 6 |
| 46 | Ex. 1 | Ex. 81 | 300 | 410 | * | DI Water | 15 | 0 | 0 | 59 | 85 | 100 | 100 | 100 |
| | | | | | | | | 0 | 1 | 3 | 5 | 8 | 11 | 14 |
| 47 | Ex. 1 | Ex. 78 | 350 | 460 | * | pH change | 15 | 0 | 1 | 1 | 16 | 56 | 97 | 100 |
| | | | | | | | | 0 | 1 | 3 | 5 | 8 | 11 | 14 |
| 48 | Ex. 1 | Ex. 80 | 350 | 460 | * | pH change | 15 | 0 | 0 | 1 | 16 | 68 | 97 | 100 |
| | | | | | | | | 0 | 1 | 3 | 5 | 8 | 11 | 14 |
| 49 | Ex. 1 | Ex. 76 | 350 | 460 | * | pH change | 15 | 0 | 0 | 2 | 19 | 53 | 94 | 100 |
| | | | | | | | | 0 | 1 | 3 | 5 | 8 | 11 | 14 |
| 50 | Ex. 1 | Ex. 81 | 350 | 460 | * | pH change | 15 | 0 | 0 | 1 | 15 | 63 | 96 | 100 |

* = 10.3 mm

The effects of the different percentages of gums within the sustained release coating are shown in Table 76 below:

TABLE 76

| Ex. 1 coating 300 mg coating Example 70 Core | | Ex. 1 coating 446 mg coating Example 71 Core | | Ex. 2 coating 300 mg coating Example 70 Core | | Ex. 3 coating 446 mg coating Example 71 Core | |
|---|---|---|---|---|---|---|---|
| Time (hrs.) | % released | Time (hrs.) | % released | Time (hrs.) | % released | Time (hrs.) | % released |
| 0 | 0 | 0 | 0 | 0 | 0 | 0 | 0 |
| 2 | 0.4 | 2 | 13.7 | 8 | 39.6 | 4 | 7.7 |
| 3 | 8.4 | 3 | 51.2 | 10 | 67.5 | 6 | 28.3 |
| 3.5 | 29.6 | 4 | 99.3 | 12 | 83.5 | 8 | 56.7 |
| 4 | 74.8 | 5 | 100 | 14 | 96.2 | 10 | 88.7 |
| 4.5 | 99.1 | 6 | 100 | 16 | 99.5 | 12 | 100 |
| 5.0 | 100 | 7 | 100 | 18 | 100 | 16 | 100 |

| Ex. 4 coating 300 mg coating Example 70 Core | | Ex. 10 coating 450 mg coating Example 72 Core | | Ex. 10 coating 500 mg coating Example 70 Core | |
|---|---|---|---|---|---|
| Time (hrs.) | % released | Time (hrs.) | % released | Time (hrs.) | % released |
| 0 | 0 | 0 | 0 | 0 | 0 |
| 1 | 0 | 4 | 0 | 2 | 0 |
| 2 | 0 | 4.5 | 0 | 3 | 0 |
| 3 | 13.3 | 5 | 12.6 | 4 | 0.3 |
| 4 | 30.6 | 5.5 | 72.3 | 5 | 40.1 |
| 5 | 79.2 | 6 | 98.3 | 6 | 98.4 |
| 6 | 100 | 6.5 | 100 | 7 | 100 |

As shown in the Table 76, the formulation with 20% gums released the active drug faster than formulations with 30% or 50% gums. The coating used affects the release rate. In Example 82(a), delayed release coating formulations were prepared in order to determine the effect of the coating weight and compression force on the time of release and the rate of release of the active agent within the tablet core.

Example 83

A metoprolol core composition was prepared having the formulation ingredients set forth in Table 77:

TABLE 77

| Component | Percent | Amt. (mg) |
|---|---|---|
| 1. Metoprolol Tartrate | 47.5 | 100 |
| 2. Prosolv HD ™ 90 | 47.5 | 100 |
| 3. Hydroxypropyl methyl cellulose | 5 | 11 |
| 4. Explotab | 4 | 10 |
| 5. Ac-Di-Sol | 2 | 5 |
| 6. Prosolv | 5.75 | 14 |

TABLE 77-continued

| Component | Percent | Amt. (mg) |
|---|---|---|
| 7. Talc | 4 | 10 |
| 8. Pruv | 0.25 | 1 |
| Total | 100 | 250 |
| Film coating 6% (6.6 mg) Opadry AMB | | |

Process:

The same process for Example 23 is used to prepare the core, except that a film coating is included in Example 83.

The core of Example 83 was then compression coated with compression coating materials from previous examples and the resultant tablets were subjected to in-vitro dissolution studies, as set forth in Table 78 below.

TABLE 78

| Test | Active Compound | Active Dose | TIMERx Grade | Core Reference | TIMERx Amount | Tablet Weight | Coating Size | Dissolution Media | Dissol dpm | Dissolution Time (hrs) (shaded) vs. % Dissolved |||||||
|---|---|---|---|---|---|---|---|---|---|---|---|---|---|---|---|---|
| | | | | | | | | | | 0 | 3 | 4 | 5 | 6 | 7 | 8 |
| 1 | Metoprolol | 100 | Ex. 10 | Ex. 83 | 750 | 1000 | 1/2 | DI Water | 15 | 0 | 0 | 5 | 35 | 66 | 99 | 100 |
| | | | | | | | | | | 0 | 3 | 4 | 5 | 6 | 7 | 8 |
| 2 | Metoprolol | 100 | Ex. 10 | Ex. 83 | 750 | 1000 | 1/2 | DI Water | 15 | 0 | 0 | 0 | 3 | 66 | 72 | 99 |
| | | | | | | | | | | 0 | 8 | 10 | 12 | 14 | 16 | 20 |
| 3 | Metoprolol | 100 | Ex. 2 | Ex. 83 | 600 | 850 | 7/16 | DI Water | 15 | 0 | 13 | 22 | 36 | 48 | 71 | 99 |
| | | | | | | | | | | 0 | 8 | 10 | 12 | 14 | 16 | 20 |
| 4 | Metoprolol | 100 | Ex. 2 | Ex. 83 | 750 | 1000 | 1/2 | DI Water | 15 | 0 | 11 | 26 | 41 | 56 | 68 | 89 |
| | | | | | | | | | | 0 | 2 | 3 | 4 | 5 | 6 | 8 |
| 5 | Metoprolol | 100 | Ex. 4 | Ex. 83 | 600 | 850 | 7/16 | DI Water | 15 | 0 | 0 | 1 | 6 | 35 | 53 | 88 |
| | | | | | | | | | | 0 | 2 | 3 | 4 | 5 | 6 | 8 |
| 6 | Metoprolol | 100 | Ex. 4 | Ex. 83 | 500 | 750 | 7/16 | DI Water | 15 | 0 | 0 | 0 | 6 | 16 | 70 | 100 |

The examples provided above are not meant to be exclusive. Many other variations of the present invention would be obvious to those skilled in the art, and are contemplated to be within the scope of the appended claims.

What is claimed is:

1. A delayed release oral solid dosage form, comprising a core comprising a therapeutically effective amount of a drug, and an agglomerated delayed release material compression coated onto said core, said delayed release material consisting essentially of an effective amount of xanthan gum and locust bean gum and an optional ingredient selected from the group consisting of a saccharide, an ionizable gel strength enhancing agent, a surfactant, a hydrophobic material, and any combinations thereof, said delayed release material providing a delay of the release of said drug from said dosage form until after a period of time from about 2 to about 18 hours after exposure of the dosage form to an aqueous solution.

2. The delayed release oral solid dosage form of claim 1, wherein said xanthan gum and locust bean gum are agglomerated with said saccharide material prior to being compression coated onto said core.

3. The delayed release oral solid dosage form of claim 1, which delays release of said drug until at least about 4 hours after exposure of the dosage form to an aqueous solution.

4. The delayed release oral solid dosage form of claim 1, wherein said ionizable gel strength enhancing agent is selected from the group consisting of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, and mixtures thereof.

5. The delayed release oral solid dosage form of claim 4, wherein said ionizable gel strength enhancing agent is calcium sulfate.

6. The delayed release oral solid dosage form of claim 1, wherein said surfactant is selected from the group consisting of anionic surfactants, cationic surfactants, amphoteric (amphipathic/amphophilic) surfactants, and non-ionic surfactants.

7. The delayed release oral solid dosage form of claim 1, wherein said hydrophobic material comprises ethylcellulose.

8. The delayed release oral solid dosage form of claim 2, wherein said saccharide is selected from the group consisting of sucrose, dextrose, lactose, fructose, mannitol, and mixtures thereof.

9. The delayed release oral solid dosage form of claim 1, wherein said core further comprises from about 5 to about 20 percent disintegrant, by weight.

10. The delayed release oral solid dosage form of claim 9, wherein said disintegrant is a superdisintegrant.

11. The delayed release oral solid dosage form of claim 9, wherein said disintegrant is selected from the group consisting of starch, veegum, crospovidone, cellulose, kaolin, microcrystalline cellulose, crosslinked polyvinyl pyrrolidone, and mixtures thereof.

12. The delayed release oral solid dosage form of claim 10, wherein said superdisintegrant is selected from the group consisting of croscarmellose sodium, crospovidone, crosslinked carboxy methyl cellulose, sodium starch glycolate, and mixtures thereof.

13. The delayed release oral solid dosage form of claim 1, wherein said core further comprises an inert diluent selected from the group consisting of sucrose, dextrose, lactose, microcrystalline cellulose, fructose, xylitol, sorbitol, mannitol, starches, mixtures thereof.

14. The delayed release oral solid dosage form of claim 1, wherein said core is an immediate release core.

15. The delayed release oral solid dosage form of claim 1, wherein said core further comprises a sustained release carrier.

16. The delayed release oral solid dosage form of claim 1, wherein said xanthan gum is in an amount of from about 20 to about 80 percent of the delayed release material and said locust bean gum is in an amount of from about 80 to about 20 percent of the delayed release material.

17. A method of preparing a chronotherapeutic oral solid dosage form of a drug, comprising:
preparing a core comprising a therapeutically effective amount of a drug and from about 5 to about 20% of an optional disintegrant, by weight of the core,
preparing an agglomerated delayed release material consisting essentially of xanthan gum and locust bean gum and an optional ingredient selected from the group consisting of a saccharide, an ionizable gel strength enhancing agent, a surfactant, a hydrophobic material, and any combinations thereof,
compression coating said agglomerated delayed release material onto said core, said compression coating delaying the release of said drug from said dosage form until after a period of time from about 2 to about 18 hours after exposure of the dosage form to an aqueous solution.

18. The method of claim 17, further comprising preparing said agglomerated delayed release material by wet granulating said xanthan gum and said locust bean gum together with said optional ingredient to form a granulate, and drying the resultant granulate to obtain agglomerated particles of said delayed release material.

19. The method of claim 18, further comprising granulating said drug, said optional disintegrant, and a pharmaceutically acceptable inert diluent prior to said compression coating step.

20. The method of claim 19, wherein said disintegrant is a superdisintegrant incorporated into said core in an amount effective to cause the release of at least about 50 percent of said drug into said aqueous solution within one hour upon completion of the time period for said delayed release.

21. The delayed release oral solid dosage form of claim 1, wherein said xanthan gum and locust bean gum are in a combined amount of from about 5% to about 70% of the total dosage form, by weight.

22. The delayed release oral solid dosage form of claim 1, wherein said xanthan gum and locust bean gum are in a combined amount of from about 6.5% to about 83% of the total dosage form, by weight.

* * * * *